United States Patent
Choi et al.

(10) Patent No.: US 10,354,551 B2
(45) Date of Patent: Jul. 16, 2019

(54) MOBILE TERMINAL AND METHOD FOR CONTROLLING THE SAME

(71) Applicant: LG ELECTRONICS INC., Seoul (KR)

(72) Inventors: Heaju Choi, Seoul (KR); Eunhye Kim, Seoul (KR); Taeyoung Jeon, Seoul (KR); Yoomee Song, Seoul (KR); Jeongyoon Rhee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 160 days.

(21) Appl. No.: 15/302,893

(22) PCT Filed: Oct. 7, 2014

(86) PCT No.: PCT/KR2014/009426
§ 371 (c)(1),
(2) Date: Oct. 7, 2016

(87) PCT Pub. No.: WO2015/156461
PCT Pub. Date: Oct. 15, 2015

(65) Prior Publication Data
US 2017/0032692 A1    Feb. 2, 2017

(30) Foreign Application Priority Data

Apr. 9, 2014 (KR) .................. 10-2014-0042521
Jul. 25, 2014 (KR) .................. 10-2014-0095043

(51) Int. Cl.
*A63B 24/00* (2006.01)
*G09B 19/00* (2006.01)
*H04W 4/02* (2018.01)

(52) U.S. Cl.
CPC .......... *G09B 19/0038* (2013.01); *H04W 4/02* (2013.01); *H04W 4/027* (2013.01)

(58) Field of Classification Search
CPC ............................ A63B 24/00; A63B 24/006
See application file for complete search history.

(56) References Cited

U.S. PATENT DOCUMENTS

| | | | |
|---|---|---|---|
| 7,266,140 B1 * | 9/2007 | Hasegawa | G01S 19/23 342/357.68 |
| 7,771,320 B2 * | 8/2010 | Riley | A63B 24/0006 434/238 |

(Continued)

FOREIGN PATENT DOCUMENTS

| | | |
|---|---|---|
| CN | 102083505 A | 6/2011 |
| EP | 2618493 A1 | 7/2013 |

(Continued)

OTHER PUBLICATIONS

Duffy, "Moves (for iPhone)," PCMag.com, https://www.pcmag.com/article2/0,2817,2454045,00.asp, XP055410720, Feb. 24, 2014, 5 pages.

*Primary Examiner* — James S. McClellan
(74) *Attorney, Agent, or Firm* — Birch, Stewart, Kolasch & Birch, LLP

(57) ABSTRACT

Disclosed herein are a mobile terminal and a method for controlling the same. In the mobile terminal and the method for controlling the same, a circular time line is displayed when a specific application is executed. A motion of a user is sensed, and a tracking trajectory is displayed in the circular time line in real time. In this case, the tracking trajectory may be displayed so that it has a different display characteristic based on a type of the sensed motion of the user. Exercise information including an exercise type of a user can be displayed so that it is intuitively recognized over time. An exercise competition with a specific person or group members can be performed in real time. An exercise method suitable for a limited situation can be recommended.

20 Claims, 45 Drawing Sheets

(a)

(b)

(56) References Cited

U.S. PATENT DOCUMENTS

| | | | |
|---|---|---|---|
| 7,889,085 B2* | 2/2011 | Downey | A63B 24/0021 |
| | | | 340/539.13 |
| 9,304,205 B2* | 4/2016 | Heikes | G01C 22/006 |
| 2004/0233788 A1* | 11/2004 | Plancon | G04B 19/082 |
| | | | 368/11 |
| 2005/0017850 A1* | 1/2005 | Nissila | G04B 19/046 |
| | | | 340/407.1 |
| 2008/0081594 A1 | 4/2008 | Lee | |
| 2012/0066629 A1 | 3/2012 | Lee et al. | |
| 2013/0275078 A1 | 10/2013 | Tanabe et al. | |
| 2013/0325396 A1 | 12/2013 | Yuen et al. | |

FOREIGN PATENT DOCUMENTS

| | | |
|---|---|---|
| KR | 10-2008-0030350 A | 4/2008 |
| KR | 10-1031063 B1 | 4/2011 |
| KR | 10-2013-0077336 A | 7/2013 |
| WO | 2013/049248 A2 | 4/2013 |

\* cited by examiner

[Fig. 1a]
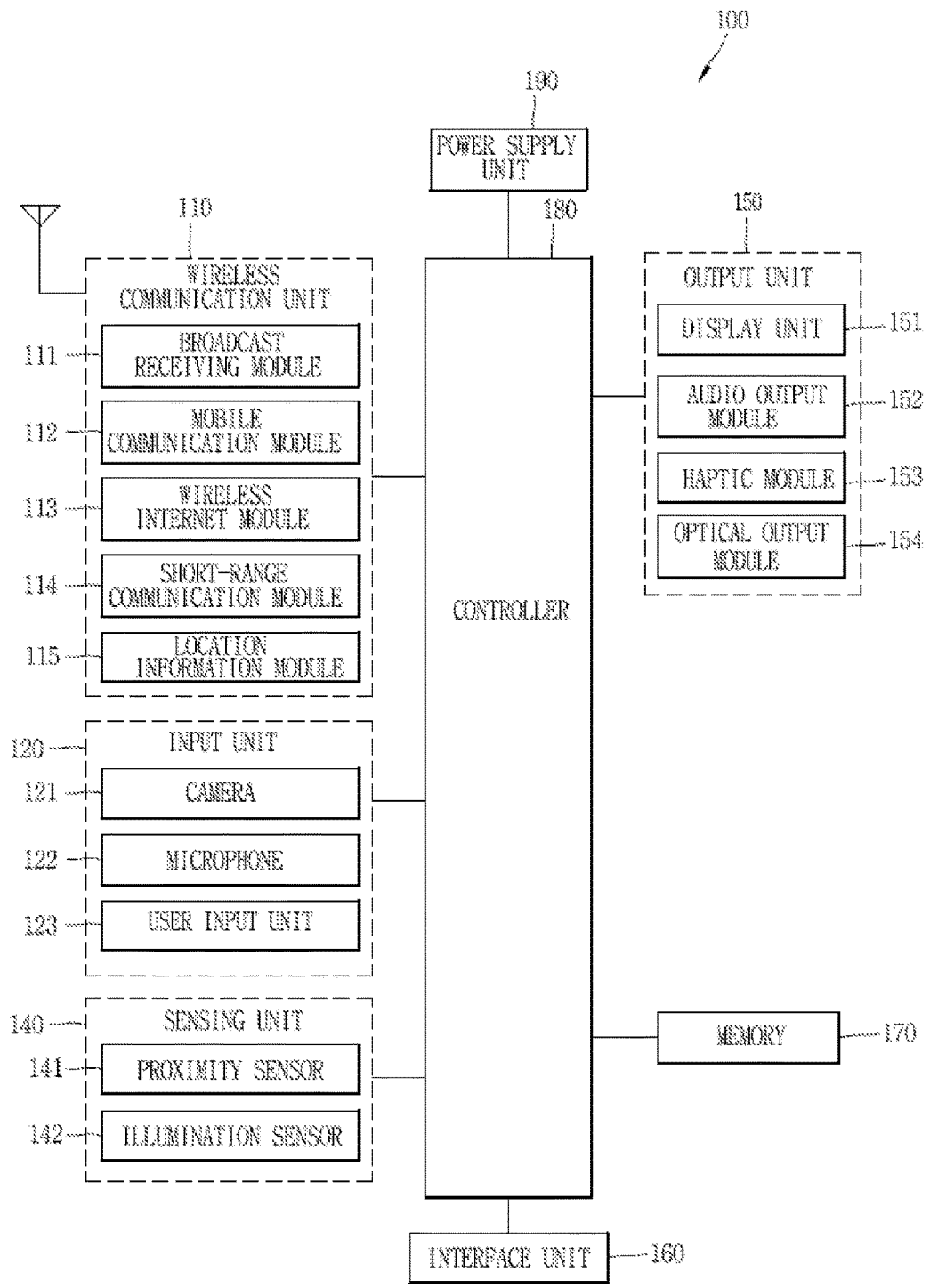

[Fig. 1b]
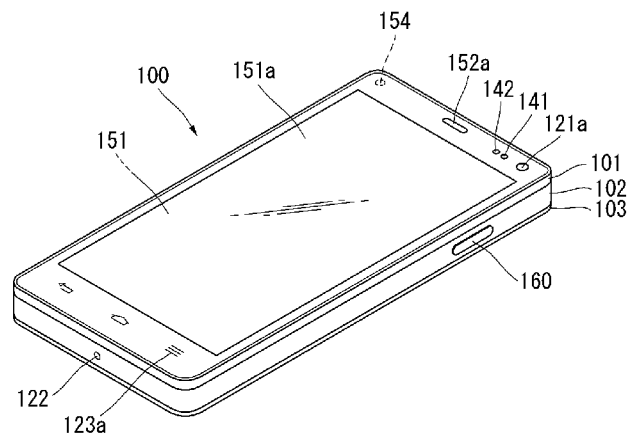
[Fig. 1c]
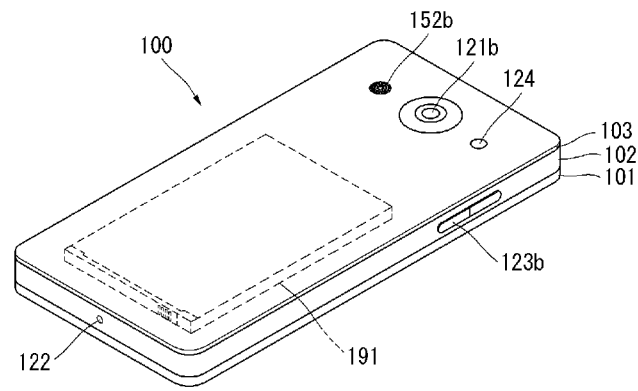

[Fig. 2]
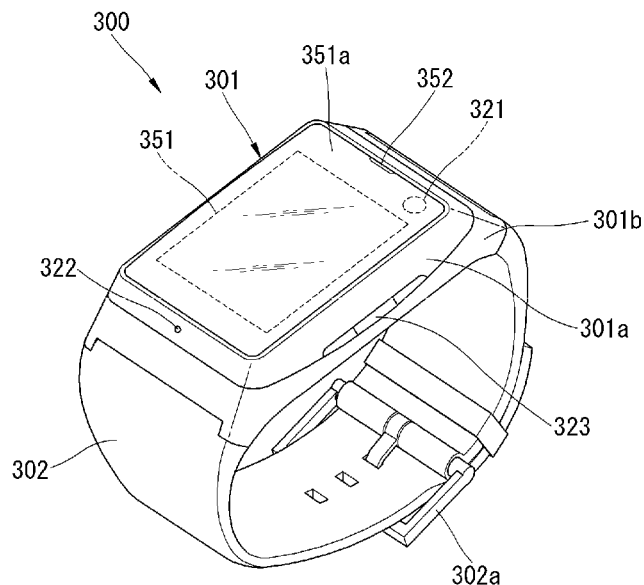
[Fig. 3]
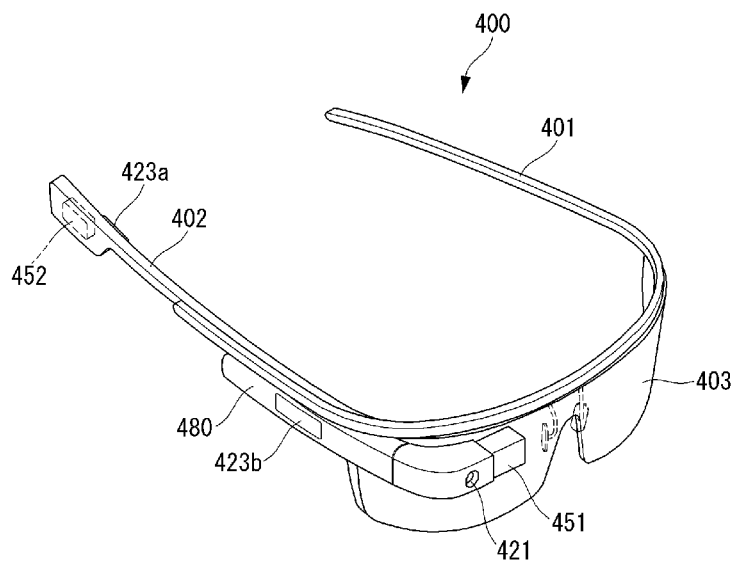

[Fig. 4]
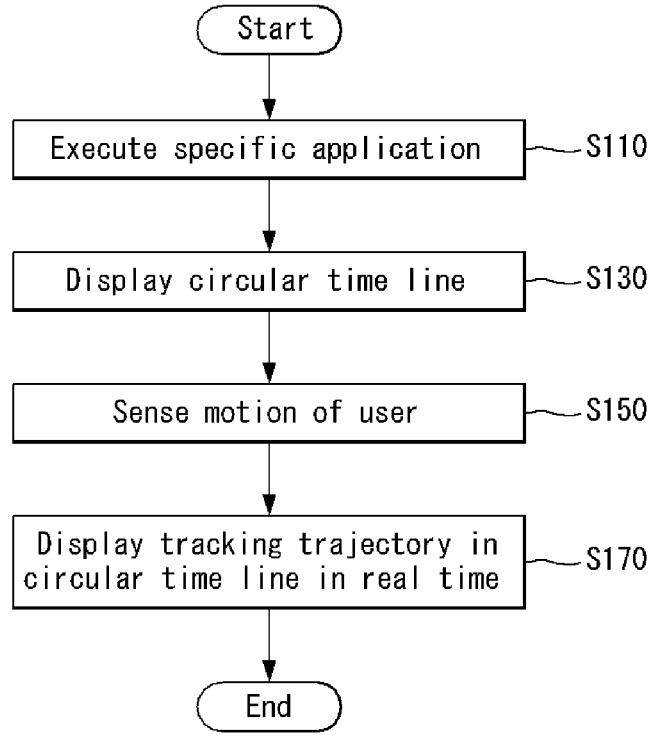
[Fig. 5]
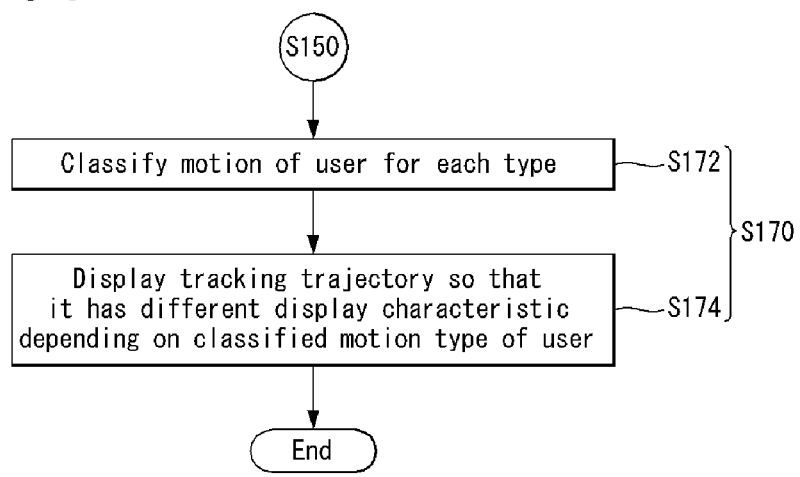

[Fig. 6]
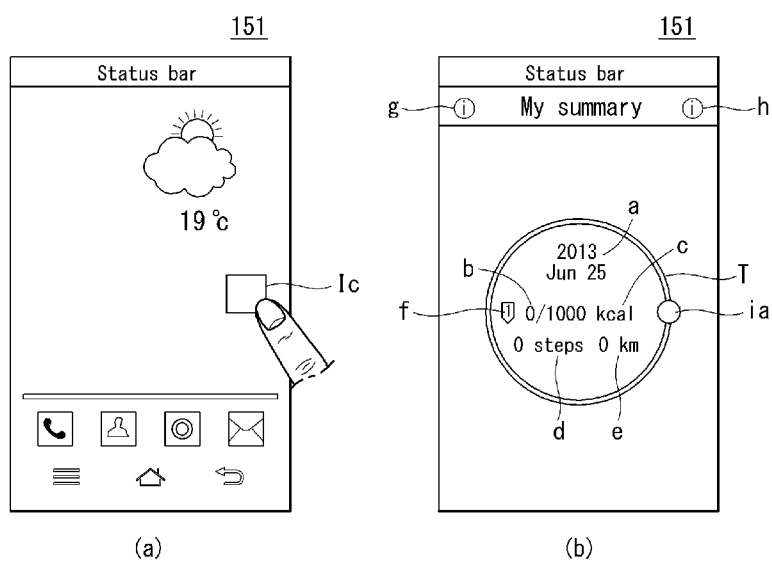

[Fig. 7]
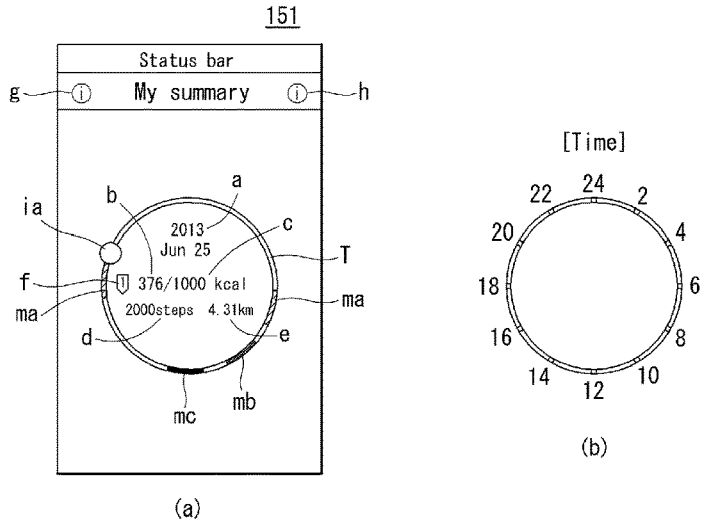
[Fig. 8]
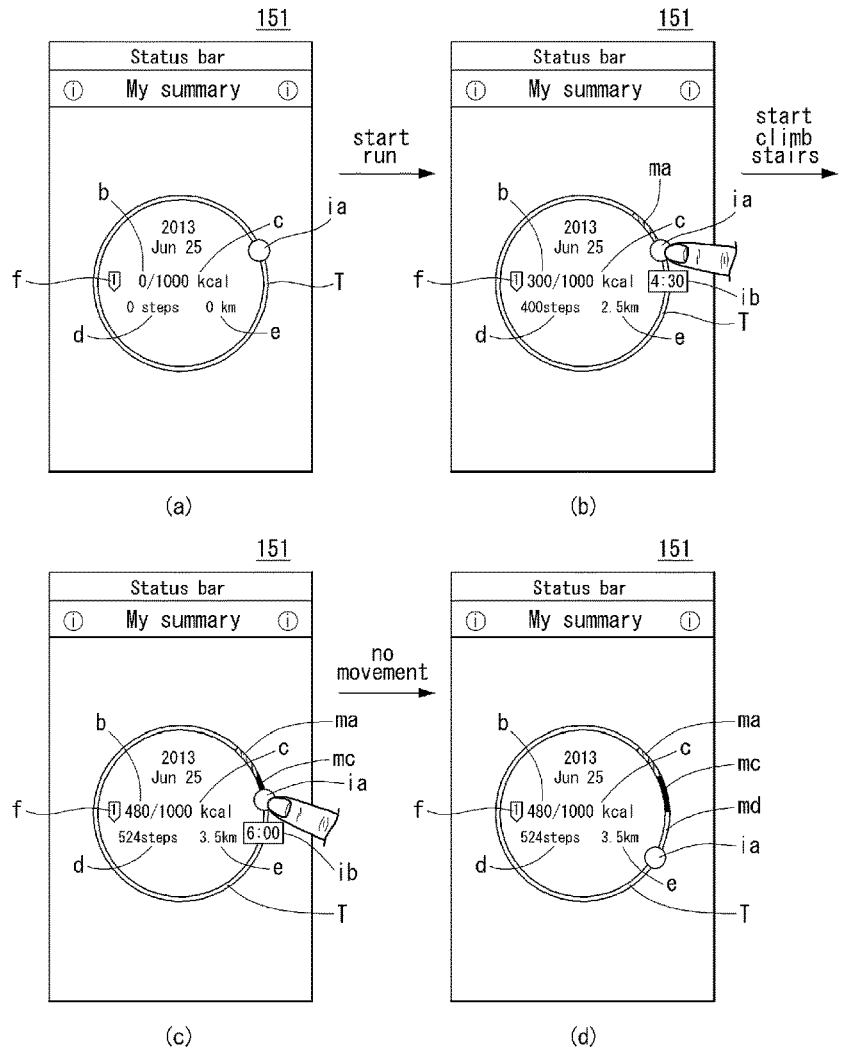

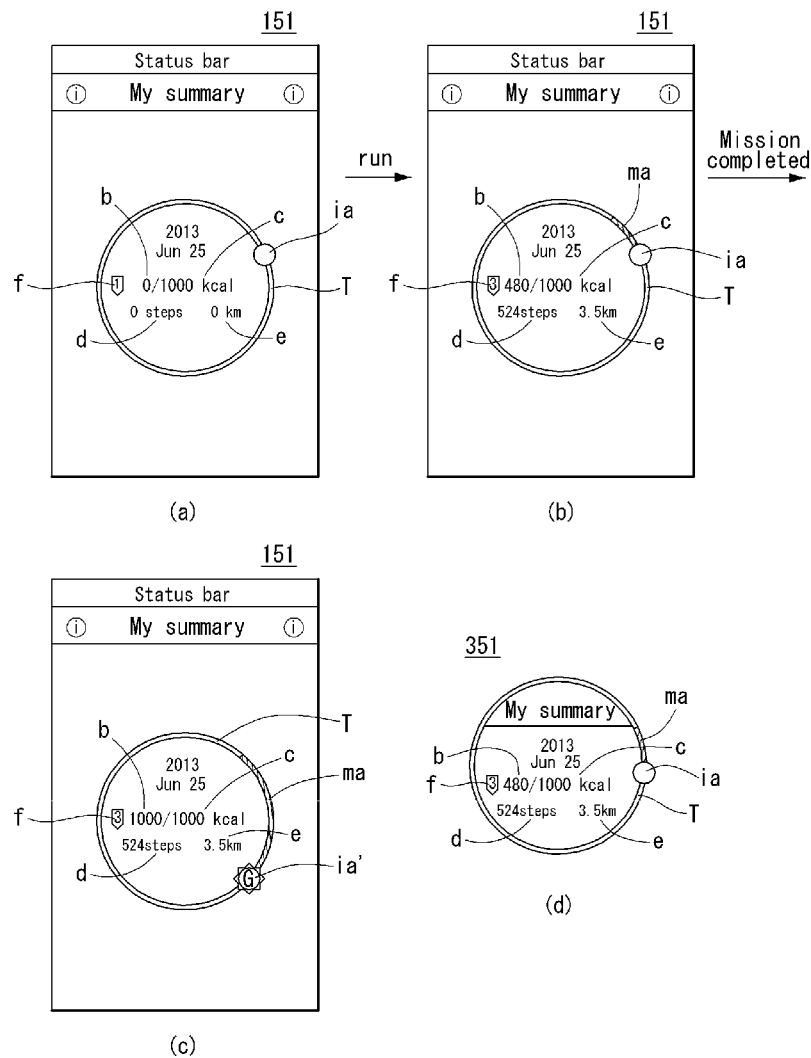
[Fig. 9]

[Fig. 10]
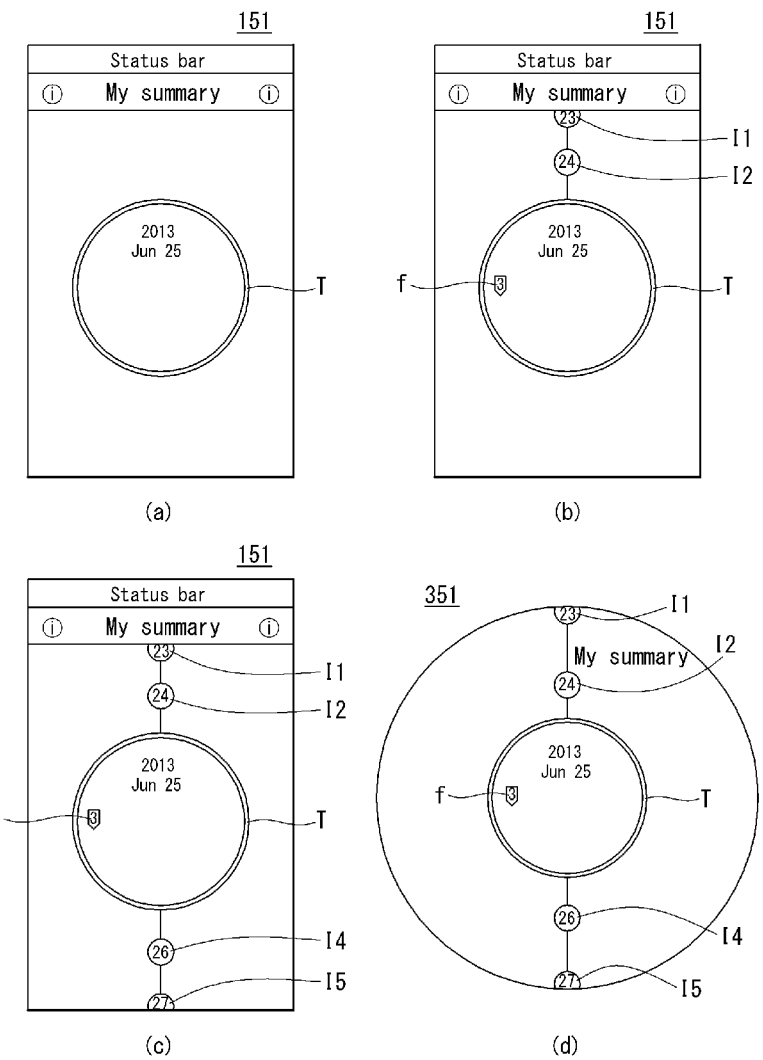

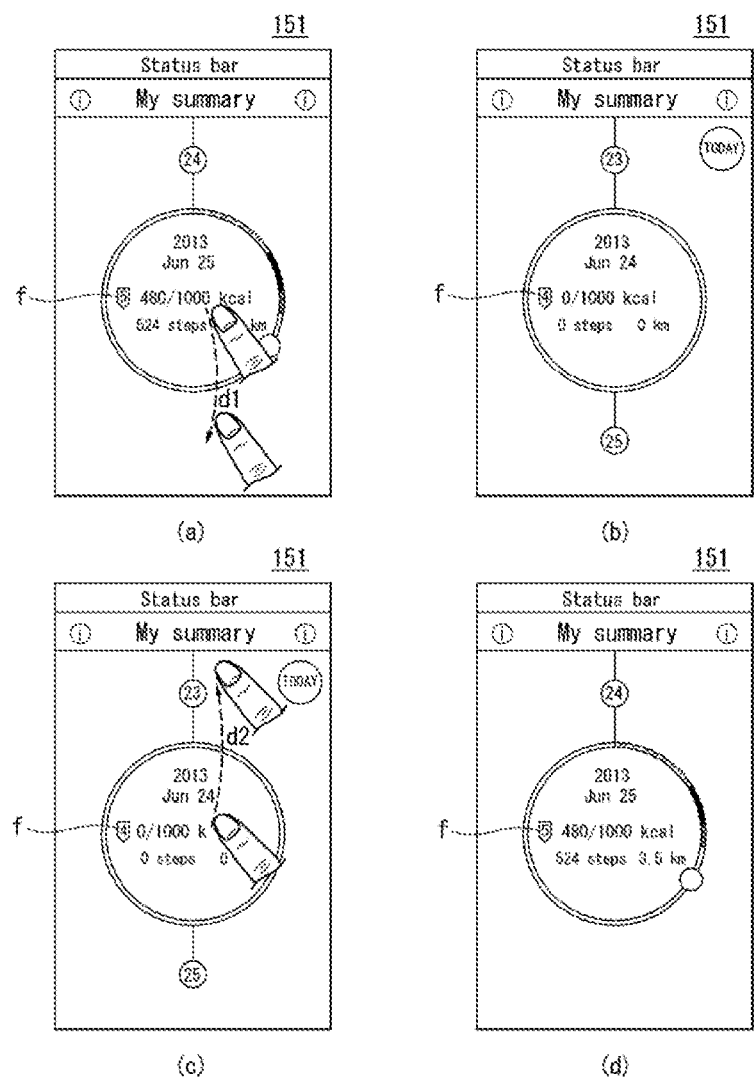
[Fig. 11]

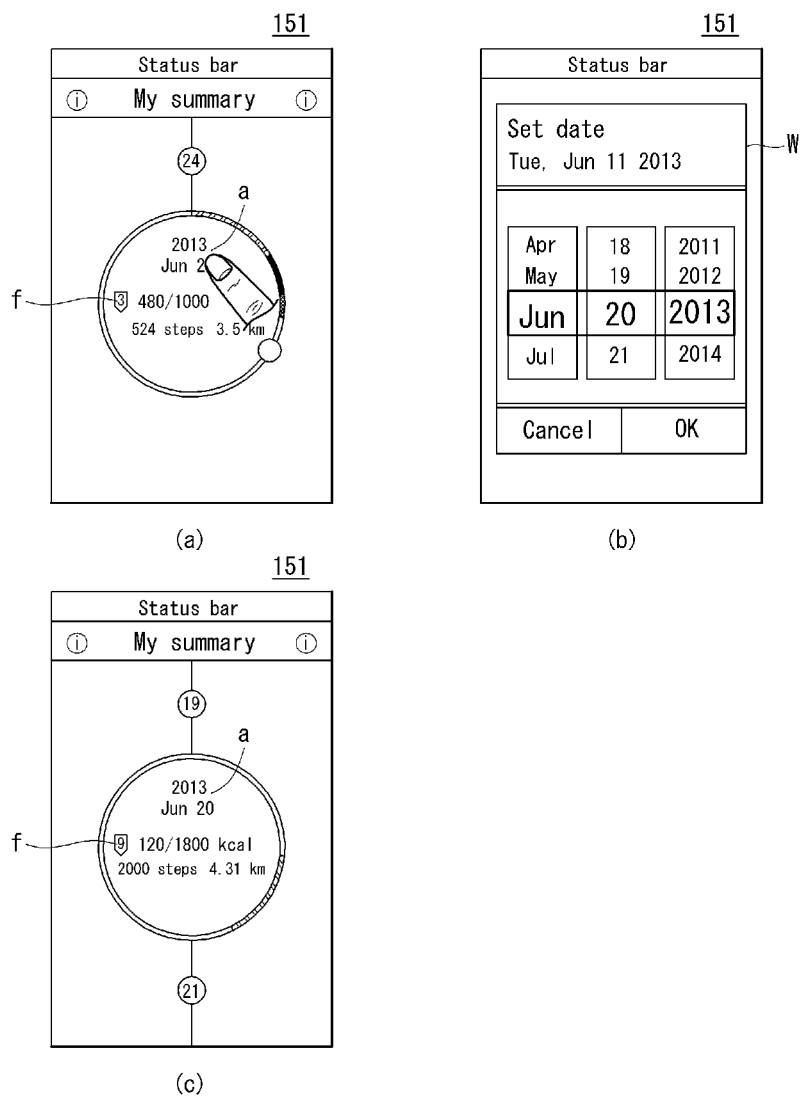
[Fig. 12]

[Fig. 13]
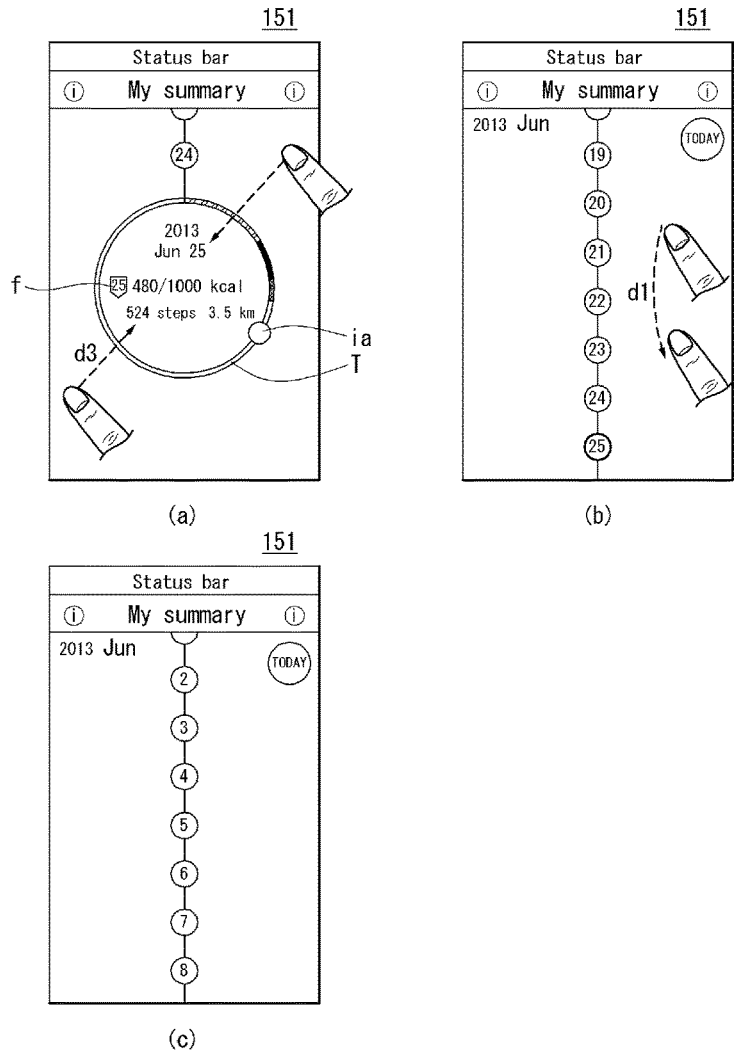
[Fig. 14]
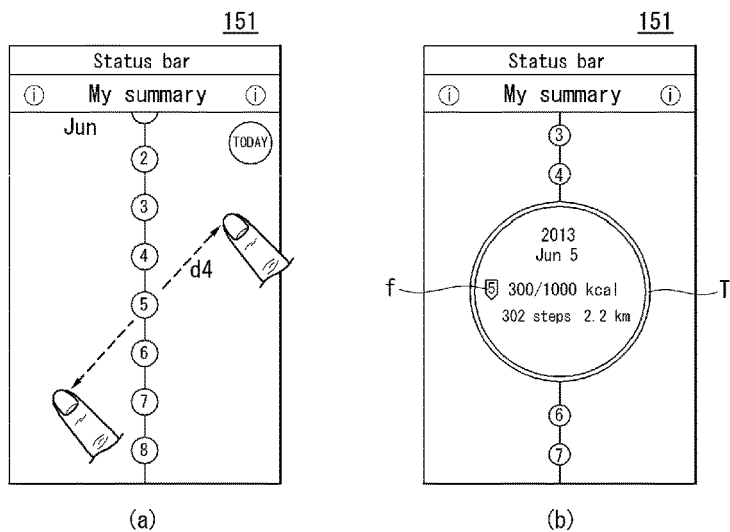

[Fig. 15]
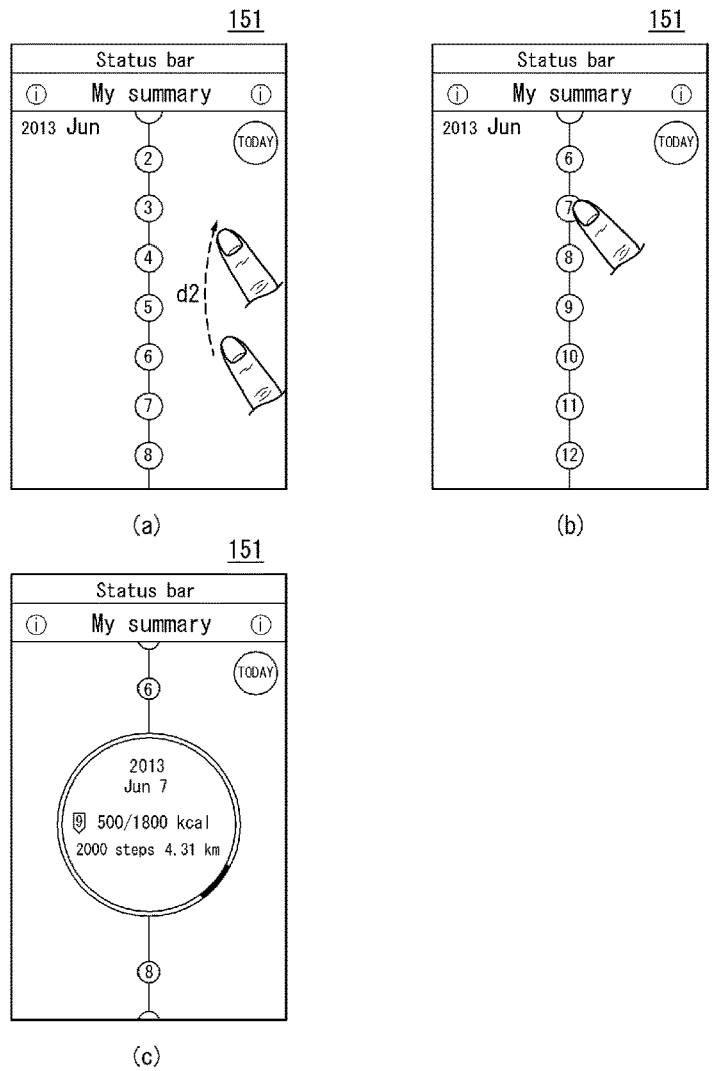
[Fig. 16]
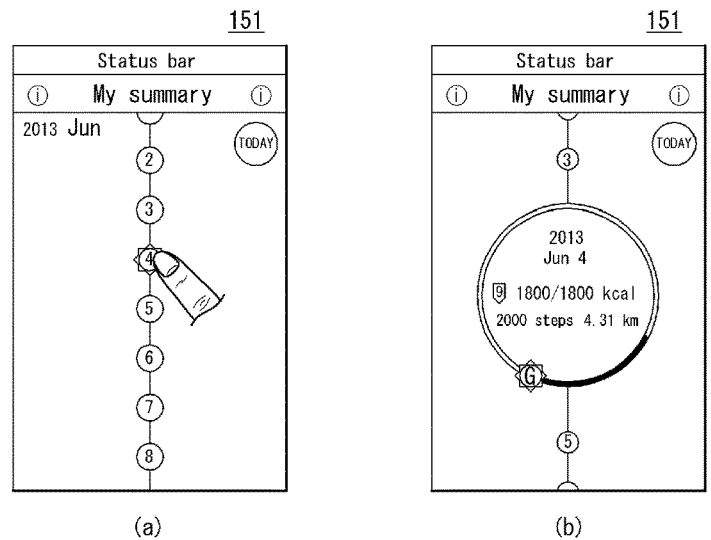

[Fig. 17]
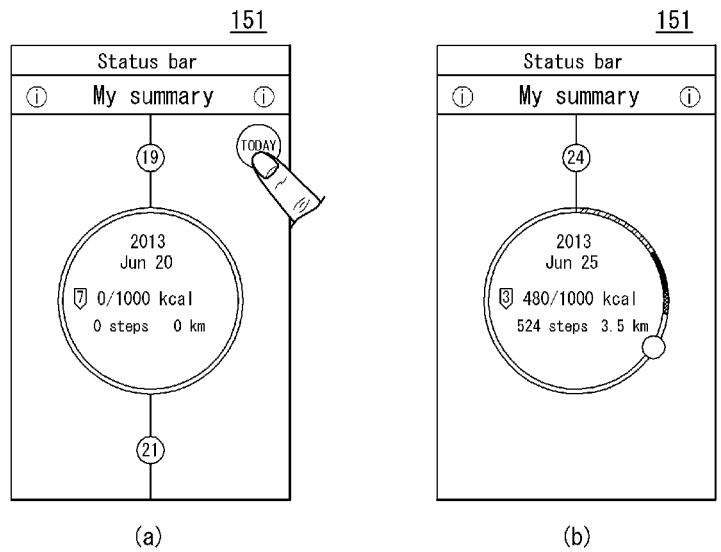
(a)   (b)
[Fig. 18]
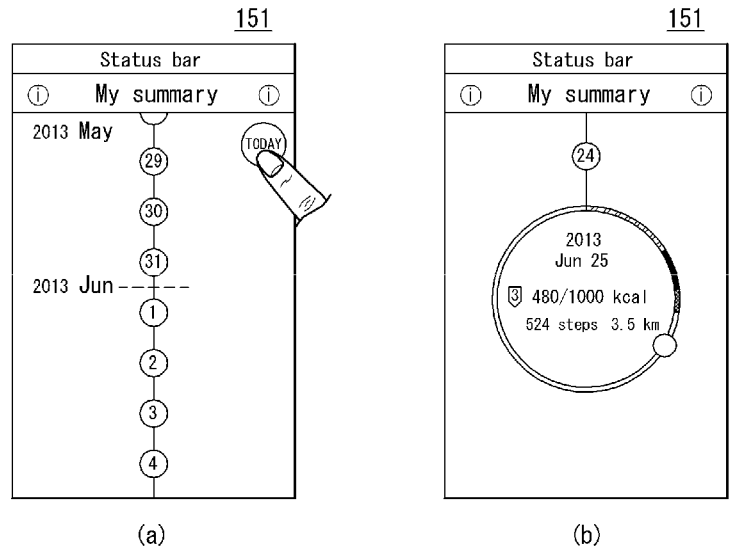
(a)   (b)

[Fig. 19]
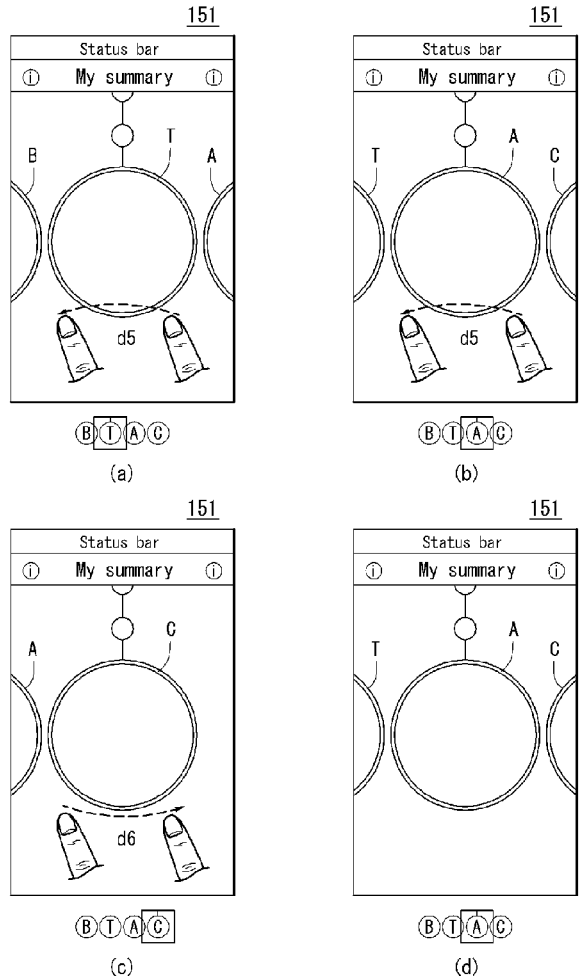
[Fig. 20]
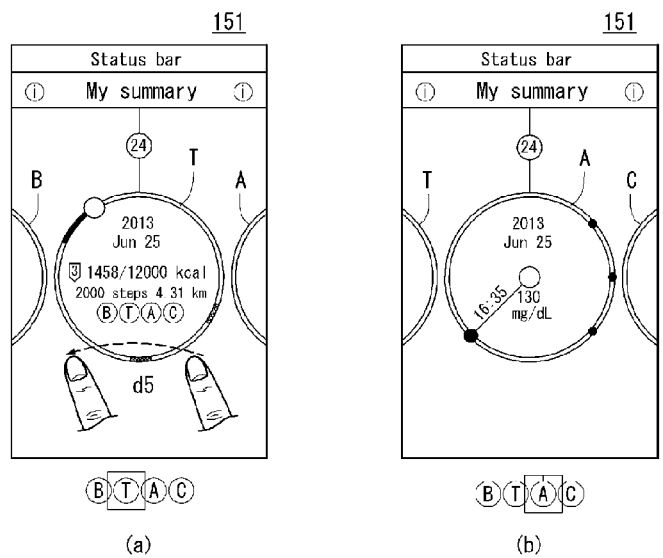

[Fig. 21]
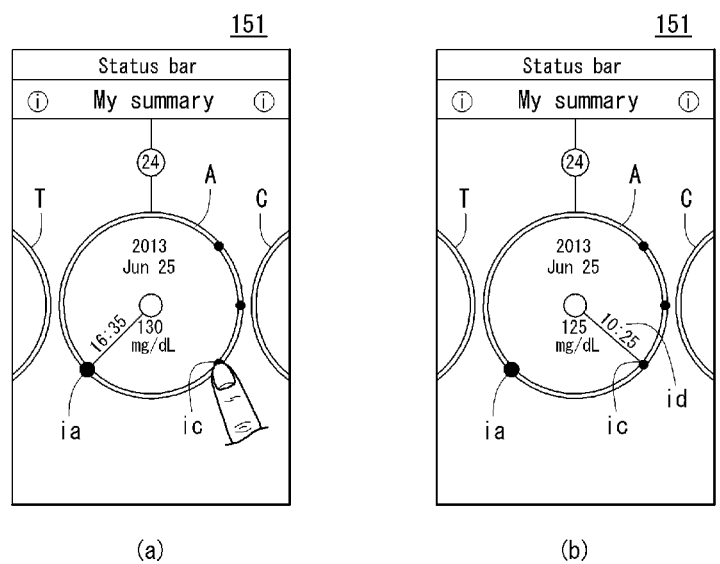

[Fig. 22]
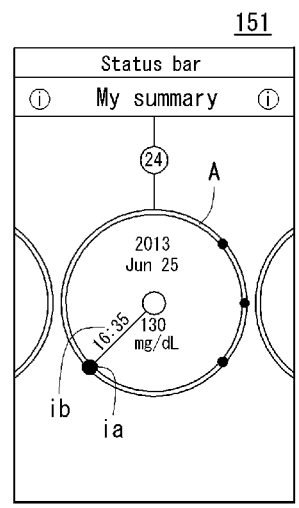
(a)
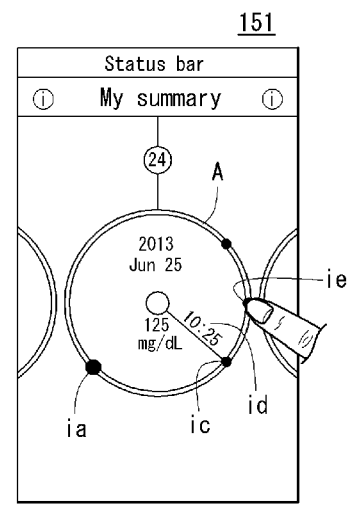
(b)
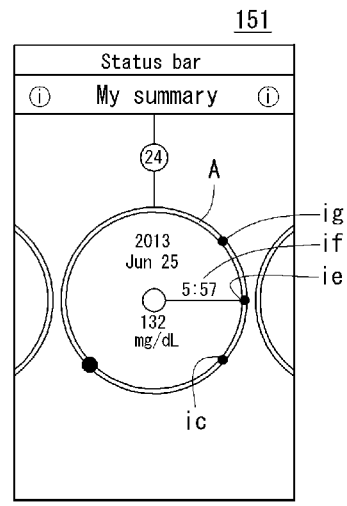
(c)

[Fig. 23]
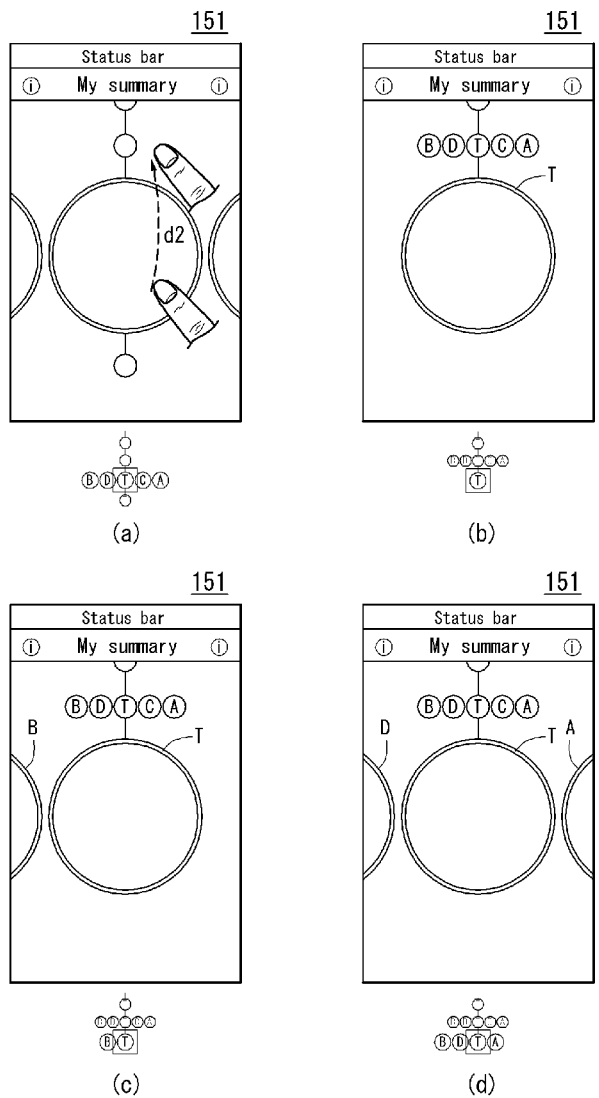

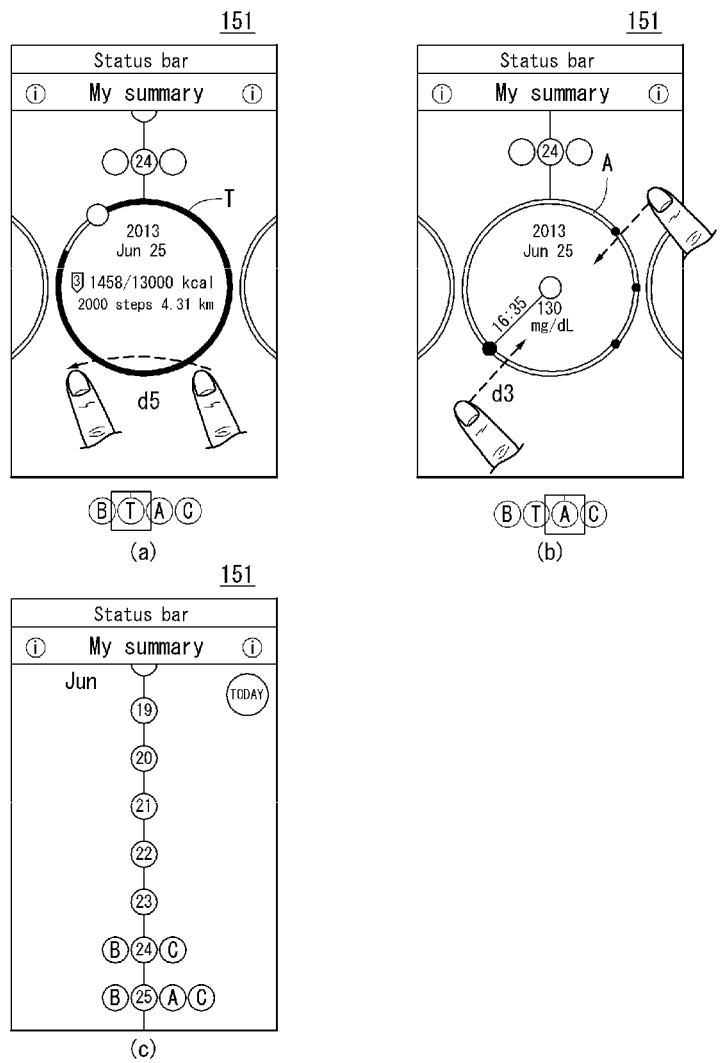
[Fig. 24]

[Fig. 25]
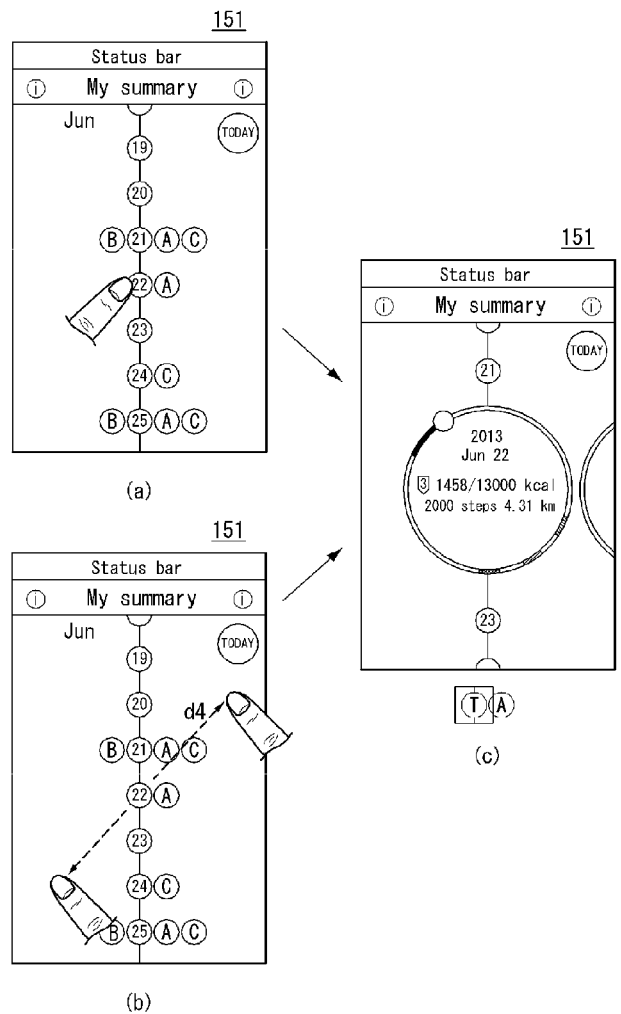
[Fig. 26]
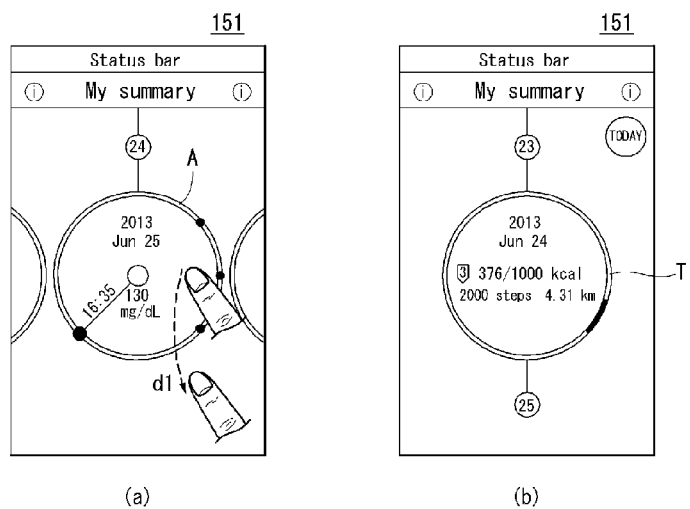

[Fig. 27]
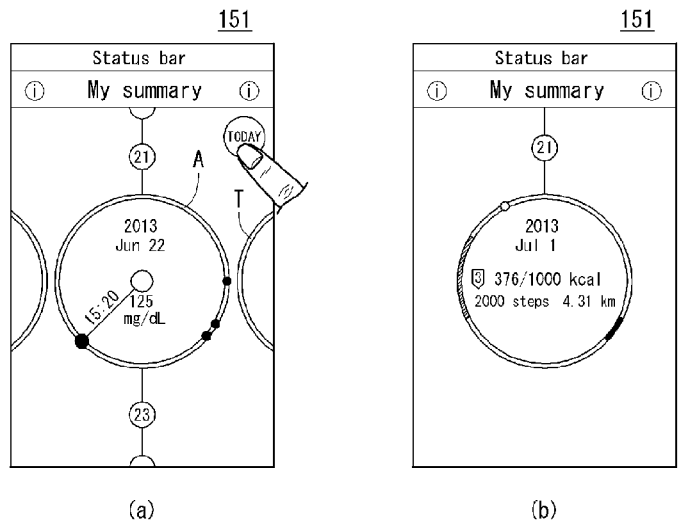
[Fig. 28]
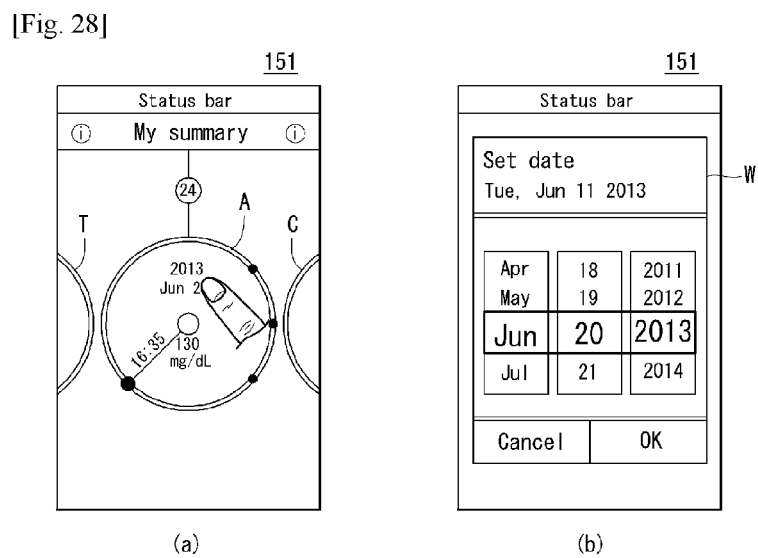
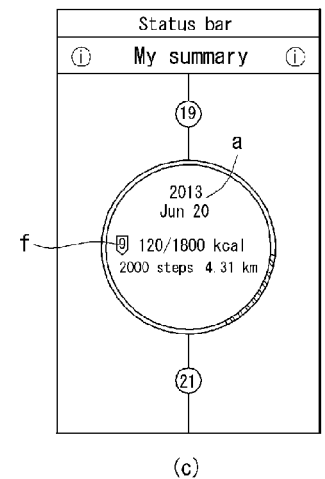

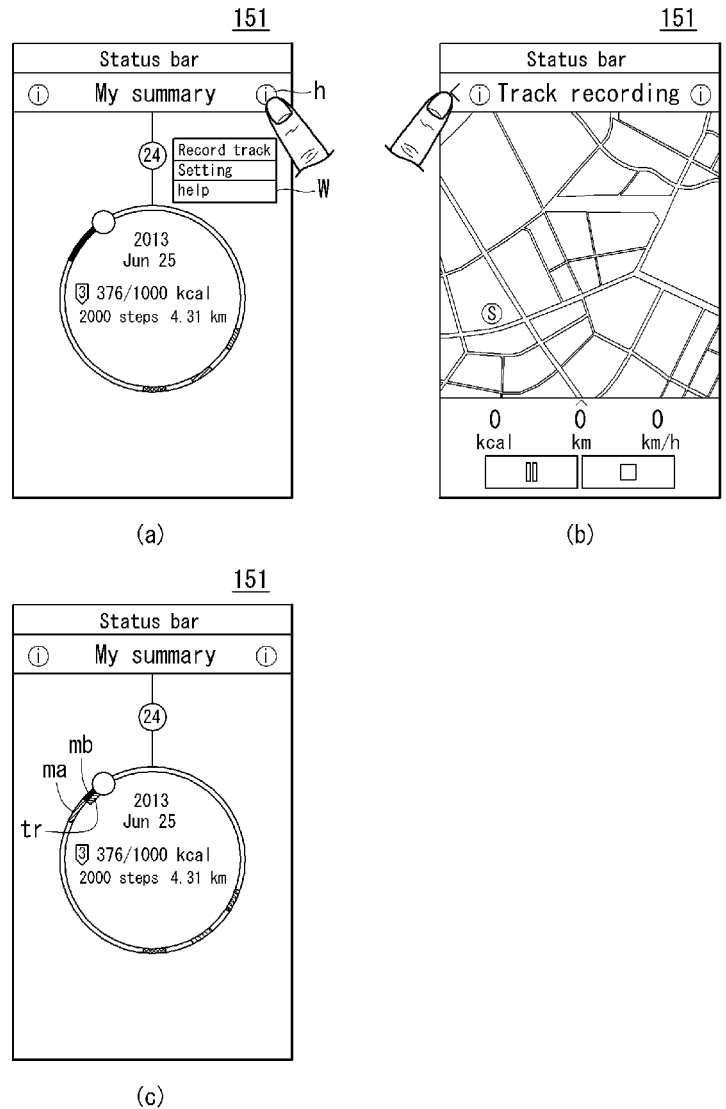
[Fig. 29]

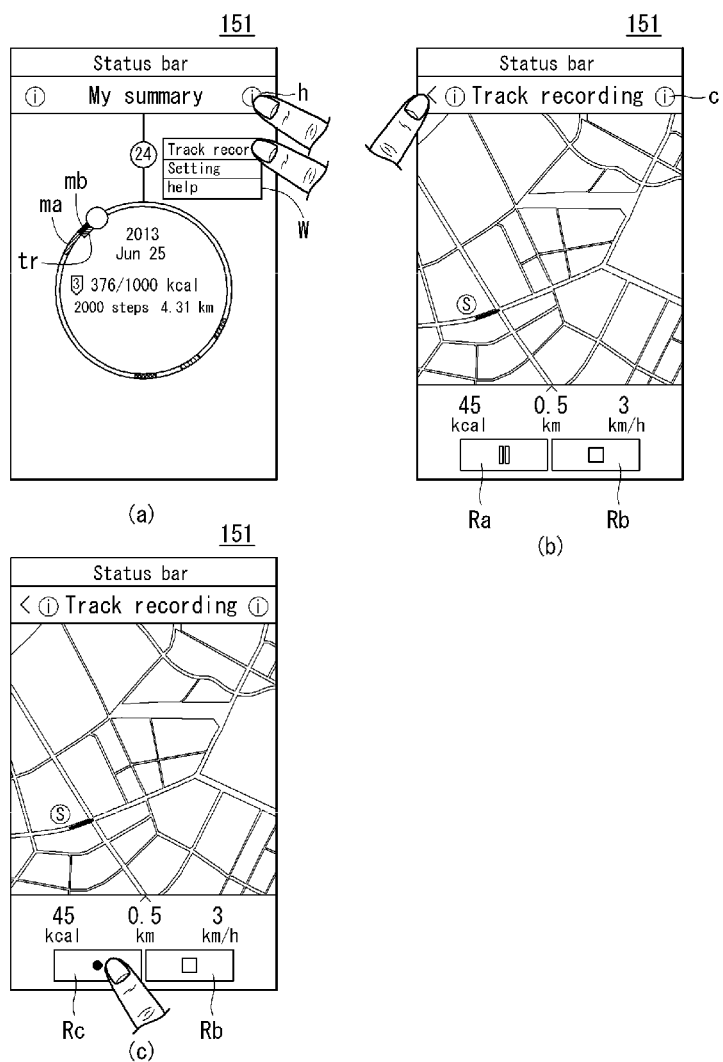
[Fig. 30]

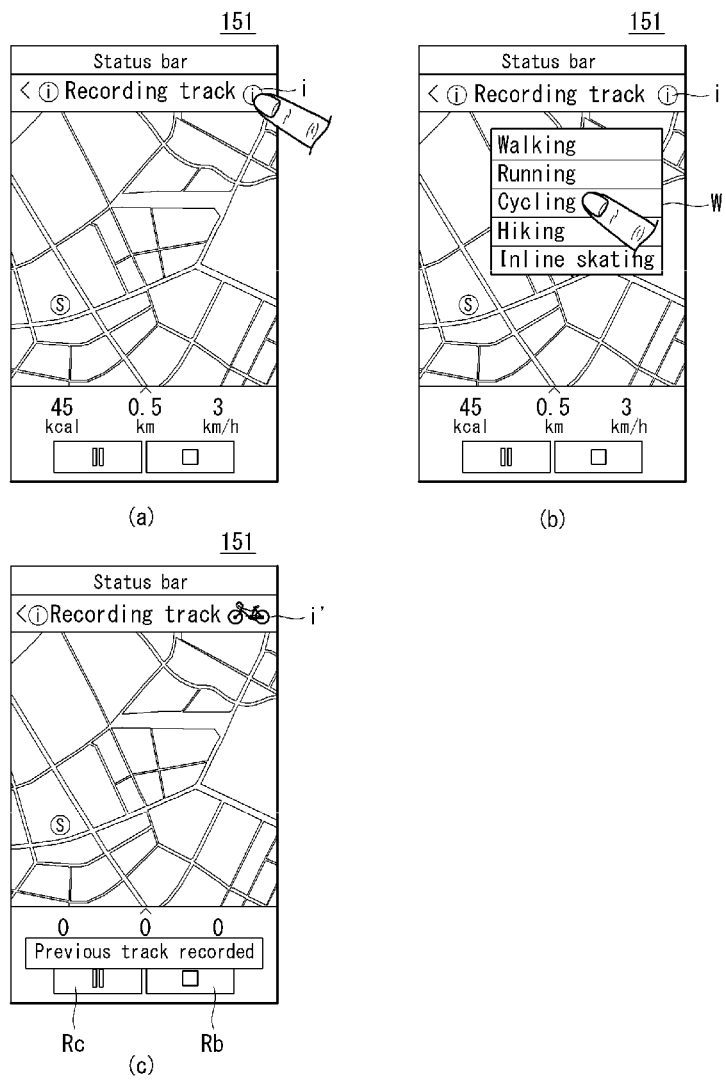
[Fig. 31]

[Fig. 32]
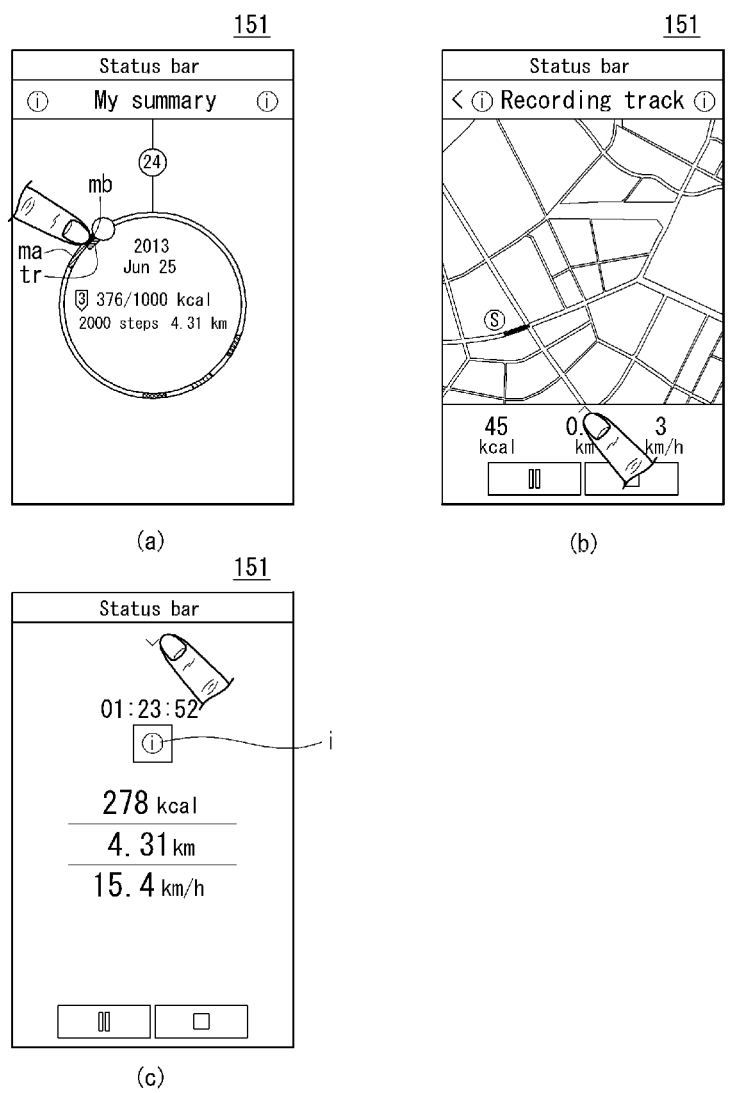

[Fig. 33]
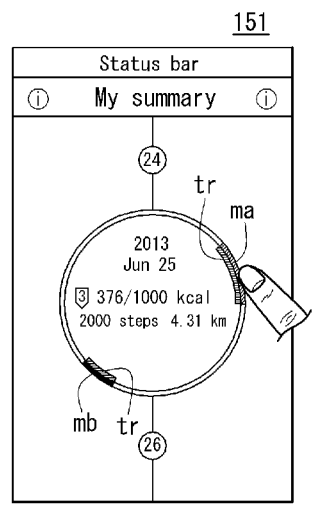
(a)
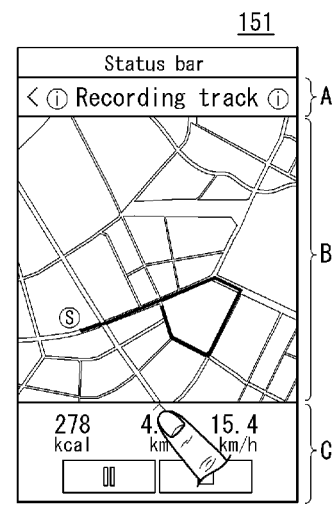
(b)
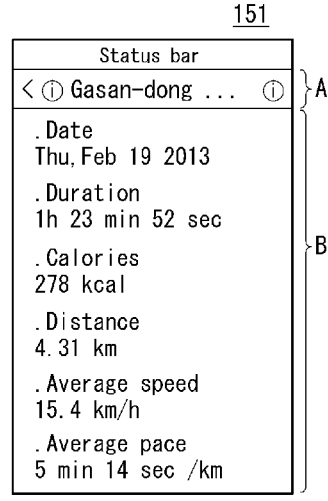
(c)

[Fig. 34]
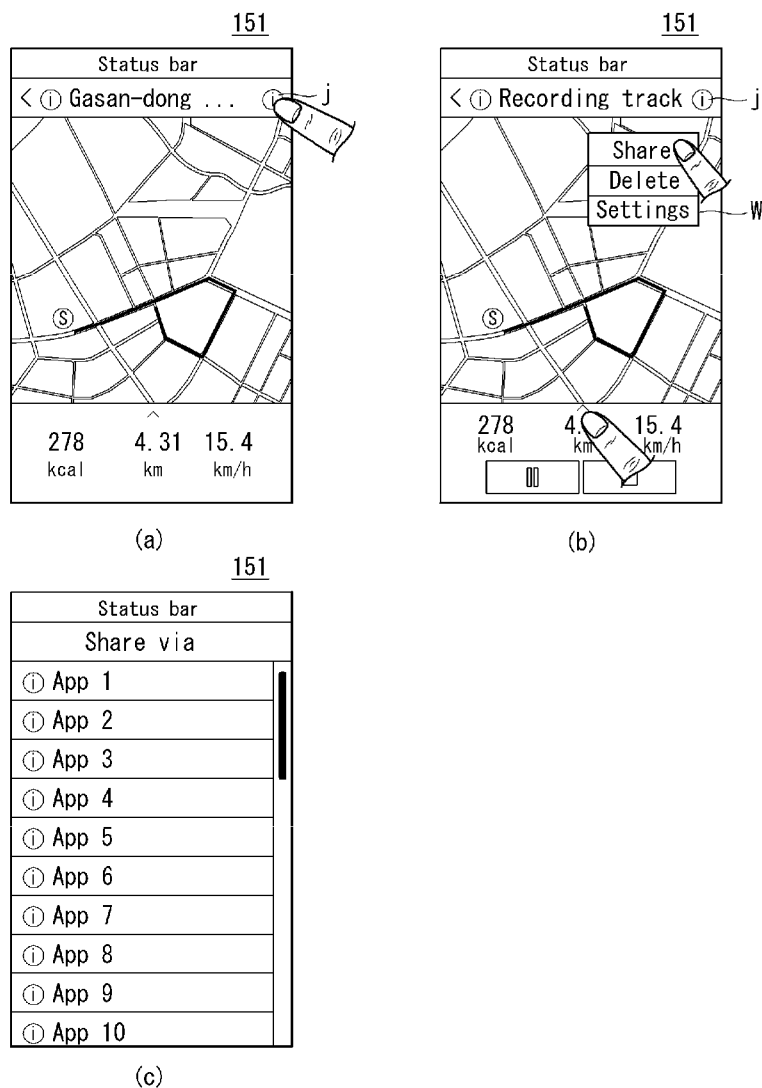

[Fig. 35]
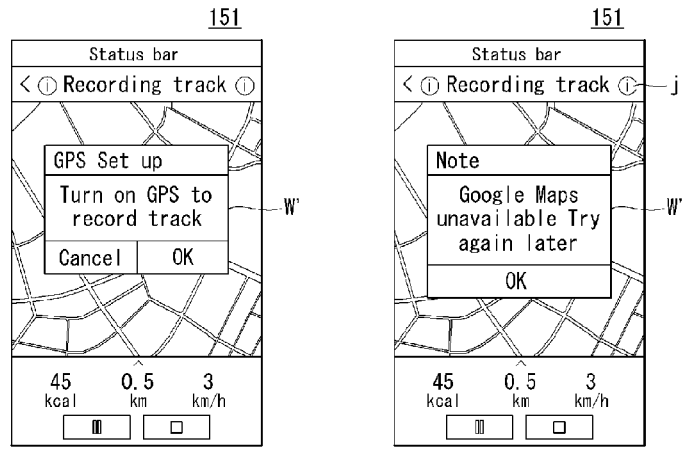
[Fig. 36]
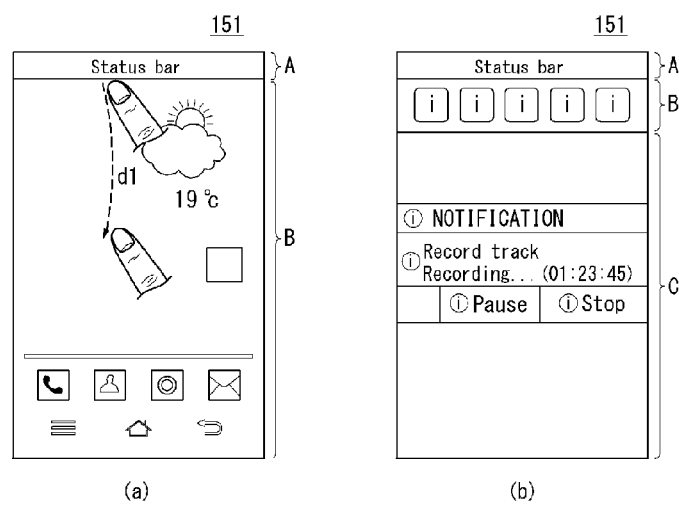

[Fig. 37]
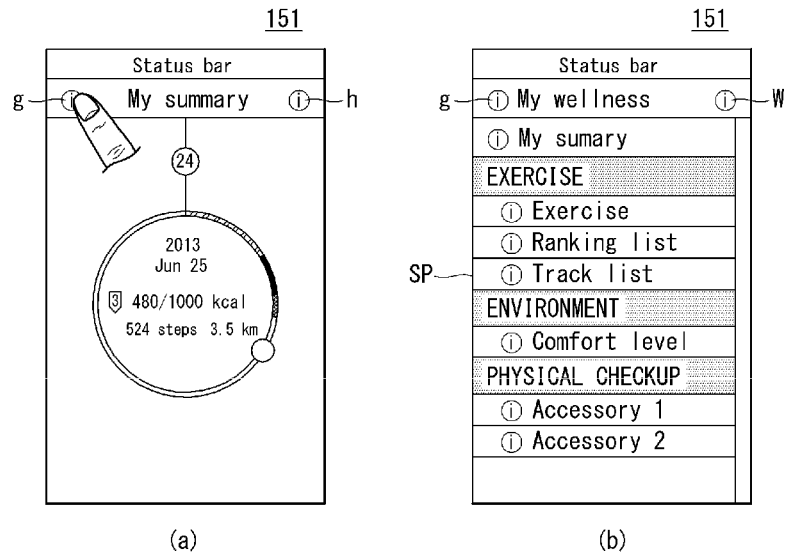
[Fig. 38]
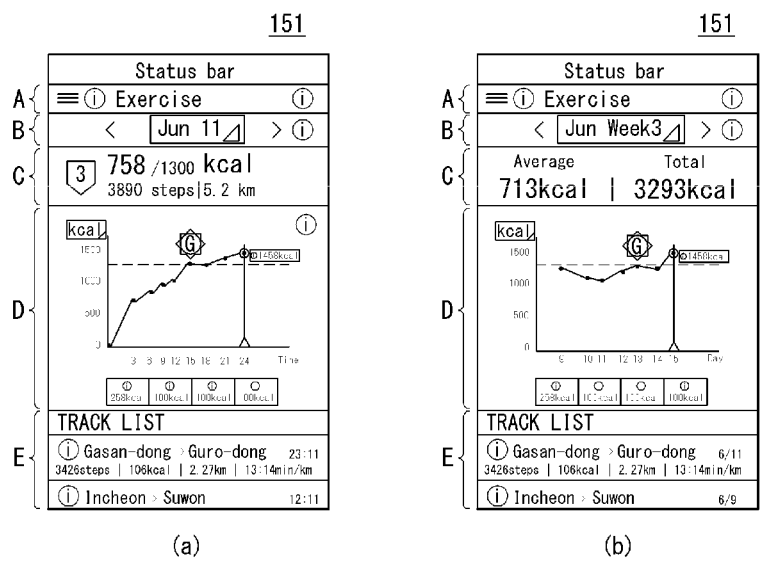

[Fig. 39]
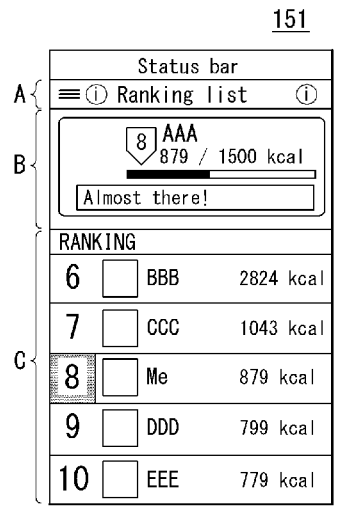
[Fig. 40]
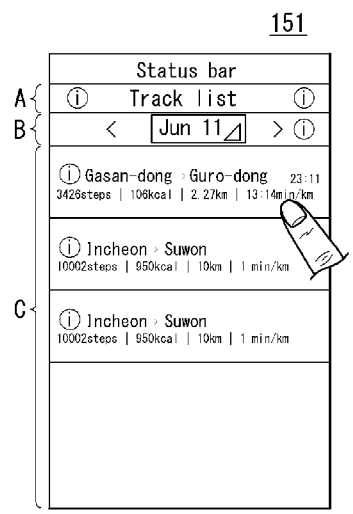 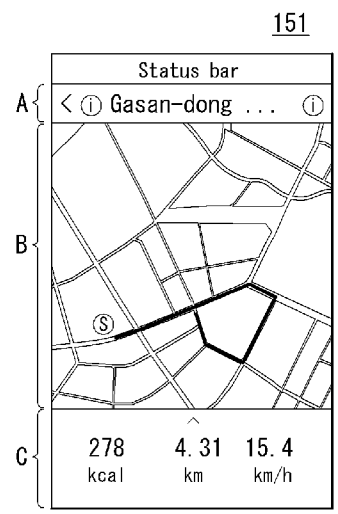
(a)          (b)

[Fig. 41]
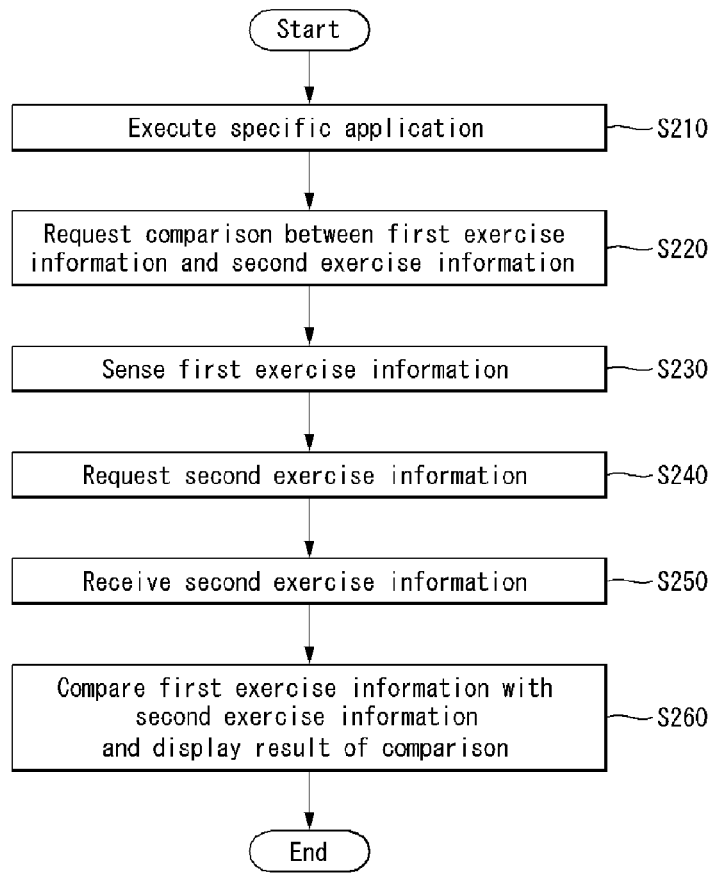
[Fig. 42]
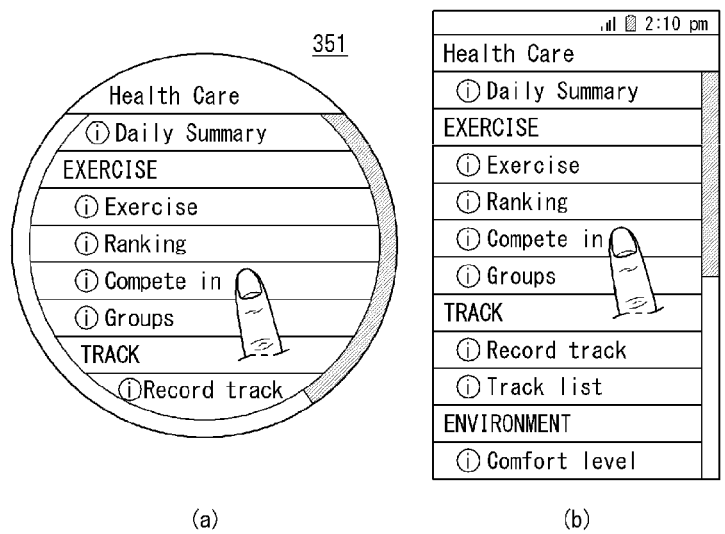
(a)　　　(b)

[Fig. 43]
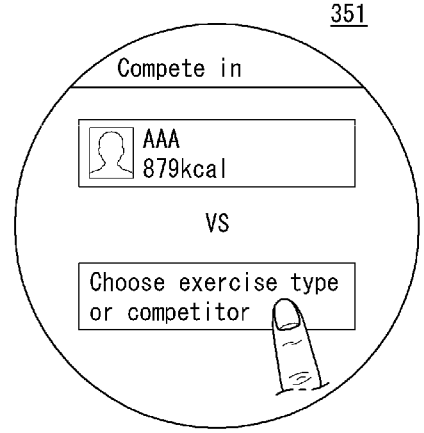
(a)
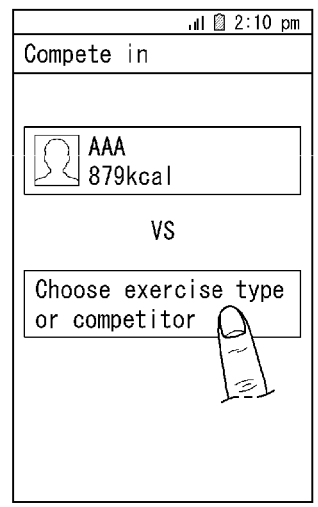
(b)
[Fig. 44]
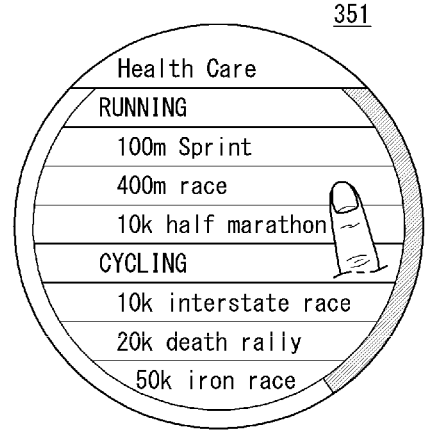
(a)
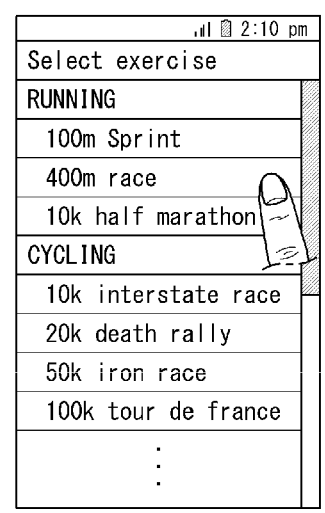
(b)

[Fig. 45]
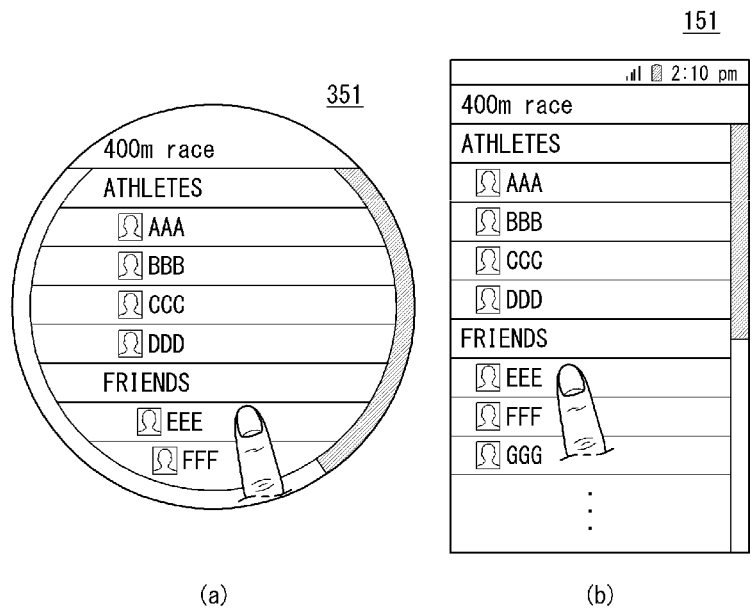
(a)          (b)
[Fig. 46]
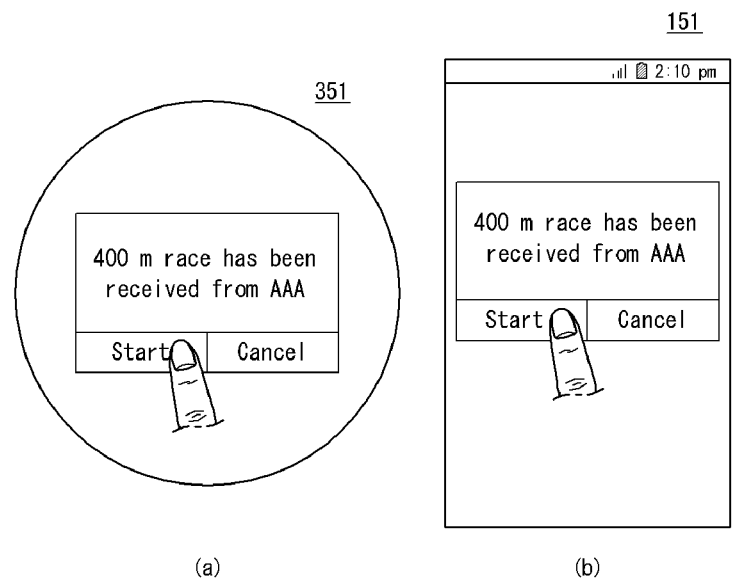
(a)          (b)

[Fig. 47]
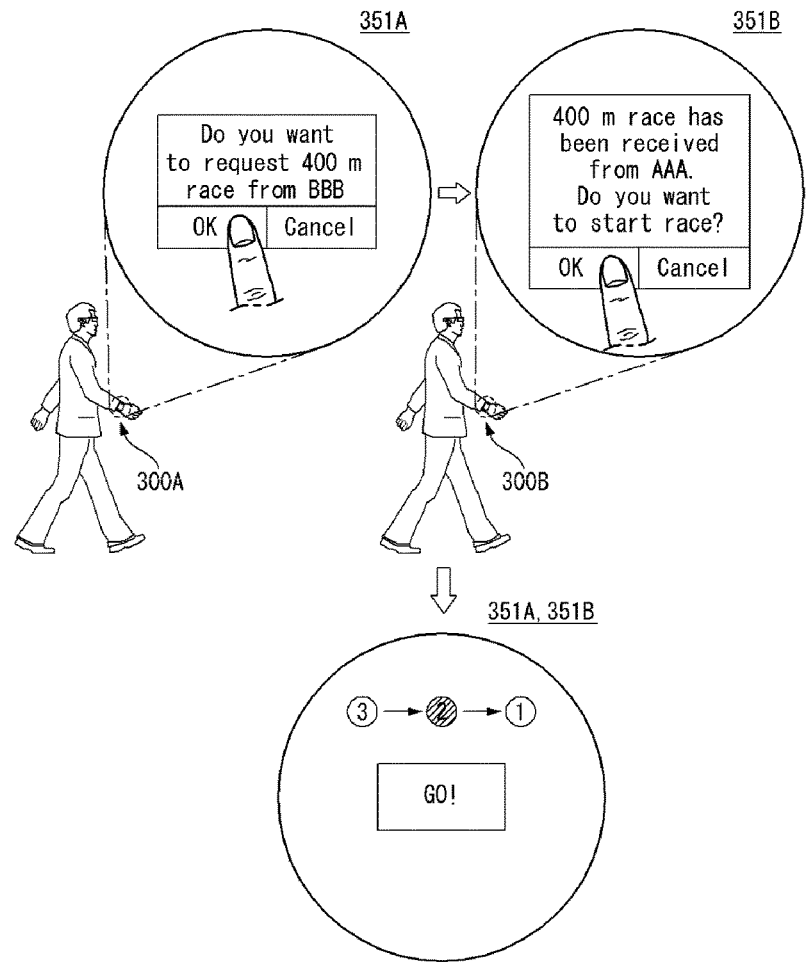
[Fig. 48]
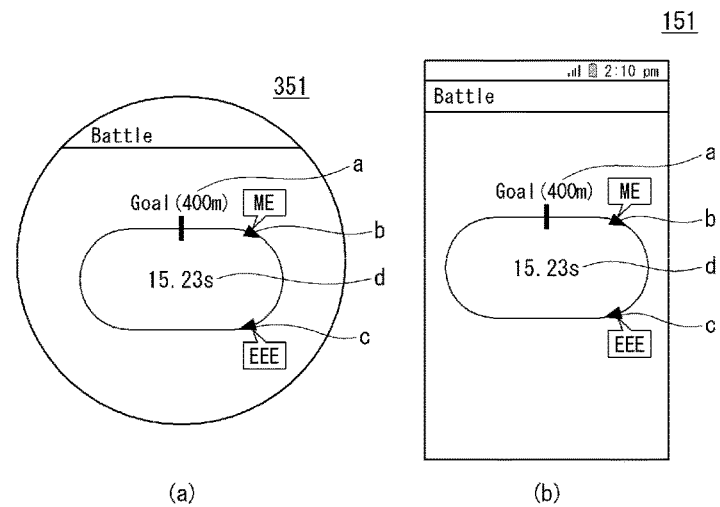

[Fig. 49]
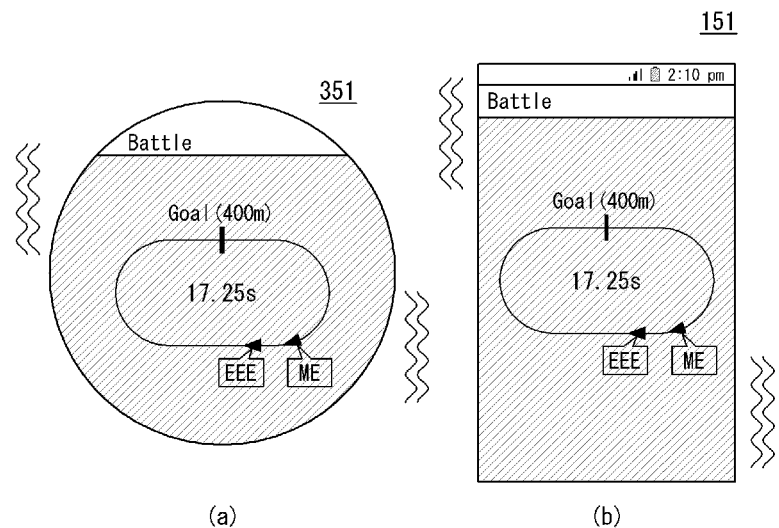
(a)  (b)
[Fig. 50]
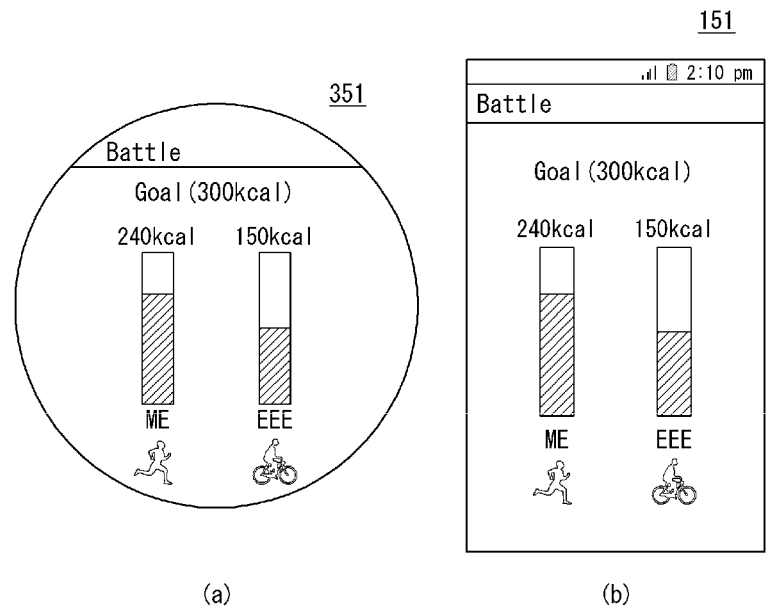
(a)  (b)

[Fig. 51]
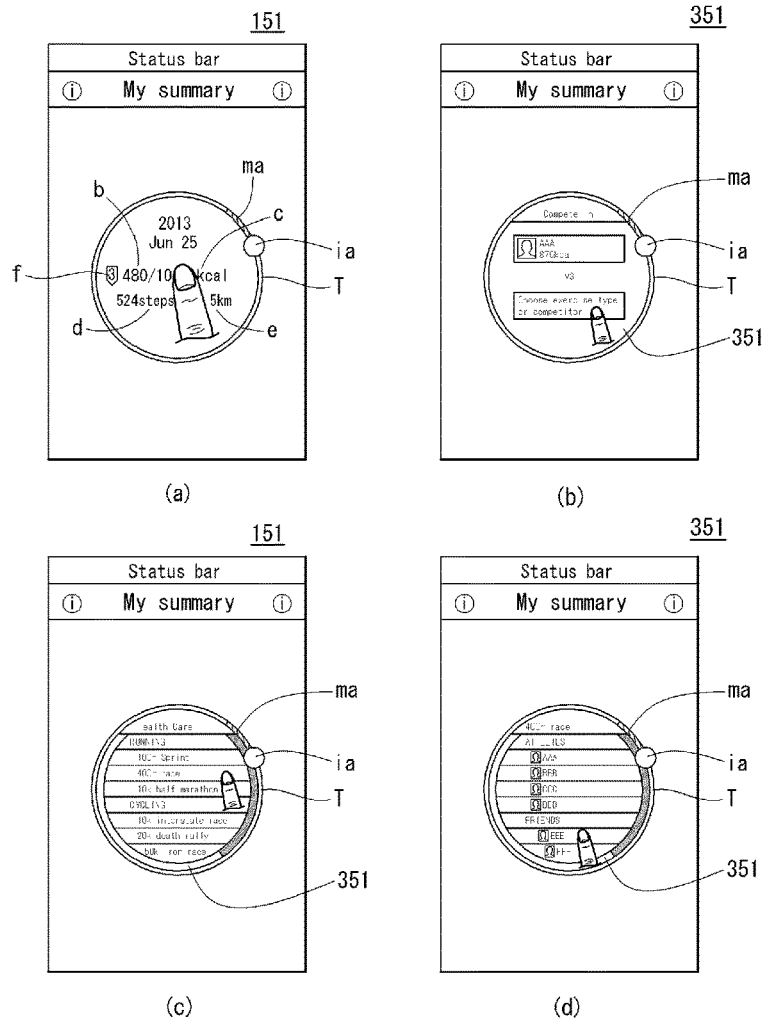
[Fig. 52]
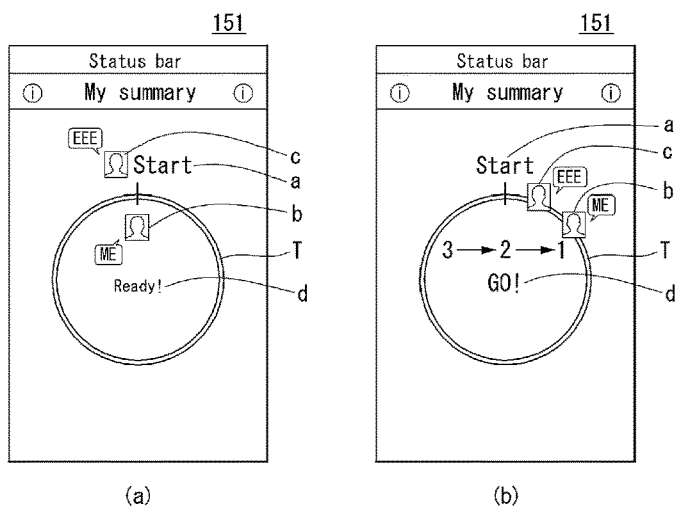

[Fig. 53]
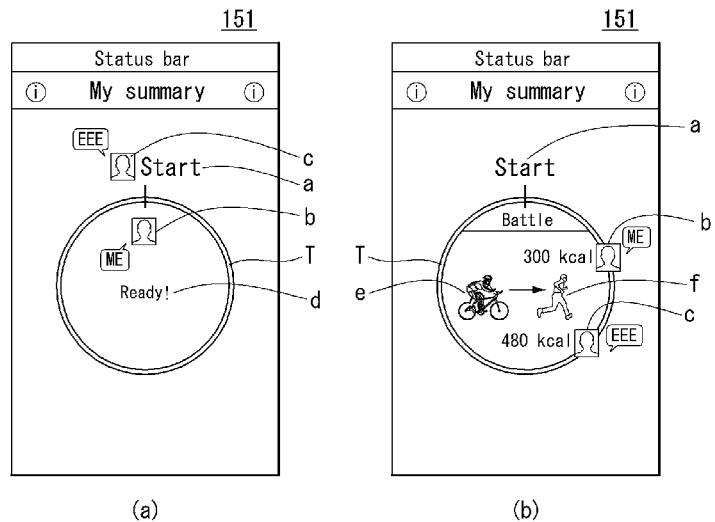
[Fig. 54]
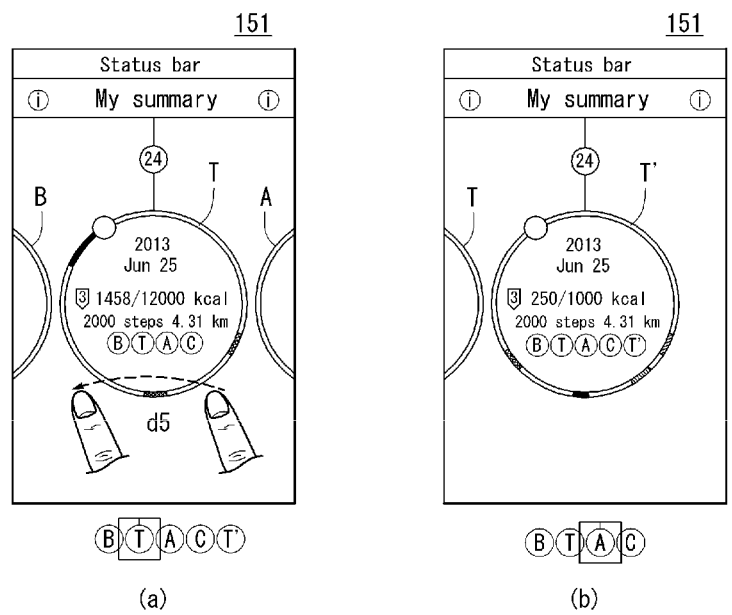

[Fig. 55]
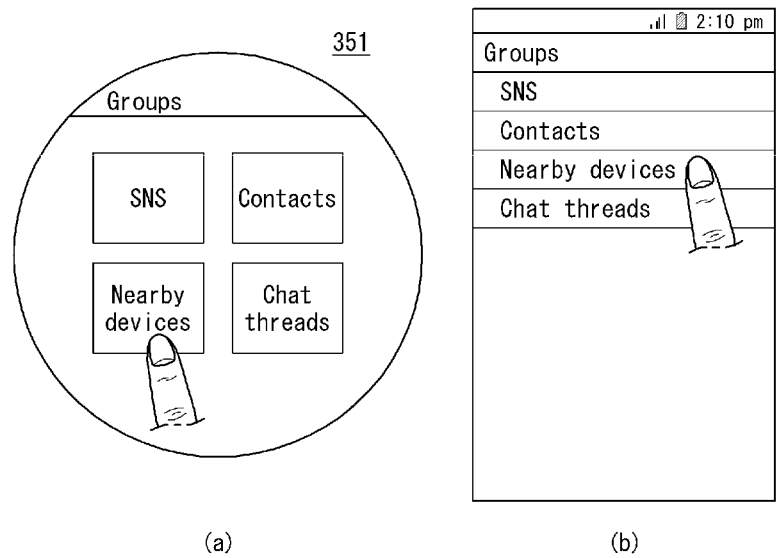
(a)　　　　　　　(b)
[Fig. 56]
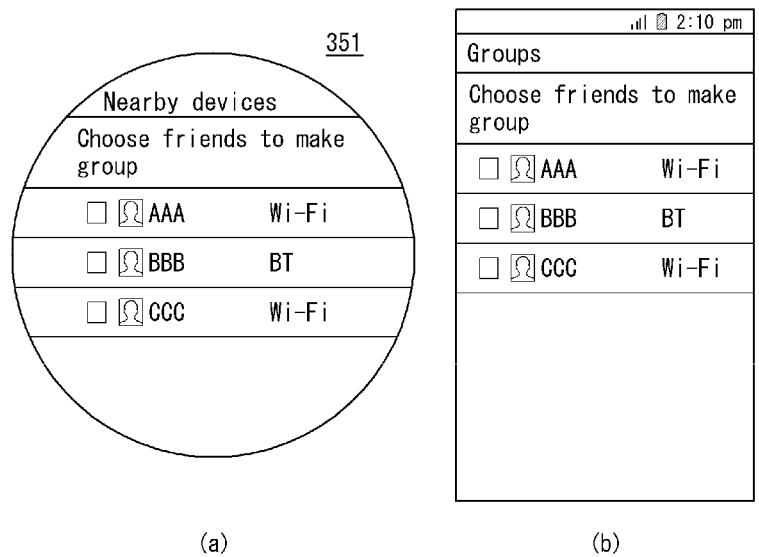
(a)　　　　　　　(b)

[Fig. 57]
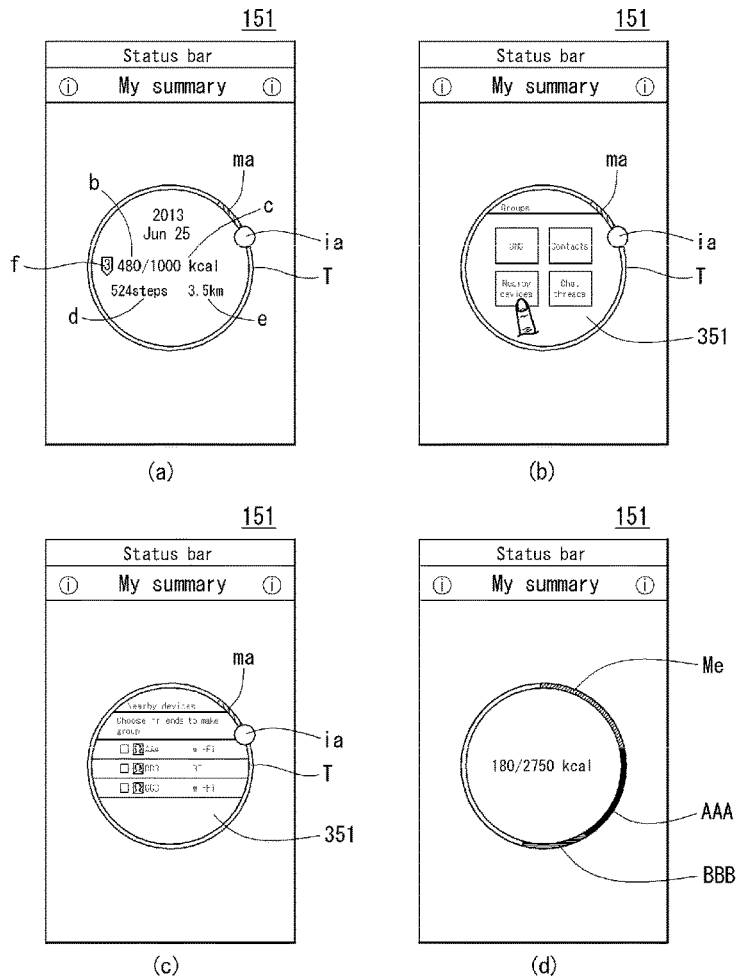
[Fig. 58]
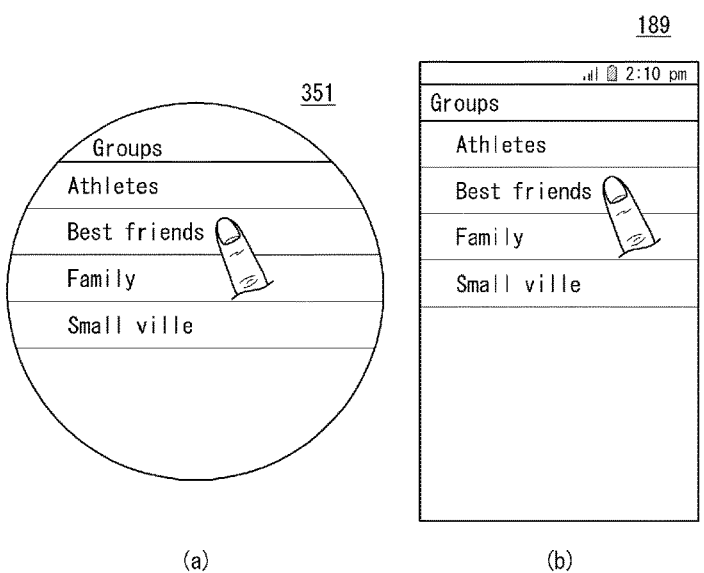

[Fig. 59]
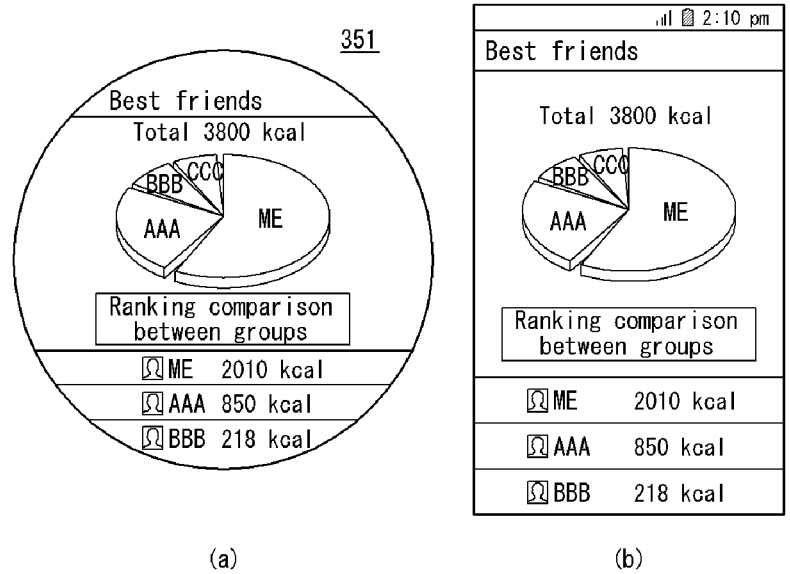
(a)　　　　　　　　(b)
[Fig. 60]
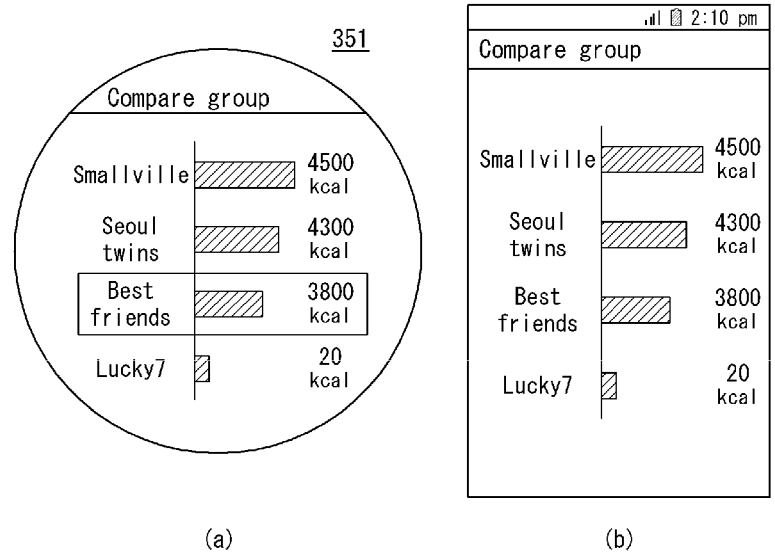
(a)　　　　　　　　(b)

[Fig. 61]
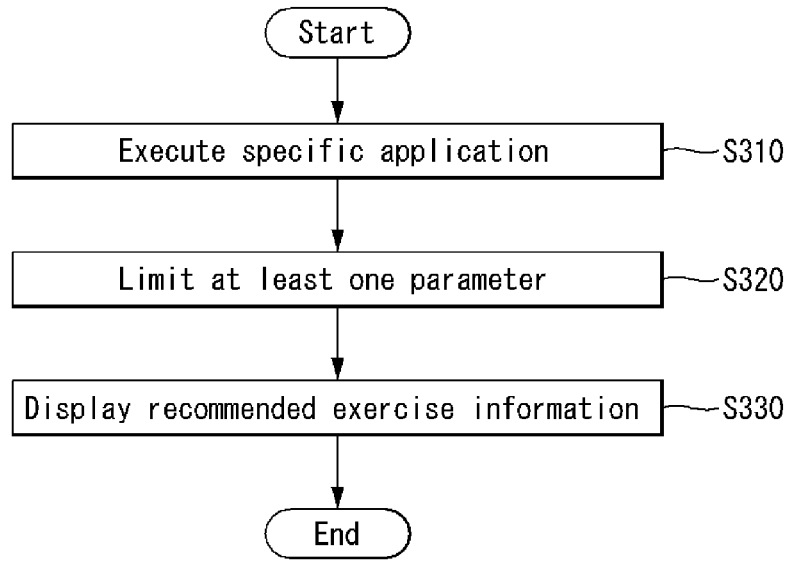
[Fig. 62]
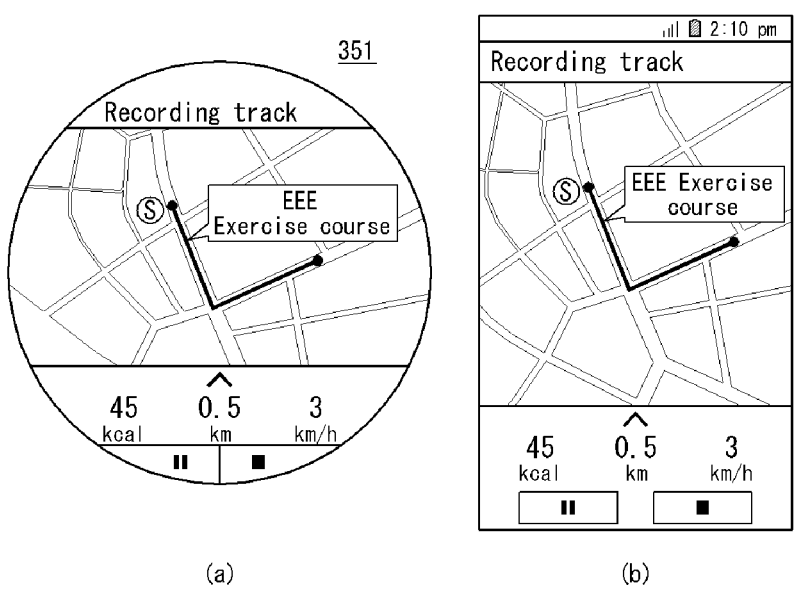

[Fig. 63]
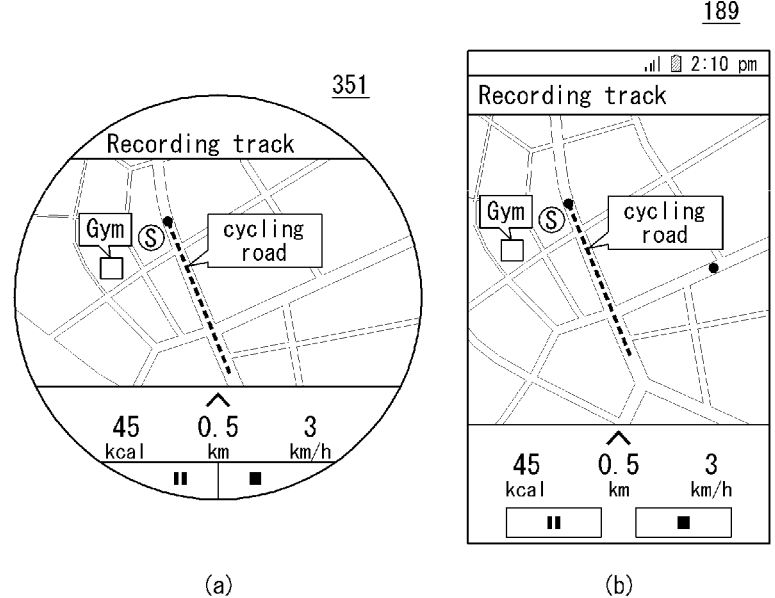
[Fig. 64]
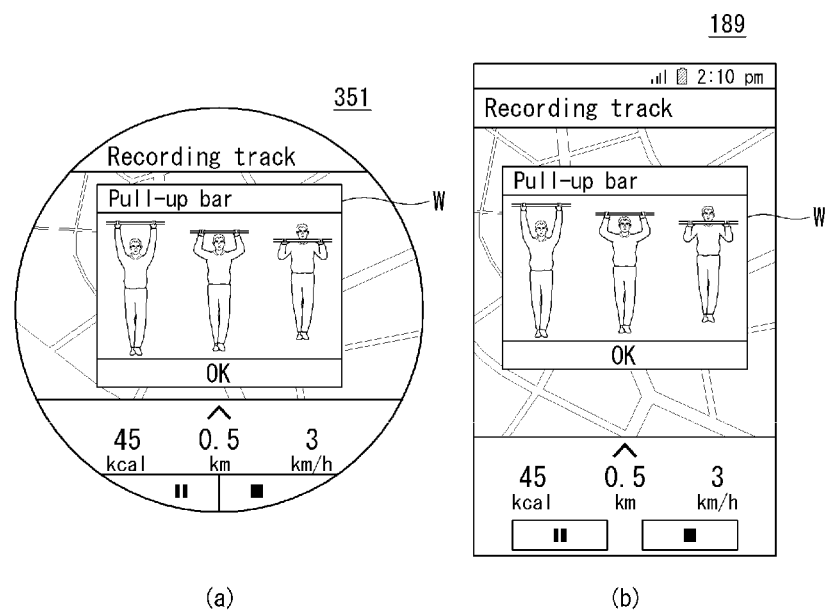

[Fig. 65]
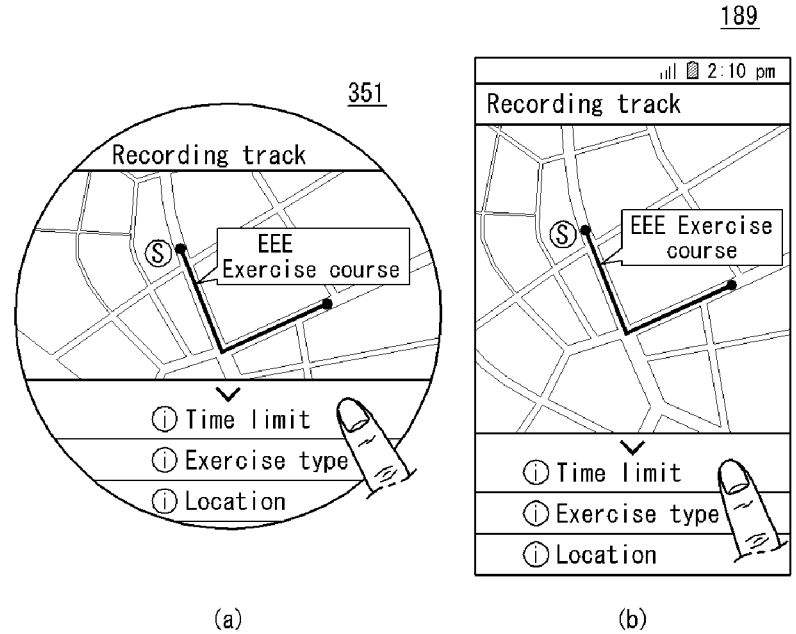
(a)　　　　　　　(b)
[Fig. 66]
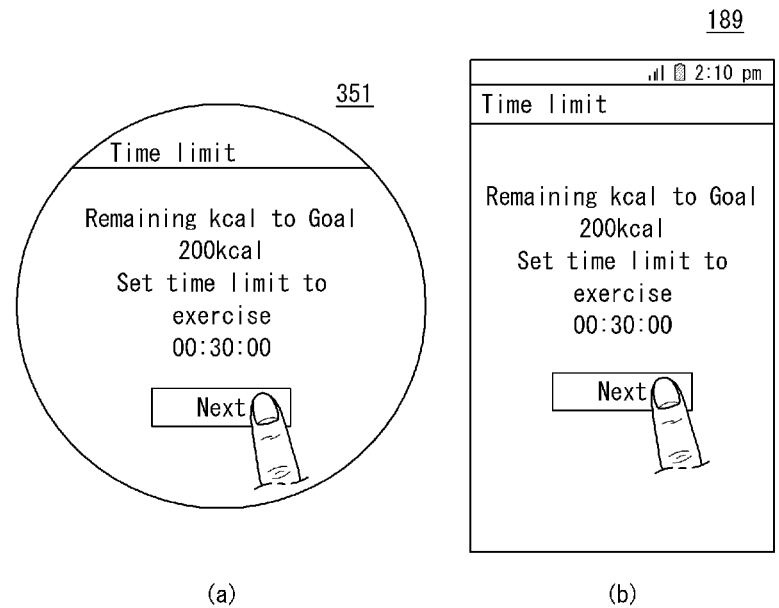
(a)　　　　　　　(b)

[Fig. 67]
(a)
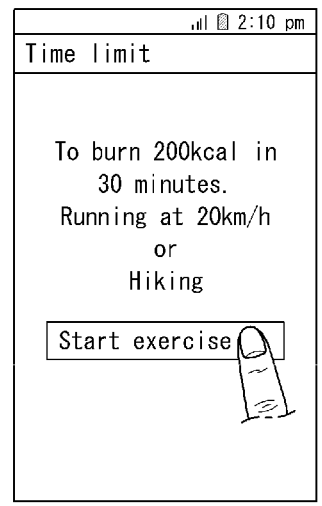
(b)
[Fig. 68]
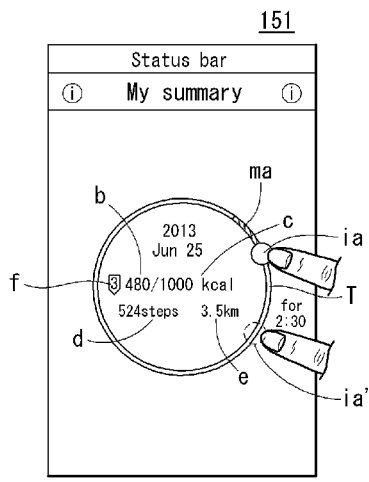
(a)
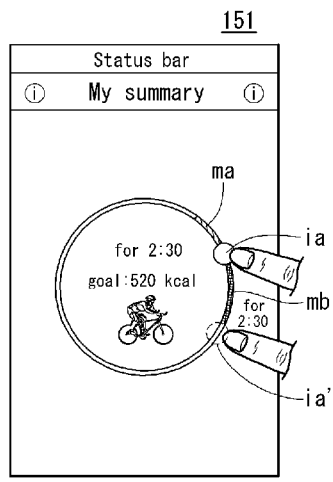
(b)

[Fig. 69]
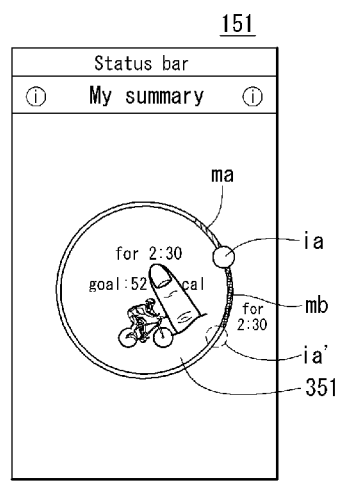
(a)
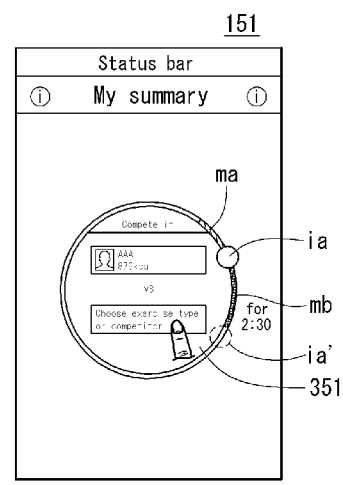
(b)
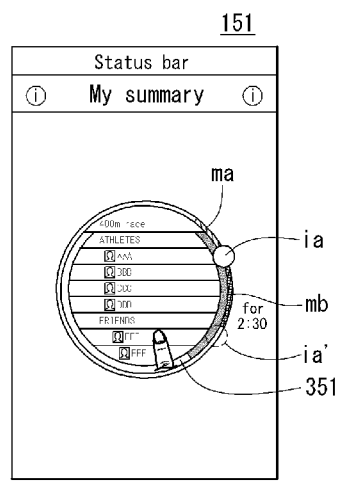
(c)
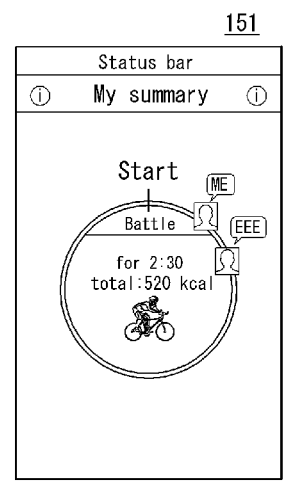
(d)

[Fig. 70]
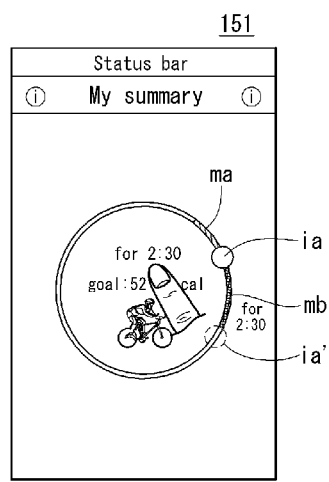
(a)
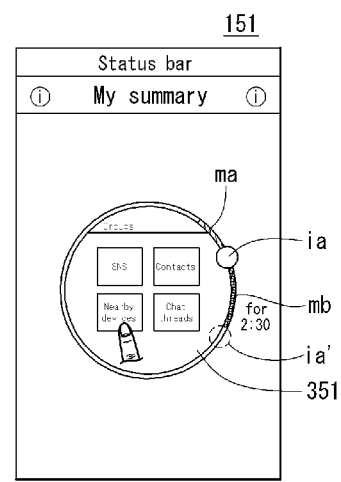
(b)
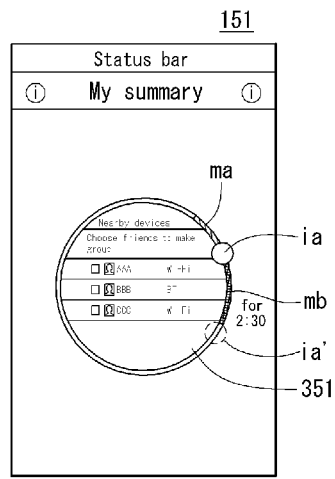
(c)
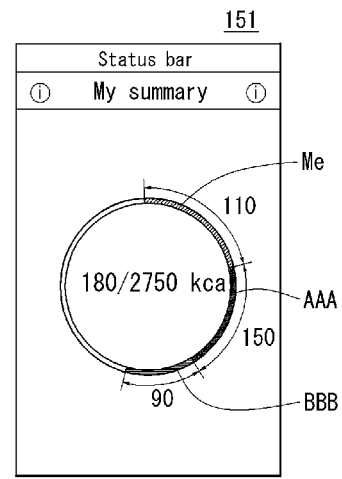
(d)

MOBILE TERMINAL AND METHOD FOR CONTROLLING THE SAME

CROSS-REFERENCE TO RELATED APPLICATIONS

This application is the National Phase of PCT International Application No. PCT/KR2014/009426, filed on Oct. 7, 2014, which claims priority under 35 U.S.C. 119(a) to Patent Application No. 10-2014-0042521, filed in the Republic of Korea on Apr. 9, 2014 and Patent Application No. 10-2014-0095043, filed in the Republic of Korea on Jul. 25, 2014, all of which are hereby expressly incorporated by reference into the present application.

BACKGROUND OF THE INVENTION

Field of the Invention

The present invention relates to a mobile terminal providing exercise information and a method for controlling the same.

Discussion of the Related Art

Terminals may be generally classified as mobile/portable terminals or stationary terminals according to their mobility. Mobile terminals may also be classified as handheld terminals or vehicle mounted terminals according to whether or not a user can directly carry the terminal.

Mobile terminals have become increasingly more functional. Examples of such functions include data and voice communications, capturing images and video through a camera, recording audio, playing music files through a speaker system, and displaying images and video on a display. Some mobile terminals include additional functionality which supports game playing, while other terminals are configured as multimedia players. More recently, mobile terminals have been configured to receive broadcast and multicast signals which permit viewing of content, such as videos and television programs.

Efforts are ongoing to support and increase the functionality of mobile terminals. Such efforts include software and hardware improvements, as well as changes and improvements in the structural components.

Recently, a terminal provides a multimedia service using sensing information sensed by a plurality of sensors embedded therein in order to perform composite functions.

In particular, search is attempted to provide a user interface including an element capable of calculating the exercise type and exercise distance of a user and exciting a user's interest using sensing information collected by a sensor for sensing a motion of a mobile terminal.

SUMMARY OF THE INVENTION

Accordingly, embodiments of the present invention are to address the above-described and other problems.

Effects of a mobile terminal and a method for controlling the same according to embodiments of the present invention are described below.

In accordance with at least one of the embodiments of the present invention, there is an advantage in that daily exercise information can be intuitively checked because the exercise type and exercise time of a user are displayed in a circular time line.

Furthermore, in accordance with at least one of the embodiments of the present invention, there are advantages in that various user exercise types can be converted into the number of steps and displayed and whether consumed calories, target calories, and location information have been stored can be checked using a single user interface.

Furthermore, in accordance with at least one of the embodiments of the present invention, there are advantages in that location information related to exercises can be additionally displayed in response to a user selection and information about the exercises of other users can be displayed in a list form.

Furthermore, in accordance with at least one of the embodiments of the present invention, there is an advantage in that exercise effects can be improved because a competition with another person is induced by providing exercise information about a group generated by a user, exercise information about a competitor, etc. together.

Furthermore, in accordance with at least one of the embodiments of the present invention, there is an advantage in that useful exercise information can be provided to a user by recommending an exercise type and exercise method most suitable for a user to the user based on the current location and condition information of the user.

To achieve these and other advantages and in accordance with the purpose of the present invention, as embodied and broadly described herein, the present invention provides in one aspect a mobile terminal, comprising: a sensing unit; a display unit; and a controller configured to display a first circular time line on the display unit when a specific application is executed and to display a motion of a user sensed by the sensing unit in the first circular time line in a tracking trajectory form in real time, wherein the tracking trajectory is displayed to have a different display characteristic based on a type of the sensed motion of the user.

A further scope of applicability of the present invention will become apparent from the detailed description given hereinafter. However, it should be understood that the detailed description and specific examples, while indicating preferred embodiments of the invention, are given by illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings, which are given by illustration only, and thus are not limitative of the present invention, and wherein:

FIG. 1a is a block diagram of a mobile terminal in accordance with the present disclosure.

FIGS. 1b to 1c are conceptual views of one example of the mobile terminal, viewed in different directions FIG. 2 is a conceptual view of a wearable mobile terminal according to an alternative embodiment of the present disclosure.

FIG. 3 is a conceptual view of a wearable mobile terminal according to another alternative embodiment of the present disclosure.

FIGS. 4 and 5 are flowcharts for illustrating an embodiment of a method for controlling a mobile terminal, which is related to the present invention.

FIGS. 6 to 40 are diagrams for illustrating an embodiment of a method for controlling a mobile terminal, which is related to the present invention.

FIG. 41 is a flowchart for illustrating another embodiment of a method for controlling a mobile terminal, which is related to the present invention.

FIGS. 42 to 60 are diagrams for illustrating another embodiment of a method for controlling a mobile terminal, which is related to the present invention.

FIG. 61 is a flowchart for illustrating yet another embodiment of a method for controlling a mobile terminal, which is related to the present invention.

FIGS. 62 to 70 are diagrams for illustrating yet another embodiment of a method for controlling a mobile terminal, which is related to the present invention.

DETAILED DESCRIPTION OF THE EMBODIMENTS

Description will now be given in detail in connection with exemplary embodiments disclosed herein, with reference to the accompanying drawings. For the sake of brief description with reference to the drawings, the same or equivalent components may be provided with the same reference numbers, and description thereof will not be repeated. In general, a suffix, such as "module" and "unit", may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As described above, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context. Terms, such as "include" or "have", are used herein and should be understood that they are intended to indicate an existence of several components, functions or steps, disclosed in the specification, and it is also understood that greater or fewer components, functions, or steps may likewise be utilized.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, and wearable devices (e.g., smart watches, smart glasses, and head mounted displays (HMDs)).

By way of non-limiting example only, further description will be made with reference to particular types of mobile terminals. However, such teachings apply equally to other types of terminals, such as those types described above. In addition, these teachings may also be applied to stationary terminals, such as digital TV, and desktop computers.

FIG. 1 is a block diagram of a mobile terminal in accordance with the present disclosure.

The mobile terminal 100 is shown having components, such as a wireless communication unit 110, an input unit 120, a sensing unit 140, an output unit 150, an interface unit 160, a memory 170, a controller 180, and a power supply unit 190. It is understood that implementing all of the illustrated components is not a requirement, and that greater or fewer components may alternatively be implemented.

Referring now to FIG. 1, the mobile terminal 100 is shown having wireless communication unit 110 configured with several commonly implemented components. For instance, the wireless communication unit 110 basically includes one or more components which permit wireless communication between the mobile terminal 100 and a wireless communication system or network within which the mobile terminal is located.

The wireless communication unit 110 basically includes one or more modules which permit communications, such as wireless communications between the mobile terminal 100 and a wireless communication system, communications between the mobile terminal 100 and another mobile terminal, communications between the mobile terminal 100 and an external server. Further, the wireless communication unit 110 basically includes one or more modules which connect the mobile terminal 100 to one or more networks. To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (e.g., a touch key, a push key, a mechanical key, and a soft key) for allowing a user to input information. Data (e.g., audio, video, and an image) is obtained by the input unit 120 and may be analyzed and processed by controller 180 according to device parameters, user commands, and combinations thereof.

The sensing unit 140 is basically implemented using one or more sensors configured to sense internal information of the mobile terminal, the surrounding environment of the mobile terminal, user information, and the like. For example, in FIG. 1, the sensing unit 140 is shown having a proximity sensor 141 and an illumination sensor 142.

If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (e.g., a camera 121), a microphone 122, a battery gauge, an environment sensor (e.g., a barometer, a hygrometer, a thermometer, a radiation detection sensor, a thermal sensor, and a gas sensor), and a chemical sensor (e.g., an electronic nose, a health care sensor, and a biometric sensor), to name a few. The mobile terminal 100 may be configured to utilize information obtained from sensing unit 140, and in particular, information obtained from one or more sensors of the sensing unit 140, and combinations thereof.

The output unit 150 is basically configured to output various types of information, such as audio, video, and tactile output. The output unit 150 is shown having a display unit 151, an audio output module 152, a haptic module 153, and an optical output module 154.

The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is basically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server through wireless communication. Other application programs may be installed within the mobile terminal 100 at time of manufacturing or shipping, which is basically the case for basic functions of the mobile terminal 100 (e.g., receiving a call, making a call, receiving a message, and sending a message). It is common for application programs to be stored in the memory 170, installed in the mobile terminal 100, and executed by the controller 180 to perform an operation (or function) for the mobile terminal 100.

The controller 180 basically functions to control overall operation of the mobile terminal 100, in addition to the operations associated with the application programs. The controller 180 may provide or process information or functions appropriate for a user by processing signals, data, information and the like, which are input or output by the various components depicted in FIG. 1, or activating application programs stored in the memory 170. For example, the controller 180 controls some or all of the components illustrated in FIGS. 1a to 1c according to the execution of an application program that have been stored in the memory 170.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

Referring to FIG. 1, various components depicted in this figure will now be described in more detail. Regarding the wireless communication unit 110, the broadcast receiving module 111 is basically configured to receive a broadcast signal and/or broadcast associated information from an external broadcast managing entity via a broadcast channel. The broadcast channel may include a satellite channel, a terrestrial channel or both. In some embodiments, two or more broadcast receiving modules 111 may be utilized to facilitate simultaneously receiving of two or more broadcast channels, or to support switching among broadcast channels.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (e.g., Global System for Mobile Communication (GSM), Code Division Multi Access (CDMA), Code Division Multi Access 2000 (CDMA2000), Enhanced Voice-Data Optimized or Enhanced Voice-Data Only (EV-DO), Wideband CDMA (WCDMA), High Speed Downlink Packet access (HSDPA), High Speed Uplink Packet Access (HSUPA), Long Term Evolution (LTE), and Long Term Evolution-Advanced (LTE-A)). Examples of wireless signals transmitted and/or received through the mobile communication module 112 include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals over communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), High Speed Uplink Packet Access (HSUPA), Long Term Evolution (LTE), Long Term Evolution-Advanced (LTE-A), and the like. The wireless Internet module 113 may transmit/receive data according to one or more of such wireless Internet technologies, and other Internet technologies as well.

In some embodiments, when the wireless Internet access is implemented according to WiBro, HSDPA, HSUPA, GSM, CDMA, WCDMA, LTE, or LTE-A, for example, as part of a mobile communication network, the wireless Internet module 113 performs such wireless Internet access. As described above, the Internet module 113 may operate in conjunction with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), and Wi-Fi Direct, a Wireless Universal Serial Bus (Wireless USB). In general, the short-range communication module 114 supports wireless communications between the mobile terminal 100 and a wireless communication system, communications between the mobile terminal 100 and another mobile terminal 100, or communications between the mobile terminal and a network where another mobile terminal 100 (or an external server) is located, over wireless area networks. An example of the wireless area networks is a wireless personal area network.

In some embodiments, another mobile terminal (which may be configured similarly to mobile terminal 100) may be a wearable device, for example, a smart watch, a smart glass or a head mounted display (HMD), which is able to exchange data with the mobile terminal 100 (or otherwise operate in conjunction with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of data processed in the mobile terminal 100 to the wearable device through the short-range communication module 114. Hence, a user of the wearable device may use the data processed in the mobile terminal 100 on the wearable device. For example, when a call is received in the mobile terminal 100, the user may answer the call using the wearable device. Furthermore, when a message is received in the mobile terminal 100, the user can check the received message using the wearable device.

The location information module 115 is generally configured to detect, calculate, derive or otherwise identify the position of the mobile terminal. For example, the location information module 115 includes a Global Position System (GPS) module, a Wi-Fi module or both. If desired, the location information module 115 may alternatively or additionally function with any of the other modules of the wireless communication unit 110 to obtain data related to the position of the mobile terminal.

For example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module.

The input unit 120 may be configured to permit various types of input to the mobile terminal 120. Examples of such input include audio, image, video, data, and user input. Image input and video input are often obtained using one or more cameras 121. Such cameras 121 may process image frames of still pictures or video obtained by image sensors in a video or image capture mode. The processed image frames can be displayed on the display unit 151 or stored in memory 170. In some cases, the cameras 121 may be arranged in a matrix form to permit a plurality of images having various angles or focal points to be input to the mobile terminal 100. As another example, the cameras 121 may be located in a stereoscopic arrangement to acquire left and right images for implementing a stereoscopic image.

The microphone 122 is generally implemented to permit audio input to the mobile terminal 100. The audio input can be processed in various manners according to a function being executed in the mobile terminal 100. If desired, the microphone 122 may include assorted noise removing algorithms to remove unwanted noise generated in the course of receiving the external audio.

The user input unit 123 is a component that permits input by a user. Such user input may enable the controller 180 to control operation of the mobile terminal 100. The user input unit 123 may include one or more of a mechanical input element (e.g., a key, a button located on a front and/or rear surface or a side surface of the mobile terminal 100, a dome switch, a jog wheel, and a jog switch), or a touch-sensitive input. For example, the touch-sensitive input may be a virtual key or a soft key, which is displayed on a touch screen through software processing, or a touch key which is located on the mobile terminal at a location that is other than the touch screen. On the other hand, the virtual key or the visual key may be displayed on the touch screen in various shapes, for example, graphic, text, icon, video, or a combination thereof.

The sensing unit 140 is generally configured to sense one or more of internal information about the mobile terminal, surrounding environment information about the mobile terminal, user information and so on. The controller 180 generally cooperates with the sending unit 140 to control operation of the mobile terminal 100 or execute data processing, a function or an operation associated with an application program installed in the mobile terminal based on the sensing provided by the sensing unit 140. The sensing unit 140 may be implemented using any of a variety of sensors, some of which will now be described in more detail.

The proximity sensor 141 may include a sensor to sense the presence or absence of an object that approaches a surface, or an object located near a surface, using an electromagnetic field, infrared rays or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 may sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be herein referred to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (e.g., a distance, the direction, speed, time, a position, and a moving state).

In general, controller 180 processes data corresponding to proximity touches and proximity touch patterns sensed by the proximity sensor 141, and cause output of visual information on the touch screen. In addition, the controller 180 can control the mobile terminal 100 to execute different operations or process different data according to whether a touch with respect to a point on the touch screen is either a proximity touch or a contact touch.

A touch sensor may sense a touch applied to a touch screen, such as the display unit 151, using any of a variety of touch methods. Examples of such a touch method include a resistive type, a capacitive type, an infrared type, and a magnetic field type.

For example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply touch input to the touch sensor. Examples of typical touch objects include a finger, a touch pen, a stylus pen, and a pointer.

When touch input is sensed by a touch sensor, corresponding signals may be transmitted to a touch controller. The touch controller may process the received signals, and then transmit corresponding data to the controller 180. Accordingly, the controller 180 may sense that which region of the display unit 151 has been touched. In this case, the touch controller may be a component separate from the controller 180, the controller 180 or a combination thereof.

In some embodiments, the controller 180 may execute the same or different control according to the type of touch object that touches the touch screen or a touch key provided in addition to the touch screen. Whether to execute the same or different control according to the object which provides touch input may be decided based on the current operating state of the mobile terminal 100 or a currently executed application program, for example.

The touch sensor and the proximity sensor may be implemented individually, or in combination, to sense various types of touches. Such a touch includes a short (or tap) touch, a long touch, a multi-touch, a drag touch, a flick touch, a pinch-in touch, a pinch-out touch, a swipe touch, and a hovering touch.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 basically includes at least one camera sensor (e.g., a CCD and CMOS), a photo sensor (or image sensors), and a laser sensor.

Implementing the camera 121 with a laser sensor may allow detection of a touch of a physical object with respect to a 3D stereoscopic image. The photo sensor may be laminated on, or overlapped with, the display device. The photo sensor may be configured to scan motion of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information about an application program that is executed in the mobile terminal 100 or user interface (UI) and graphic user interface (GUI) information in response to the execution screen information.

In some embodiments, the display unit 151 may be implemented as a stereoscopic display unit for displaying stereoscopic images. A typical stereoscopic display unit may use a stereoscopic display scheme, such as a stereoscopic scheme (glass scheme), an auto-stereoscopic scheme (glassless scheme) or a projection scheme (holographic scheme).

The audio output module 152 is generally configured to output audio data. Such audio data may be obtained from any of a number of different sources, such that the audio data may be received from the wireless communication unit 110 or may have been stored in the memory 170. The audio data may be output during mode, such as signal reception mode, call mode, record mode, voice recognition mode or broadcast reception mode. The audio output module 152 can provide audible output related to a particular function (e.g., a call signal reception sound and a message reception sound) performed by the mobile terminal 100. The audio output module 152 may also be implemented as a receiver, a speaker, a buzzer or the like.

A haptic module 153 may be configured to generate various tactile effects that a user feels, perceive, or otherwise experience. A typical example of a tactile effect generated by the haptic module 153 is vibration. The strength, pattern and the like of the vibration generated by the haptic module 153 may be controlled by user selection or setting by the controller. For example, the haptic module 153 may output different vibrations in a combining manner or a sequential manner.

Besides vibration, the haptic module 153 may generate various other tactile effects, including an effect by stimulation, such as a pin arrangement vertically moving to contact skin, a spray force or suction force of air through a jet orifice or a suction opening, a touch to the skin, a contact of an electrode, electrostatic force, and an effect by reproducing the sense of cold and warmth using an element that may absorb or generate heat.

The haptic module 153 may also be implemented to allow the user to feel a tactile effect through a muscle sensation, such as the user's fingers or arm, as well as transferring the tactile effect through direct contact. Two or more haptic modules 153 may be provided according to the particular configuration of the mobile terminal 100.

An optical output module 154 may output a signal for indicating event generation using the light of a light source. Examples of events generated in the mobile terminal 100 may include message reception, call signal reception, a missed call, an alarm, schedule notification, email reception, and information reception through an application.

Signal output by the optical output module 154 may be implemented in such a manner that the mobile terminal emits monochromatic light or light with a plurality of colors. The signal output may be terminated when the mobile terminal senses that a user has checked the generated event, for example.

The interface unit 160 serves as an interface for external devices to be connected with the mobile terminal 100. For example, the interface unit 160 may receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports and so on.

The identification module may be a chip that stores various types of information for authenticating the authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device may be connected with the terminal 100 through the interface unit 160.

When the mobile terminal 100 is connected with an external cradle, the interface unit 160 may serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 may store programs to support operations of the controller 180 and store input/output data (e.g., a phonebook, messages, still images, and video). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also operate in relation to a network storage device that performs the storage function of the memory 170 over a network, such as the Internet.

The controller 180 may basically control the general operations of the mobile terminal 100. For example, the controller 180 may set or release a lock state for restricting a user from inputting a control command with respect to applications when a status of the mobile terminal meets a preset condition.

The controller 180 may also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provides internal power and supplies appropriate power to operating elements and components included in the mobile terminal 100. The power supply unit 190 may include a battery, which is basically rechargeable or detachably coupled to the terminal body for charging.

The power supply unit 190 may include a connection port. The connection port may be configured as one example of the interface unit 160 to which an external charger for supplying power to recharge the battery is electrically connected.

For another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

Various embodiments described herein may be implemented in a computer-readable medium, a machine-readable medium, or similar medium using, for example, software, hardware, or any combination thereof.

Referring now to FIGS. 1b and 1c, the mobile terminal 100 is described with reference to a bar-type terminal body. However, the mobile terminal 100 may alternatively be implemented in any of a variety of different configurations. Examples of such configurations include watch-type, clip-type, glasses-type, or as a folder-type, flip-type, slide-type, swing-type, and swivel-type in which two and more bodies are combined with each other in a relatively movable manner, and combinations thereof. Discussion herein will often relate to a particular type of mobile terminal (e.g., a bar type, a watch type, or a glasses type). However, such teachings with regard to a particular type of mobile terminal will generally apply to other types of mobile terminals as well.

The mobile terminal 100 will basically include a casing (e.g., a frame, a housing or a cover) forming the appearance of the terminal. In this embodiment, the casing is formed using a front casing 101 and a rear casing 102. Various electronic components are incorporated into a space formed between the front casing 101 and the rear casing 102. At least one middle casing may be additionally positioned between the front casing 101 and the rear casing 102.

The display unit 151 is shown located on the front side of the terminal body to output information. As illustrated, a window 151a of the display unit 151 may be mounted on the front casing 101 to form the front surface of the terminal body together with the front casing 101.

In some embodiments, electronic components may also be mounted on the rear casing 102. Examples of such electronic components include a detachable battery 191, an identification module, a memory card, and the like. A rear cover 103 is shown covering the electronic components, and this cover may be detachably coupled to the rear casing 102. Therefore, when the rear cover 103 is detached from the rear casing 102, the electronic components mounted on the rear casing 102 are externally exposed.

As illustrated, when the rear cover 103 is coupled to the rear casing 102, a side surface of the rear casing 102 is partially exposed. In some cases, upon the coupling, the rear casing 102 may also be completely shielded by the rear cover 103. In some embodiments, the rear cover 103 may include an opening for externally exposing a camera 121b or an audio output module 152b.

The casings 101, 102, and 103 may be formed by injection-molding synthetic resin or may be made of metal, for example, stainless steel (STS), aluminum (Al) or titanium (Ti).

As an alternative to the example in which the plurality of casing form an inner space for accommodating components, the mobile terminal 100 may be configured such that one casing forms the inner space. In this example, a mobile terminal 100 having a uni-body is formed in such a manner that synthetic resin or metal extends from a side surface to a rear surface.

If desired, the mobile terminal 100 may include a waterproofing unit (not shown) for preventing introduction of water into the terminal body. For example, the waterproofing unit may include a waterproofing member which is located between the window 151a and the front casing 101, between the front casing 101 and the rear casing 102, or between the rear casing 102 and the rear cover 103, to hermetically seal an inner space when those cases are coupled.

FIGS. 1b and 1c depict certain components as arranged on the mobile terminal. However, it is to be understood that alternative arrangements are possible and within the teachings of the instant disclosure. Some components may be omitted or rearranged. For example, the first manipulation unit 123a may be located on another surface of the terminal body, and the second audio output module 152b may be located on the side surface of the terminal body.

The display unit 151 outputs information processed in the mobile terminal 100. The display unit 151 may be implemented using one or more suitable display devices. Examples of such suitable display devices include a liquid crystal display (LCD), a thin film transistor-liquid crystal display (TFT-LCD), an organic light emitting diode (OLED), a flexible display, a 3-dimensional (3D) display, an e-ink display, and combinations thereof.

The display unit 151 may be implemented using two display devices, which can implement the same or different display technology. For instance, a plurality of the display units 151 may be arranged on one side, either spaced apart from each other, or these devices may be integrated, or these devices may be arranged on different surfaces.

The display unit 151 may also include a touch sensor which senses touch input received at the display unit. When a touch is input to the display unit 151, the touch sensor may be configured to sense this touch and the controller 180, for example, may generate a control command or other signal corresponding to the touch. The content which is input in the touching manner may be a text or numerical value, or a menu item which can be indicated or designated in various modes.

The touch sensor may be configured in a form of a film having a touch pattern, disposed between the window 151a and a display on a rear surface of the window 151a, or a metal wire which is patterned directly on the rear surface of the window 151a. Alternatively, the touch sensor may be integrally formed with the display. For example, the touch sensor may be disposed on a substrate of the display or within the display.

The display unit 151 may also form a touch screen together with the touch sensor. In this case, the touch screen may serve as the user input unit 123 (see FIG. 1a). Therefore, the touch screen may replace at least some of the functions of the first manipulation unit 123a.

The first audio output module 152a may be implemented in the form of a speaker to output voice audio, alarm sounds, multimedia audio reproduction, and the like.

The window 151a of the display unit 151 will basically include an aperture to permit audio generated by the first audio output module 152a to pass. One alternative is to allow audio to be released along an assembly gap between the structural bodies (e.g., a gap between the window 151a and the front casing 101). In this case, a hole independently formed to output audio sounds may not be seen or is otherwise hidden in terms of appearance, thereby further simplifying the appearance and manufacturing of the mobile terminal 100.

The optical output module 154 may be configured to output light for indicating an event generation. Examples of such events include a message reception, a call signal reception, a missed call, an alarm, a schedule notice, an email reception, information reception through an application, and the like. When a user has checked a generated event, the controller may control the optical output unit 154 to stop the light output.

The first camera 121a may process image frames, such as still or moving images obtained by the image sensor in capture mode or video call mode. The processed image frames may then be displayed on the display unit 151 or stored in the memory 170.

The first and second manipulation units 123a and 123b are examples of the user input unit 123, which may be manipulated by a user to provide input to the mobile terminal 100. The first and second manipulation units 123a and 123b may also be commonly referred to as a manipulating portion, and may use any tactile method that allows the user to perform manipulations, such as a touch, push, and scroll. The first and second manipulation units 123a and 123b may also use any non-tactile method that allows the user to perform manipulations, such as proximity touch and hovering.

FIG. 1b illustrates the first manipulation unit 123a as a touch key, but possible alternatives include a mechanical key, a push key, a touch key, and combinations thereof.

Input received through the first and second manipulation units 123a and 123b may be used in various ways. For example, the first manipulation unit 123a may be used by the user to provide input to a menu, a home key, cancel, search or the like, and the second manipulation unit 123b may be used for a user to provide input that controls a volume level being output from the first or second audio output modules 152a or 152b and to switch to touch recognition mode of the display unit 151.

As another example of the user input unit 123, a rear input unit (not shown) may be located on the rear surface of the terminal body. The rear input unit can be manipulated by a user to provide input to the mobile terminal 100. The input may be used in a variety of different ways. For example, the rear input unit may be used by the user to provide an input for power on/off, start, end, scroll, control volume level being output from the first or second audio output module 152a or 152b, switch to a touch recognition mode of the display unit 151, and the like. The rear input unit may be configured to permit touch input, a push input, or combinations thereof.

The rear input unit may be located to overlap the display unit 151 of the front side in a thickness direction of the terminal body. For example, the rear input unit may be located on an upper end portion of the rear side of the terminal body such that a user may easily manipulate it using a forefinger when the user grabs the terminal body with one hand. Alternatively, the rear input unit may be positioned at any location of the rear side of the terminal body.

Embodiments that include the rear input unit may implement some or all of the functions of the first manipulation unit 123a in the rear input unit. As described above, in situations where the first manipulation unit 123a is omitted from the front side, the display unit 151 may have a larger screen.

As a further alternative, the mobile terminal 100 may include a finger scan sensor which scans a user's fingerprint. The controller 180 may then use fingerprint information sensed by the finger scan sensor as part of an authentication procedure. The finger scan sensor may also be installed on the display unit 151 or implemented in the user input unit 123.

The microphone 122 is shown located at an end of the mobile terminal 100, but other locations are possible. If desired, multiple microphones may be implemented, with such an arrangement permitting the receiving of stereo sounds.

The interface unit 160 may serve as a path allowing the mobile terminal 100 to interface with external devices. For example, the interface unit 160 may include one or more of a connection terminal for connecting to another device (e.g., an earphone or an external speaker), a port for near field communication (e.g., an Infrared Data Association (IrDA) port, a Bluetooth port or a wireless LAN port), or a power supply terminal for supplying power to the mobile terminal 100. The interface unit 160 may be implemented in the form of a socket for accommodating an external card, such as Subscriber Identification Module (SIM), User Identity Module (UIM), or a memory card for information storage.

The second camera 121b is shown located at the rear side of the terminal body and includes an image capturing direction that is substantially opposite to the image capturing direction of the first camera unit 121a. If desired, second camera 121a may alternatively be located at other locations, or made to be moveable, in order to have a different image capturing direction from that which is shown.

The second camera 121b may include a plurality of lenses arranged in at least one line. The plurality of lenses may also be arranged in a matrix form. The cameras may be referred to as an "array camera." When the second camera 121b is implemented as an array camera, images may be captured in various manners using the plurality of lenses and images with better qualities.

As shown in FIG. 1c, a flash 124 is shown adjacent to the second camera 121b. When an image of a subject is captured with the camera 121b, the flash 124 may illuminate the subject.

As shown in FIG. 1b, the second audio output module 152b may be located on the terminal body. The second audio output module 152b may implement stereophonic sound functions in conjunction with the first audio output module 152a, and may be also used for implementing a speaker phone mode for call communication.

At least one antenna for wireless communication may be located on the terminal body. The antenna may be installed in the terminal body or formed by the case. For example, an antenna which forms a part of the broadcast receiving module 111 may be retractable into the terminal body. Alternatively, an antenna may be formed using a film attached to an inner surface of the rear cover 103, or a case that includes a conductive material.

A power supply unit 190 for supplying power to the mobile terminal 100 may include a battery 191, which is mounted in the terminal body or detachably coupled to an outside of the terminal body. The battery 191 may receive power via a power source cable connected to the interface unit 160. Furthermore, the battery 191 can be recharged in a wireless manner using a wireless charger. Wireless charging may be implemented by magnetic induction or electromagnetic resonance.

The rear cover 103 is shown coupled to the rear casing 102 for shielding the battery 191, to prevent separation of the battery 191, and to protect the battery 191 from an external impact or from foreign material. When the battery 191 is detachable from the terminal body, the rear casing 103 may be detachably coupled to the rear casing 102.

An accessory for protecting an appearance or assisting or extending the functions of the mobile terminal 100 can also be provided on the mobile terminal 100. For example of an accessory, a cover or pouch for covering or accommodating at least one surface of the mobile terminal 100 may be provided. The cover or pouch may operate in conjunction with the display unit 151 to extend the function of the mobile terminal 100. Another example of the accessory is a touch pen for assisting or extending touch input to a touch screen.

In accordance with other embodiments, the mobile terminal may be configured as a device which is wearable on a human body. Such devices go beyond the usual technique of a user grasping the mobile terminal using their hand. Examples of the wearable device include a smart watch, a smart glass, and a head mounted display (HMD).

A typical wearable device can exchange data with (or operate in conjunction with) another mobile terminal 100. In such a device, the wearable device generally has functionality that is less than the cooperating mobile terminal. For example, the short-range communication module 114 of the mobile terminal 100 may sense or recognize a wearable device that is near-enough to communicate with the mobile terminal. In addition, when the sensed wearable device is a device which is authenticated to communicate with the mobile terminal 100, the controller 180 may transmit data processed in the mobile terminal 100 to the wearable device through the short-range communication module 114, for example. In this case, the user of the wearable device can use the data processed in the mobile terminal 100 on the wearable device. For example, when a call is received by the mobile terminal 100, the user can answer the call using the wearable device. Furthermore, when a message is received in the mobile terminal 100, the user can check the received message using the wearable device.

FIG. 2 is a perspective view illustrating one example of a watch-type mobile terminal 300 in accordance with another exemplary embodiment. As illustrated in FIG. 2, the watch-type mobile terminal 300 includes a main body 301 with a display unit 351 and a band 302 connected to the main body 301 to be wearable on a wrist. In general, mobile terminal 300 may be configured to include features that are the same or similar to that of mobile terminal 100 of FIGS. 1a to 1c.

The main body 301 may include a casing having a certain appearance. As illustrated, the casing may include a first casing 301a and a second casing 301b cooperatively defining an inner space for accommodating various electronic components. Other configurations are possible. For instance, a single casing may alternatively be implemented, with such a casing being configured to define the inner space, thereby implementing a mobile terminal 300 with a uni-body.

The watch-type mobile terminal 300 can perform wireless communication, and an antenna for the wireless communication can be installed in the main body 301. The antenna may extend its function using the case. For example, a case including a conductive material may be electrically connected to the antenna to extend a ground area or a radiation area.

The display unit 351 is shown located at the front side of the main body 301 so that displayed information is viewable to a user. In some embodiments, the display unit 351 includes a touch sensor so that the display unit can function as a touch screen. As illustrated, window 351a is positioned on the first casing 301a to form a front surface of the terminal body together with the first casing 301a.

The illustrated embodiment includes audio output module 352, a camera 321, a microphone 322, and a user input unit 323 positioned on the main body 301. When the display unit 351 is implemented as a touch screen, additional function keys may be minimized or eliminated. For example, when the touch screen is implemented, the user input unit 323 may be omitted.

The band 302 is commonly worn on the user's wrist and may be made of a flexible material for facilitating wearing of the device. For example, the band 302 may be made of fur, rubber, silicon, synthetic resin or the like. The band 302 may also be configured to be detachable from the main body 301. Accordingly, the band 302 may be replaceable with various types of bands according to a user's preference.

In one configuration, the band 302 may be used for extending the performance of the antenna. For example, the band may include therein a ground extending portion (not shown) electrically connected to the antenna to extend a ground area.

The band 302 may include fastener 302a. The fastener 302a may be implemented in a buckle type, a snap-fit hook structure, a Velcro® type or the like, and include a flexible section or material. The drawing illustrates an example that the fastener 302a is implemented using a buckle.

FIG. 3 is a perspective view illustrating one example of a glass-type mobile terminal 400 according to another exemplary embodiment. The glass-type mobile terminal 400 may be wearable on a head of a human body and provided with a frame (or a casing or a housing) therefor. The frame may be made of a flexible material to be easily worn. The frame of mobile terminal 400 is shown having a first frame 401 and a second frame 402, which may be made of the same or different materials. In general, mobile terminal 400 may be configured to include features that are the same or similar to that of mobile terminal 100 of FIGS. 1a to 1c.

The frame may be supported on the head and defines a space for mounting various components. As illustrated, electronic components, such as a control module 480 and an audio output module 452, may be mounted on the frame part. Furthermore, a lens 403 for covering either or both of the left and right eyes may be detachably coupled to the frame part.

The control module 480 controls various electronic components disposed in the mobile terminal 400. The control module 480 may be understood as a component corresponding to the aforementioned controller 180. FIG. 3 illustrates that the control module 480 is installed in the frame part on one side of the head, but other locations are possible.

The display unit 451 may be implemented as a head mounted display (HMD). The HMD refers to a display technique in which a display is mounted on a head to show an image directly in front of a user's eyes. In order to provide an image directly in front of the user's eyes when the user wears the glass-type mobile terminal 400, the display unit 451 may be located to correspond to either or both of the left and right eyes. FIG. 3 illustrates that the display unit 451 is located on a portion corresponding to the right eye to output an image viewable by the user's right eye.

The display unit 451 may project an image onto the user's eye using a prism. Furthermore, the prism may be made of an optically transparent material such that the user may view both a projected image and a general visual field (a range that the user views through the eyes) in front of the user.

In such a manner, the image output through the display unit 451 may be viewed while overlapping with the general visual field. The mobile terminal 400 may provide an augmented reality (AR) by overlaying a virtual image on a realistic image or background using the display.

The camera 421 may be located adjacent to either or both of the left and right eyes to capture an image. Since the camera 421 is located adjacent to an eye, the camera 421 may acquire a scene that the user is currently viewing. The camera 421 may be positioned at most any location of the mobile terminal. In some embodiments, multiple cameras 421 may be utilized. Such multiple cameras 421 may be used to acquire a stereoscopic image.

The glass-type mobile terminal 400 may include user input units 423a and 423b, which may each be manipulated by the user to provide an input. The user input units 423a and 423b may use techniques which permit input through tactile input. Typical tactile inputs include a touch, push and so on. The user input units 423a and 423b are shown to be operable in a pushing manner and a touching manner as they are located on the frame part and the control module 480, respectively.

If desired, the mobile terminal 400 may include a microphone which processes input sound into electric audio data, and an audio output module 452 for outputting audio. The audio output module 452 may be configured to produce audio in a general audio output manner or an osteoconductive manner. When the audio output module 452 is implemented in the osteoconductive manner, the audio output module 452 may be closely adhered to the head when the user wears the mobile terminal 400 and vibrate the user's skull to transfer sounds.

The location information module 115 is generally configured to detect, calculate, or otherwise identify a position of the mobile terminal. For example, the location information module 115 may include a Global Position System (GPS) module, a Wi-Fi module, or both. If desired, the location information module 115 may alternatively or additionally function with any of the other modules of the wireless communication unit 110 to obtain data related to the position of the mobile terminal.

A typical GPS module 115 may measure an accurate time and distance from three or more satellites, and accurately calculate a current location of the mobile terminal according to trigonometry based on the measured time and distances. A method of acquiring distance and time information from three satellites and performing error correction with a single satellite may be used. In particular, the GPS module may acquire an accurate time together with three-dimensional speed information as well as the location of the latitude, longitude and altitude values from the location information received from the satellites.

Furthermore, the GPS module may acquire speed information in real time to calculate the current location. Sometimes, accuracy of a measured position may be compromised when the mobile terminal is located in a blind spot of satellite signals, such as being located in an indoor space. In order to minimize the effect of such blind spots, an alternative or supplemental location technique, such as Wi-Fi Positioning System (WPS), may be utilized.

The Wi-Fi positioning system (WPS) refers to a location determination technology based on a wireless local area network (WLAN) using Wi-Fi as a technology for tracking the location of the mobile terminal 100. This technology basically includes the use of a Wi-Fi module in the mobile terminal 100 and a wireless access point for communicating with the Wi-Fi module.

The Wi-Fi positioning system may include a Wi-Fi location determination server, a mobile terminal, a wireless access point (AP) connected to the mobile terminal, and a database stored with wireless AP information.

The mobile terminal connected to the wireless AP may transmit a location information request message to the Wi-Fi location determination server. The Wi-Fi location determination server extracts the information of the wireless AP connected to the mobile terminal 100, based on the location information request message (or signal) of the mobile terminal 100. The information of the wireless AP may be transmitted to the Wi-Fi location determination server through the mobile terminal 100, or may be transmitted to the Wi-Fi location determination server from the wireless AP.

The information of the wireless AP extracted based on the location information request message of the mobile terminal 100 may include one or more of media access control (MAC) address, service set identification (SSID), received signal strength indicator (RSSI), reference signal received Power (RSRP), reference signal received quality (RSRQ), channel information, privacy, network type, signal strength, noise strength, and the like.

The Wi-Fi location determination server may receive the information of the wireless AP connected to the mobile terminal 100 as described above, and may extract wireless AP information corresponding to the wireless AP connected to the mobile terminal from the pre-established database.

The information of any wireless APs stored in the database may be information, such as a MAC address, an SSID, RSSI, channel information, privacy, a network type, latitude and longitude coordinates, a building at which a wireless AP is located, a floor number, detailed indoor location information (GPS coordinates available), an AP owner's address, and a phone number. In order to remove wireless APs provided using a mobile AP or an illegal MAC address during a location determining process, the Wi-Fi location determination server may extract only a predetermined number of wireless AP information in order of high RSSI.

Then, the Wi-Fi location determination server may extract (analyze) location information of the mobile terminal 100 using at least one wireless AP information extracted from the database.

A method for extracting (or analyzing) location information about the mobile terminal 100 may include a Cell-ID method, a fingerprint method, a trigonometry method, a landmark method, and the like.

The Cell-ID method is used to determine a position of a wireless AP having the largest signal strength, among peripheral wireless AP information collected by a mobile terminal, as a position of the mobile terminal. The Cell-ID method is an implementation that is minimally complex, does not require additional costs, and location information can be rapidly acquired. However, in the Cell-ID method, the precision of positioning may fall below a desired threshold when the installation density of wireless APs is low.

The fingerprint method is used to collect signal strength information by selecting a reference position from a service area, and to track a position of a mobile terminal using the signal strength information transmitted from the mobile terminal based on the collected information. In order to use the fingerprint method, it is common for the characteristics of radio signals to be pre-stored in the form of a database.

The trigonometry method is used to calculate the position of a mobile terminal based on the distance between the coordinates of at least three wireless APs and the mobile terminal. In order to measure the distance between the mobile terminal and the wireless APs, signal strength may be converted into distance information, Time of Arrival (ToA), Time Difference of Arrival (TDoA), and Angle of Arrival (AoA) may be taken for transmitted wireless signals.

The landmark method is used to measure the position of a mobile terminal using a known landmark transmitter.

In addition to these position location methods, various algorithms may be used to extract (analyze) location information about a mobile terminal. Such extracted location information may be transmitted to the mobile terminal 100 through the Wi-Fi location determination server, thereby acquiring location information of the mobile terminal 100.

The mobile terminal 100 may acquire location information by being connected to at least one wireless AP. The number of wireless APs required to acquire location information of the mobile terminal 100 may be variously changed according to a wireless communication environment within which the mobile terminal 100 is positioned.

As previously described with regard to FIG. 1a, the mobile terminal may be configured to include short-range communication techniques, such as Bluetooth™, Radio Frequency Identification (RFID), Infrared Data Association (IrDA), Ultra Wideband (UWB), ZigBee, Near Field Communication (NFC), and Wireless USB (Wireless Universal Serial Bus).

A typical NFC module provided at the mobile terminal supports short-range wireless communication, which is a non-contactable type of communication between mobile terminals and generally occurs within about 10 cm. The NFC module may operate in one of a card mode, a reader mode, or a P2P mode. The mobile terminal 100 may further include a security module for storing card information, in order to operate the NFC module in a card mode. The security module may be a physical medium, such as a Universal Integrated Circuit Card (UICC) (e.g., a Subscriber Identification Module (SIM) or a Universal SIM (USIM)), a secure micro SD and a sticker or a logical medium (e.g., an embedded Secure Element (SE)) embedded in the mobile terminal. Single Wire Protocol (SWP)-based data exchange may be performed between the NFC module and the security module.

In a case where the NFC module operates in a card mode, the mobile terminal may transmit card information on a general IC card to the outside. More specifically, if a mobile terminal having card information on a payment card (e. g, a credit card or a bus card) approaches a card reader, a short-range mobile payment may be executed. As another example, if a mobile terminal which stores card information on an entrance card approaches an entrance card reader, an entrance approval procedure may start. A card, such as a credit card, a traffic card or an entrance card, may be included in the security module in the form of applet, and the security module may store card information on the card mounted therein. Card information about a payment card may include any of a card number, the remaining amount and a usage history. Card information about an entrance card may include any of a user's name, a user's number (e.g., an undergraduate number or a staff number), an entrance history, and the like.

When the NFC module operates in a reader mode, the mobile terminal can read data from an external tag. The data received from the external tag by the mobile terminal may be coded into the NFC Data Exchange Format defined by the NFC Forum. The NFC Forum generally defines four record types. More specifically, the NFC Forum defines four Record Type Definitions (RTDs), such as a smart poster, text, a Uniform Resource Identifier (URI), and general control. If the data received from the external tag is a smart poster type, the controller may execute a browser (e.g., an Internet browser). If the data received from the external tag is a text type, the controller may execute a text viewer. If the data received from the external tag is a URI type, the controller may execute a browser or originate a call. If the data received from the external tag is a general control type, the controller may execute a proper operation according to control content.

In some cases in which the NFC module operates in Peer-to-Peer (P2P) mode, the mobile terminal can execute P2P communication with another mobile terminal. In this case, Logical Link Control Protocol (LLCP) may be applied to the P2P communication. For P2P communication, connection may be generated between the mobile terminal and another mobile terminal. This connection may be categorized as a connectionless mode which ends after one packet is switched, and a connection-oriented mode in which packets are switched consecutively. For typical P2P communication, data, such as an electronic type name card, address information, a digital photo, and a URL, a setup parameter for Bluetooth connection, Wi-Fi connection, etc. may be converted. P2P mode can be effectively utilized in switching data of a small capacity, because an available distance for NFC communication is relatively short.

Further preferred embodiments will be described in more detail with reference to additional drawing figures. It is understood by those skilled in the art that the present features can be embodied in several forms without departing from the characteristics thereof.

Hereinafter, detailed embodiments of the present invention are described.

FIGS. 4 and 5 are flowcharts for illustrating an embodiment of a method for controlling the mobile terminal, which is related to the present invention. FIGS. 6 to 40 are diagrams for illustrating an embodiment of a method for controlling the mobile terminal, which is related to the present invention. Hereinafter, a "user" refers to a user who carries a terminal on himself or herself, and a motion of a user may be used as the same meaning as a motion of the mobile terminal.

Referring to FIG. 4, the controller (180 of FIG. 1*a*) of the mobile terminal may execute a specific application (S110), and may display a circular time line on the display unit (151 of FIG. 1*a*) (S130).

The specific application refers to an application program which provides information related to the exercises of a user using a motion of the mobile terminal, which has been sensed by the sensing unit (140 of FIG. 1*a*) embedded in the mobile terminal. When the specific application is executed, the controller may display 24 hours in the circular time line.

The controller (180 of FIG. 1*a*) may sense a motion of a user over time (S150), and may display a tracking trajectory in the circular time line in real time (S170).

Specifically, the controller may analyze the moving distance, direction, speed, type, and consumed calories of the user by analyzing sensing information sensed by a 9-axis sensor including an acceleration sensor, a gyro sensor, and a geomagnetic sensor. The controller may display information about the analyzed motion of the user in the circular time line, may update changed motion information as a motion of the user changes in real time, and may display the updated information. Furthermore, the controller may accumulate and display user motion information during 24 hours in the circular time line.

Referring to FIG. 5, the controller (180 of FIG. 1*a*) of the mobile terminal may classify the motion of the user for each type using the sensing information sensed by the sensing unit (140 of FIG. 1*a*) (S172).

The controller may always set the location information module in an on state in an execution screen of the specific application so that a motion of a user is classified for each type. In this case, the controller may classify a motion of the user for each type although the specific application is not executed. In contrast, if the location information module has been set to maintain an on state only when the specific application is executed, the controller may classify a motion of a user for each type only when the specific application is executed. In addition, the controller may set the location information module so that it is turned on when the quantity of motion of the user sensed by the sensing unit is a reference value or more.

The controller may classify a motion type of the user as one of a plurality of set types. In this case, the controller may determine the motion type by synthesizing location information collected by the location information module and the sensing information sensed by a plurality of sensors included in the sensing unit.

Specifically, the controller may classify the motion type of the user based on the moving distance, moving speed, and moving direction of the user (i.e., a change of the location information).

For example, if a motion of a user is a transverse direction and the user moves at first speed or less, a motion type of the user may be classified as "walking." If a motion of a user is a transverse direction and the user moves at speed which exceeds the first speed and is second speed or less, a motion type of the user may be classified as "run." If a motion of a user is a transverse direction and the user moves at speed which exceeds the second speed and is third speed or less, a motion type of the user may be classified as "cycling." Furthermore, if a motion of a user is a transverse direction and the user moves at speed more than the third speed, the controller may analyze that the user moves using another transportation means and may not display a tracking trajectory in the circular time line. Accordingly, the controller may not display a tracking trajectory in the circular time line if a motion not related to exercise is analyzed in addition to the case where a motion of a user is not sensed.

Furthermore, if a motion of a user is a vertical direction and the user moves at the first speed or less, the controller may classify a motion type of the user as "mountain climbing." In addition, the controller may determine a classification criterion using a moving distance and moving speed in the longitudinal direction and transverse direction of a motion of a user, and may classify a motion type of the user as "walking", "run", "cycling", "mountain climbing", or "inline skating".

In addition, the controller may subdivide an exercise type of a user using sensing information obtained from a motion sensor. The controller may display the exercise type of the user on the display unit using an indicator including a character, symbol or figure indicative of a specific exercise type. When the exercise type of the user is changed, the controller may output at least one of visual feedback, auditory feedback, and tactile feedback.

The controller (180 of FIG. 1*a*) may display a tracking trajectory so that it has a different display characteristic depending on the classified motion type of the user (S174). In this case, the display characteristic may include the color, thickness of the line, and pattern of the corresponding tracking trajectory.

When a motion of a user is intermittently sensed, the controller may perform control so that a tracking trajectory is displayed in a time interval only in the circular time line in which the motion of the user is sensed, but the tracking trajectory is not displayed in a time interval in which the motion of the user is not sensed.

The controller may also display information about the number of steps, moving distance, target calories, and consumed calories of the user in the circular time line. In this case, the target calories may be determined by taking into consideration an inputted age, height, current weight, and target weight of the user.

The controller may convert the quantity of motion into the number of steps depending on a motion type of the user, and may display the number of steps.

The controller may display a specific indicator on a portion of the circular time line corresponding to the present time, may move the specific indicator over time, and may display the moved specific indicator. When input to the specific indicator is received, the controller may display the present time in a number form.

The controller (180 of FIG. 1*a*) may store the history of the tracking trajectories of previous or next dates in the memory (170 of FIG. 1*a*). The controller may sequentially display the histories of the previous or next dates using indicators of a bead form, and may differently display the indicator of a date that belongs to the history of previous or next dates and on which target calories have been achieved in a highlighted form.

When flicking input to a screen on which indicators of a bead form have been displayed is received, the controller may move the locations of the indicators of a bead form in response to the flicking input.

Furthermore, the controller may enlarge the tracking trajectory of a date corresponding to a specific indicator that belongs to indicators of a bead form moved in response to flicking input and that has been disposed at a set location, and may display the enlarged tracking trajectory on the display unit. That is, the controller may display a tracking trajectory displayed in the circular time line of a date corresponding to the specific indicator, disposed at the set location, on the entire screen.

Furthermore, when pinch-in input to a specific indicator of indicators of a bead form is received, the controller may enlarge the display region of the specific indicator, and may display the tracking trajectory of a date corresponding to the specific indicator in the enlarged display region. When pinch-out input to the tracking trajectory of the date corresponding to the specific indicator is received, the controller may reduce the enlarged display region to a previous size and display the specific indicator.

The controller (180 of FIG. 1*a*) may perform pairing with at least one accessory, and may display at least part of a circular time line indicative of the paired accessory on the display unit (151 of FIG. 1*a*). In this case, a circular time line that displays exercise information obtained through the mobile terminal may be defined as a first circular time line, and a circular time line that displays exercise information obtained through the paired accessory may be defined as a second circular time line.

The controller may display the first circular time line at the center of a screen, and may sequentially display at least part of the second circular time line on the left or right of the first circular time line according to the pairing sequence of at least one accessory. In this case, the controller may display an indicator indicative of the number of paired accessories within the first circular time line. The controller may change display from the first circular time line to the second circular time line through left or right flicking input, and may move the display location of the first circular time line or another second circular time line displayed on the left or right of the second circular time line in response to the flicking input. The controller may synchronize sensing information received from a paired accessory, may display the synchronized sensing information on the second circular time line, but may display a synchronization time on the second circular time line.

When specific input is received through the display unit (151 of FIG. 1*a*), the controller (180 of FIG. 1*a*) may store location information along with a tracking trajectory in response to a motion of a user, and may display a location information recording trajectory inside or outside the tracking trajectory corresponding to a time interval in which the location information has been stored. In this case, the controller may determine whether a GPS module is an on state, and may determine whether or not to turn on the GPS module if the GPS module is an off state.

The controller may additionally display a map on which location information has been displayed in response to a motion of a user and a user interface, including a moving distance, moving speed, and consumed calories corresponding to a time interval in which the location information has been stored. The user interface may be displayed over a screen on which a circular time line has been displayed in the form of a sliding screen or a pop-up screen.

The controller (180 of FIG. 1*a*) may receive the tracking information of another user who shares a tracking trajectory, may arrange the received tracking information, and may display the arranged tracking information in a list form.

FIGS. 6 to 40 are drawings for illustrating a method for displaying exercise information including an exercise type of a user in the mobile terminal according to an embodiment of the present invention.

FIGS. 6 to 9 are drawings for illustrating a method for displaying the tracking trajectory of a user sensed in the mobile terminal, which is related to an embodiment of the present invention.

Referring to FIG. 6, the controller (180 of FIG. 1*a*) of the mobile terminal may execute a specific application Ic when it receives input to the specific application Ic which provides information related to the exercises of a user using a motion of the mobile terminal.

When the specific application is executed, the controller may display menu icons "g" and "h" and a circular time line T, and may display at least one piece of information of a current date "a", consumed calories "b", target calories "c", the number of steps "d", and a moving distance "e" within the circular time line T. Furthermore, the controller may display a specific indicator "ia", corresponding to the present time, in the circular time line T. The controller may rotate and display the location of the specific indicator "ia" displayed in the circular time line T clockwise over time.

Referring to FIG. 7, the controller (180 of FIG. 1*a*) of the mobile terminal may display 24 hours in the circular time line. The controller may display the 24 hours every two hours in the circular time line.

The controller may display tracking trajectories "ma", "mb", and "mc" in the circular time line T in real time, and may display the specific indicator "ia", corresponding to the present time, in the circular time line T. The specific indicator "ia" moves in the circular time line T clockwise over time in proportion to time that elapses.

The controller may classify a motion type of a user using sensing information sensed by the sensing unit of the mobile terminal up to the present time, and may display the tracking trajectories "ma", "mb", and "mc" so that they have different display characteristics depending on a motion type of the user. For example, the controller may differently display hatching of the tracking trajectories "ma", "mb", and "me" or display the tracking trajectories "ma", "mb", and "mc" with different colors depending on a motion type of the user.

The controller may display at least one of the current date "a", the consumed calories "b", the target calories "c", the number of steps "d" of the user, and the moving distance "e", and the number of dates "f" on which a tracking trajectory has been obtained within the circular time line T, and may display the menus "g" and "h" above the display unit.

Referring to FIG. 8, the controller (180 of FIG. 1*a*) of the mobile terminal may display a tracking trajectory having a different display characteristic when a motion type of a user who owns a terminal is changed over time.

Referring to FIG. 8(*a*), when a motion of a user is not sensed from 00:00 a.m. to a first point of time at which the specific indicator "ia" has been displayed, the controller may not display a tracking trajectory in the circular time line T, and may display the consumed calories "b", the number of steps "d" of the user, and the moving distance "e" as "0" within the circular time line T.

Referring to FIG. 8(*b*), when the user "runs from the first point of time to a second point of time, the controller may display the first tracking trajectory "ma" between the first point of time and the second point of time in the circular time line T, may calculate the consumed calories "b", the number of steps "d" of the user, and the moving distance "e" from the first point of time to the second point of time, and may display the calculated information within the circular time line T.

Referring to FIG. 8(c), when the user "steps on stairs" from the second point of time to a third point of time, the controller may display the second tracking trajectory "mb" between the second point of time and the third point of time in the circular time line T, may accumulate the consumed calories "b", the number of steps "d" of the user, and the moving distance "e" from the second point of time to the third point of time, and may display the accumulated information within the circular time line T. That is, the controller may display the total sums of the consumed calories "b", the number of steps "d" of the user, and the moving distance "e" up to the third point of time within the circular time line T.

Referring to FIG. 8(d), when the user does not move from the third point of time to a fourth point of time, the controller may not display a tracking trajectory between the third point of time and the fourth point of time in the circular time line T (md).

Referring to FIG. 9, the controller (180 of FIG. 1a) of the mobile terminal may display a highlighted specific indicator ia' when target calories are achieved at a specific point of time.

When a user starts to run from a first point of time, the controller may display a first tracking trajectory having a display characteristic, corresponding to the "run" type, from the first point of time (refer to FIG. 9(b)). When set target calories are achieved, the controller may highlight and display the specific indicator "ia" indicative of the present time.

If the mobile terminal is a watch phone, the controller may change a user interface so that it corresponds to a form of the display unit 351 of the watch phone, and may display the changed user interface. For example, the controller may configure the edge of a circular display unit 351 using a circular time line T, and may display a menu name (e.g., My summary), date information (e.g., 2013 Jun. 25), and exercise information (e.g., 480/1000 Kcal, 524 steps, and 3.5 km) within the circular time line T (refer to FIG. 9(d)).

FIGS. 10 to 18 are diagrams for illustrating a method for displaying the history of tracking trajectories of a user, which has been sensed in the mobile terminal related to an embodiment of the present invention.

Referring to FIG. 10, if the history of tracking trajectories of previous or next dates has been stored, the controller (180 of FIG. 1a) of the mobile terminal may sequentially display the tracking histories of the previous or next dates on the display unit (151 of FIG. 1a) using indicators of a bead form.

Referring to FIG. 10(a), if the history of tracking trajectories of previous or next dates has not been stored, the controller may display only the circular time line T of the current date (e.g., 2013 Jun. 25).

Referring to FIG. 10(b), if the histories of tracking trajectories of previous dates have been stored, the controller may display the tracking histories using indicators I1 and I2 of a bead form, and may display the number "f" indicating that the tracking history of the current date (e.g., 2013 Jun. 25) corresponds to what day. The controller may display corresponding dates within the indicators I1 and I2 of a bead form.

Referring to FIG. 10(c), the controller may display the circular time line T of a specific date (e.g., 2013 Jun. 25) at the center of the display unit, and may display the tracking history of previous or next dates using indicators I1, I2, I4, and I5 of a bead form.

Referring to FIG. 10(d), if the mobile terminal is a watch phone, the controller may change a user interface so that it corresponds to a form of the display unit 351 of the watch phone, and may display the changed user interface.

For example, the controller may display the tracking history of previous or next dates using the indicators I1, I2, I4, and I5 of a bead form within a circular display unit 351, and may display the tracking history of a today's date in the circular time line T.

The controller may configure the edge of the circular display unit 351 using the circular time line T, and may display the menu name (e.g., My summary), date information (e.g., 2013 Jun. 25), and exercise information (e.g., 480/1000 Kcal, 524 steps, and 3.5 km) within the circular time line T.

If the indicators I1, I2, I4, and I5 corresponding to the tracking history of a date anterior or posterior to a specific date (e.g., 2013 Jun. 25) has been displayed at the center of the display unit, the controller may further display an icon "k" where a tracking trajectory corresponding to the current date may be displayed at the center of the display unit on one side of the display unit.

Referring to FIG. 11, if the tracking history of a previous or next date has been stored in the memory (170 of FIG. 1a), the controller (180 of FIG. 1a) of the mobile terminal may display the tracking trajectory of the previous or next date on the display unit (141 of FIG. 1a) through flicking input.

Referring to FIGS. 11(a) and 11(b), the controller may display the number "f" that is displayed in the circular time line, that is, the tracking trajectory of the current date (e.g., 2013 Jun. 25), and that indicates on what date has the tracking trajectory of the current date been obtained. Specifically, if the number "f" indicating that the tracking trajectory of the current date has been obtained is 5, it may be seen that the four tracking trajectories of a previous date have been stored.

When flicking input in a first direction d1 is received with respect to a specific region of the display unit, the controller may display the tracking trajectory of a previous date (e.g., 2013 Jun. 24) so that it corresponds to the flicking input direction. In this case, the previous date refers to a date right before the date on which a tracking history was stored, and the specific region may include the region in which the circular time line has been displayed.

Referring to FIGS. 11(c) and 1(d), when flicking input in a second direction d2 is received, the controller may display the tracking trajectory of a next date (e.g., 2013 Jun. 25) so that it corresponds to the flicking input direction. Likewise, the next date refers to a date stored after a currently displayed tracking history.

Referring to FIG. 12, if the tracking history of a previous or next date has been stored in the memory (170 of FIG. 1a), the controller (180 of FIG. 1a) of the mobile terminal may select the previous or next date through input to the current date "a" displayed within the circular time line T, and may display the tracking trajectory of the selected date.

Specifically, when touch input to the current date "a" displayed in the circular time line T is received, the controller may display a date selection menu of a wheel form in which a previous or next date may be selected in the form of a pop-up window W, and may select a specific date in the pop-up window W.

The controller may display a tracking trajectory, corresponding to a selected specific date, in the circular time line, and may display a tracking history, corresponding to a previous or next date, using an indicator.

Referring to FIG. 13, if the tracking history of previous or next dates has been stored in the memory (170 of FIG. 1a), the controller (180 of FIG. 1a) of the mobile terminal may reduce the size of the circular time line T displayed on the display unit (151 of FIG. 1a), and may display the reduced time line using indicators of a bead form. The controller may sequentially display indicators of a bead form, which correspond to the dates on which respective tracking trajectories have been stored.

Specifically, when pinch-out input to the region in which the circular time line T has been displayed is received, the controller may reduce the size of the circular time line T and display the reduced time line using indicators of a bead form.

When flicking input in the first direction d1 is received in the state in which indicators of a bead form have been displayed, the controller may move and display indicators of a bead form, corresponding to a previous date, in response to the flicking input. Accordingly, a user may check date information indicated within an indicator of a bead form and easily search for the tracking history of a specific date by performing flicking input.

Referring to FIG. 14, the controller (180 of FIG. 1a) of the mobile terminal may display the tracking trajectory of a specific date through pinch-in input to one of indicators of a bead form.

Specifically, when pinch-in input to an indicator corresponding to a specific date (e.g., 2013 Jun. 5) is received in the state in which a plurality of indicators of a bead form has been displayed, the controller may display the tracking trajectory of the specific date in the circular time line T.

Referring to FIG. 15, when flicking input is received in the state in which indicators of a bead form have been displayed on the display unit (151 of FIG. 1a), the controller (180 of FIG. 1a) of the mobile terminal may move the indicators of a bead form in response to the flicking input. When touch input to one of the displayed indicators of a bead form is received, the controller may display the tracking trajectory of a corresponding date.

Specifically, when flicking input in the second direction d2 is received in the state in which a plurality of indicators of a bead form has been displayed, the controller may display indicators of a bead form corresponding to next dates.

When touch input to an indicator that belongs to indicators of a bead form displayed on the display unit and corresponds to a specific date (e.g., 2013 Jun. 7) is received, the controller may display the tracking trajectory of the specific date (e.g., 2013 Jun. 7) in the circular time line.

Referring to FIG. 16, the controller (180 of FIG. 1a) of the mobile terminal may highlight and display an indicator of a bead form, which corresponds to the date on which target calories were achieved, and may display the time when the target calories were achieved in the circular time line using a specific indicator.

Specifically, the controller may display a plurality of tracking histories using indicators of a bead form, and may highlight and display the indicator of a date (e.g., 2013 Jun. 4) when target calories were achieved.

Furthermore, when touch input to a highlighted indicator is received, the controller may display the tracking trajectory of a corresponding date (e.g., 2013 Jun. 4) in the circular time line, and may display the time when the target calories were achieved using a specific indicator G.

Referring to FIG. 17, when touch input to the short cut icon of the current date displayed on one side of the display unit (151 of FIG. 1a) is received, the controller (180 of FIG. 1a) of the mobile terminal may display the tracking trajectory of the current date on the display unit (151 of FIG. 1a).

If a circular time line displayed on the display unit does not correspond to the current date, the controller may select the short cut icon of the current date and display the tracking trajectory of the current date in the circular time line. Accordingly, a user can check a previous tracking history using the short cut icon and then directly check the tracking trajectory of the current date.

Referring to FIG. 18, when the short cut icon of the current date is selected in the state in which the short cut icon has been displayed on one side of the side where indicators of a bead form have been displayed, the controller (180 of FIG. 1a) of the mobile terminal may display the tracking trajectory of the current date.

FIGS. 19 to 28 are diagrams for illustrating a method for displaying sensing information sensed from a paired accessory in the mobile terminal related to an embodiment of the present invention. In this case, the accessory may include an electronic device of a wearable form in which at least one sensor has been embedded. Specifically, the accessory may include a health information acquisition device, such as a motion quantity measurement device or blood sugar level measurement device of a wearable band, watch or necklace form or an earphone form.

Referring to FIG. 19, the controller (180 of FIG. 1a) of the mobile terminal may perform pairing with at least one accessory, and may display at least some of second circular time lines A, B, and C indicative of paired accessories on the left or right of a first circular time line T in which the tracking trajectory of the mobile terminal has been displayed.

If paired accessories are plural, the controller may display the second circular time lines A, B, and C at respective set locations according to a pairing sequence. For example, the controller may display at least some of the second circular time line A indicative of a first-paired first accessory so that it is located on the right of the first circular time line T, may display at least some of the second circular time line B indicative of a second-paired second accessory so that it is located on the left of the first circular time line T, and may display at least some of the second circular time line C indicative of a third-paired third accessory so that it is located on the right of the second circular time line A indicative of a first accessory. The controller may display only at least some of a plurality of the second circular time lines on the display unit depending on the size of the display unit, and may recognize that other portions have been displayed in a virtual region.

Referring to FIG. 19(a), the controller may display some of the second circular time lines indicative of the accessories B and A and the entire region of the first circular time line indicative of the mobile terminal on the display unit. Furthermore, the controller may recognize that the remaining portions of the second circular time lines indicative of the accessories B and A and the second circular time line indicative of the accessory C have been displayed in a virtual region.

Referring to FIG. 19(b), when flicking input in a fifth direction d5 is received in the state in which some of the second circular time lines indicative of the accessories B and A and the entire region of the first circular time line indicative of the mobile terminal have been displayed on the display unit, the controller may move each of the circular time lines by a set distance in the left direction, and may display the second circular time line indicative of the accessory A in the central area of the display unit.

Referring to FIG. 19(c), when flicking input in the fifth direction d5 is received again in the state in which the second circular time line indicative of the accessory A has been displayed at the center of the display unit, the controller may move each of the circular time lines by a set distance in the left direction, and may display the second circular time line indicative of the accessory C at the central area of the display unit.

Referring to FIG. 19(d), when flicking input in a sixth direction d6 is received in the state in which the second circular time line indicative of the accessory C has been displayed at the central area of the display unit, the controller may move each of the circular time lines by a set distance in the right direction, and may display the second circular time line indicative of the accessory A at the central area of the display unit.

Referring to FIG. 20, when flicking input in the fifth direction d5 is received in the state in which at least some of the first circular time line T and the second circular time lines A, B, and C has been displayed, the controller (180 of FIG. 1a) of the mobile terminal may move the plurality of circular time lines to the left by a set distance and display them.

When flicking input is received, the controller may change the display of the first circular time line T, displayed at the center of a screen of the display unit, to the display of the second circular time line A indicative of the accessory A. Furthermore, the controller may display the first circular time line T on the left of the second circular time line A indicative of the accessory A, and may display the second circular time line C indicative of the accessory C on the right of the second circular time line A indicative of the accessory A.

If the second circular time lines A, B, and C have been displayed at the center of a screen of the display unit, the controller may display a specific indicator "ia" indicative of the present time and synchronization times "ic", "ie", and "ig" when sensing information was sent to the mobile terminal in the second circular time line.

Referring to FIGS. 21 and 22, when input to the synchronization times "ic", "ie", and "ig" displayed in the second circular time line is received, the controller (180 of FIG. 1a) of the mobile terminal may display sensing information "ib", "id", and "if" about the synchronization times.

Referring to FIG. 23, if at least one accessory has been paired, the controller (180 of FIG. 1a) of the mobile terminal may transversely connect and display at least one indicator of a bead form.

Referring to FIG. 23(a), if the tracking histories of previous or next dates have been stored in the memory, the controller may sequentially display indicators of a bead form, corresponding to the tracking histories, in the longitudinal direction, and may display at least one indicator of a bead form, indicating an accessory paired with each date, in the transverse direction.

Referring to FIG. 23(b), the controller may display the tracking trajectory of a next date in the first circular time line in response to flicking input in the second direction, and may not display a second circular time line if there is no paired accessory.

Referring to FIG. 23(c), when the mobile terminal is paired with a new accessory B in the state in which the first circular time line has been displayed, the controller may display at least some of a second circular time line indicative of the accessory B so that it is located on the right of the first circular time line.

Referring to FIG. 23(d), when the mobile terminal is additionally paired with a new accessory A, the controller may display at least some of a second circular time line indicative of the accessory A so that it is located on the left of the first circular time line. Furthermore, when the mobile terminal performs pairing with a new accessory D in the state in which it has been paired with the accessories A and B, the controller may display a second circular time line indicative of the newly paired accessory D between the first circular time line and the second circular time line indicative of the accessory B.

The sequence that the second circular time lines are displayed according to the above accessory pairing sequence may be set in response to user input or may be set by default. The controller may change the display sequence through touch input to the second circular time line.

FIGS. 24 to 28 correspond to a method for searching for a tracking history in the state in which at least one accessory has been paired, and they are similar to FIGS. 11 to 17 described above and only differences between them are described in brief.

Referring to FIG. 24, if at least one accessory has been paired, the controller (180 of FIG. 1a) of the mobile terminal may check sensing information about another accessory displayed in a circular time line through left or right flicking input.

Furthermore, the controller may change indicators of a bead form by reducing the region in which a second circular time line including sensing information has been displayed in response to pinch-out input to the second circular time line. The controller may sequentially display indicators of a bead form indicative of tracking histories in the longitudinal direction, and may display an indicator of a bead form, indicating at least one accessory paired in the transverse direction, on the left or right of an indicator corresponding to a paired specific date.

Referring to FIG. 25, when touch input or pinch-in input to one of indicators of a bead form is received, the controller (180 of FIG. 1a) of the mobile terminal may display the tracking trajectory of the date on which the input was received in a first circular time line. When touch input or pinch-in input to one of indicators of a bead form corresponding to a specific accessory is received, the controller may display sensing information about the specific accessory in a second circular time line.

Referring to FIG. 26, when flicking input in the first direction d1 is received in the state in which a second circular time line including sensing information about a specific accessory has been displayed, the controller (180 of FIG. 1a) of the mobile terminal may display the tracking trajectory of a previous date. In contrast, when flicking input in the second direction is received, the controller may display the tracking trajectory of a next date.

Furthermore, if the same accessory has been paired with a previous or next date in response to flicking input to the first direction or the second direction, the controller may display a second circular time line including sensing information about a specific accessory corresponding to the previous or next date.

Referring to FIG. 27, when input to the short cut icon of the current date displayed on one side of the second circular time line of a specific accessory is received, the controller (180 of FIG. 1a) of the mobile terminal may change the second circular time line into the first circular time line that displays the tracking trajectory of the current date.

Referring to FIG. 28, when touch input to date information displayed in the second circular time line of a specific accessory is received, the controller (180 of FIG. 1a) of the mobile terminal may display a date selection menu of a wheel form in which a previous or next date may be selected in a pop-up window W, and may select a specific date by turning the wheel.

The controller may display a tracking trajectory corresponding to the selected specific date in a circular time line, and may display a tracking history corresponding to the previous or next date using an indicator.

FIGS. 29 to 36 are diagrams for illustrating a method for managing location information corresponding to the tracking trajectory of a user, which has been sensed in the mobile terminal related to an embodiment of the present invention.

Referring to FIG. 29, the controller (180 of FIG. 1a) of the mobile terminal may additionally store location information about a tracking trajectory, and may display a recording trajectory in relation to the tracking trajectory.

Specifically, when input to other menu "h" displayed on the execution screen of the specific application is received, the controller may display a down-one level menu in a pop-up window W. When input to "Record track" in the down-one level menu is received, the controller may display the current location of the mobile terminal and a related map and start track recoding.

When the track recoding is performed, the controller may display a recording trajectory "tr" in relation to the tracking trajectory "ma."

Referring to FIG. 30, when input to other menu "h" displayed on the execution screen of track recoding is received, the controller (180 of FIG. 1a) of the mobile terminal may display a down-one level menu in a pop-up window W. When input to "Record track" in the down-one level menu is received, the controller may display a recording trajectory in a map and display a new screen including the control menu of the track recoding.

The controller may perform a pause, an end or re-recording on the track recoding through the control menu of the track recoding, for example, input to the pause, end or re-recording.

Referring to FIG. 31, the controller (180 of FIG. 1a) of the mobile terminal may provide a menu "i" in which a motion of a user may be directly selected in a track recoding execution screen, may determine a motion type of the user through selection for a specific motion type, and may display a tracking trajectory with a corresponding display characteristic in a circular time line.

If the motion type of the user has been determined, the controller may display the determined motion type on one side of the track recoding execution screen using an icon "i'." Furthermore, when the motion type of the user is changed in response to selection for a specific motion type, the controller may reset track recoding.

Referring to FIGS. 32 and 33, when touch input to a recording trajectory "tr" displayed in relation to a tracking trajectory "ma" is received, the controller (180 of FIG. 1a) of the mobile terminal may display the recording trajectory in a map.

The controller may display information about the moving distance, moving speed, and consumed calories of a user and some of a recoding control menu in a specific region of the lower part of the map. When sliding input to the specific region is received, the controller may display the information about the moving distance, moving speed, and consumed calories of the user and detailed information about the recoding control menu on the entire screen. Furthermore, when sliding input in an opposite direction is received in the state in which the information about the moving distance, moving speed, and consumed calories of the user and the detailed information about the recoding control menu have been displayed on the entire screen, the controller may recover the display state to a previous state.

Referring to FIG. 34, the controller (180 of FIG. 1a) of the mobile terminal may provide other menu "j" in the track recoding execution screen and send the execution screen of track recoding to another application.

Referring to FIG. 35, when track recoding is requested, the controller (180 of FIG. 1a) of the mobile terminal may determine whether the GPS module is an on state. If the GPS module is an off state, the controller may display a pop-up window W' that checks whether the GPS module will be turned on or not. Furthermore, if the GPS module is an off state when track recoding is requested, the controller may display contents, indicating that a map is unable to be displayed, in the pop-up window W'.

If the GPS module has been turned off while track recoding is performed, the controller may display contents, indicating that the track recoding is automatically terminated, in the pop-up window W'.

Referring to FIG. 36, if a track recoding function is executed in the background, the controller may display brief information related to track recoding in a notification bar. When touch input to the brief information is received, the controller may perform a short cut to the track recoding execution screen.

FIGS. 37 to 40 are diagrams for illustrating a method for displaying other information related to the tracking trajectory of a user sensed in the mobile terminal related to an embodiment of the present invention.

Referring to FIG. 37, when input to a specific menu "g" displayed on the execution screen of the specific application is received, the controller (180 of FIG. 1a) of the mobile terminal may display another function, provided by the specific application, on a sliding screen SP or in a pop-up window.

For example, when input to the specific menu "g" is received, the controller may display menus, such as "Exercise", "Ranking list", and "Track list", on the sliding screen SP.

Referring to FIG. 38, when selection input to the menu "Exercise" is received, the controller (180 of FIG. 1a) of the mobile terminal may provide the statistic information of tracking information daily, weekly or yearly.

Specifically, the controller may divide the display unit into regions A to E, and may display a menu name in the region A, a statistic information providing unit in the region B, exercise information about a user in the region C, a graph in which exercise information about a user is displayed in detail based on specific parameters in the region D, and brief information about a recording trajectory in the region E.

Referring to FIG. 39, when selection input to the menu "Ranking list" is received, the controller (180 of FIG. 1a) of the mobile terminal may provide tracking information received from another mobile terminal in a list form.

Specifically, the controller may divide the display unit into the regions A to C, and may display a menu name in the region A, tracking information about a user in the region B, and tracking information received from another user in the region C. In this case, the controller may display the list in order of the quantity of motion so that the user may check his or her order of the quantity of motion in a relation with other users.

Referring to FIG. 40, when selection input to the menu "Track list" is received, the controller (180 of FIG. 1a) of the mobile terminal may provide detailed information about a recording trajectory.

Specifically, the controller may divide the display unit into regions A to C, and may display a menu name in the region A, date information in the region B, and detailed information about recording trajectories in the region C.

When detailed information about a specific recording trajectory displayed in the region C is selected, the controller may display information about the ID of the selected specific recording trajectory, information about the specific recording trajectory displayed in a map, and brief information about the specific recording trajectory in respective divided regions of the display unit.

FIG. 41 is a flowchart for illustrating another embodiment of a method for controlling a mobile terminal, which is related to the present invention. FIGS. 42 to 60 are diagrams for illustrating another embodiment of a method for controlling a mobile terminal, which is related to the present invention.

Referring to FIG. 41, the controller (180 of FIG. 1a) of the mobile terminal may execute the specific application (S210), and may receive input to request a comparison between first exercise information and second exercise information through the execution screen of the specific application (S220). In this case, the first exercise information may be exercise information about the user of the mobile terminal, and the second exercise information may be exercise information that is transmitted by the mobile terminal of a specific person in real time or periodically or a specific exercise record stored in a server.

The specific application is an application which provides information related to exercises, such as a sensed exercise type, a sensed moving distance, and sensed consumed calories. The specific application may provide exercise information about the user using sensing information sensed by a sensor, including at least one of an acceleration sensor, a magnetic sensor, a gravity sensor, a gyroscope sensor, and a motion sensor embedded in the mobile terminal.

The controller stores the exercise information of the user sensed by a plurality of sensors embedded in the mobile terminal regardless of whether the specific application has been executed or not. When the specific application is executed, the controller may provide the stored exercise information of the user through the execution screen of the specific application.

When input to an exercise competition menu in the execution screen of the specific application is received, the controller may treat the input as input to request a comparison between pieces of exercise information.

A first down-one level menu in which the exercise information of the user is displayed, a second down-one level menu in which a competition with exercise information about a specific person is displayed, a third down-one level menu in which a group is created and exercises for the group are displayed, and a fourth down-one level menu in which exercise information is displayed in a map and an exercise method is recommended may be displayed on the exercise screen of the specific application. When selection input to the second down-one level menu is received, the controller may treat the selection input as input to request a comparison between pieces of exercise information.

Furthermore, when input to a specific region or specific menu button in the execution screen of the first down-one level menu that belongs to the execution screen of the specific application and in which the exercise information of the user is displayed is received, the controller may treat the input as input to request a comparison between pieces of exercise information. Specifically, when the first down-one level menu is selected, the controller may display a circular time line in which both time information and exercise information are displayed on the execution screen of the first down-one level menu. When specific input to one point on the circular time line or one point within the circular time line is received, the controller may treat the specific input as input to request a comparison between pieces of exercise information.

When input to request a comparison between pieces of exercise information is received, the controller may display a screen in which a specific person, that is, an exercise competitor, is selected for a comparison with exercise information about the specific person. The controller may display a competitor of a telephone directory stored in the memory, a competitor of a telephone directory stored in relation to a Social Network Service (SNS), and a competitor list received from the server, and may select a specific competitor of the competitor list as a specific person.

When the specific person is selected, the controller may provide a user interface through which sports for a competition may be selected. When input that selects specific sports is received from the user, the controller may perform a comparison with exercise information about the selected specific sports.

When the input to request a comparison between pieces of exercise information is received, the controller (180 of FIG. 1a) of the mobile terminal may receive the first exercise information sensed by the sensing unit (140 of FIG. 1a) (S230), and may receive the second exercise information by requesting it through the wireless communication unit (110 of FIG. 1a) (S240 and S250). Hereinafter, the first exercise information is assumed to be the exercise information of the user and the second exercise information is assumed to be the exercise information of the specific person.

The controller may recognize input to request a comparison between pieces of exercise information as a triggering signal that activates the sensing unit, and may activate the sensing unit so that the exercise information of the user is sensed. Furthermore, the controller may recognize input to request a comparison between pieces of exercise information as a triggering signal to transfer exercise information sensed by the sensing unit to the controller. In this case, the sensing unit always maintains an activation state and may sense a motion of a user who owns the mobile terminal.

The controller may request exercise information about a specific person from the mobile terminal of the specific person or may request the exercise information of the specific person from a server in which the exercise information of the specific person has been stored. Specifically, when the controller requests the exercise information of the specific person from the mobile terminal of the specific person, it may request the exercise information to be transmitted to the mobile terminal of the user in real time. In this case, if the specific person agrees with the real-time transmission of the exercise information, the controller may receive the real-time exercise information through the wireless communication unit. The server may collect exercise information about each user from a plurality of mobile terminals on each of which the specific application has been installed, may manage the collected exercise information, and may additionally manage exercise information about a celebrity. If exercise information about a specific person is received from a server, the controller may receive the exercise information of the specific person, corresponding to the exercise time of the user, in real time or at once, and may display the received exercise information.

The controller (180 of FIG. 1a) of the mobile terminal may compare the sensed exercise information of the user with the received exercise information of the specific person, and may display them on the display unit (151 of FIG. 1a) together. The controller may display the exercise information of the user and the exercise information of the specific person using a graphic object indicative of sports for a competition so that they are visually distinguished from each other.

The mobile terminal may refer to a terminal which may be possessed or worn by a user, such as a smart phone, a watch phone, or smart glasses. If two mobile terminals operate in conjunction with each other as a master device and a slave device, the mobile terminal may refer to at least one of the master device and the slave device. For example, if a smart phone has been set as a master device, a watch phone has been set as a slave device, the smart phone and the watch phone operate in conjunction with each other, the specific application is executed in the smart phone in the state in which a user has worn the watch phone, but has not possessed the smart phone, and the user selects a specific person and requests a comparison between pieces of exercise information, the watch phone of the user may sense the exercise information of the user and display the received exercise information of the specific person.

If a difference between the exercise information of the user and the exercise information of the specific person as a result of a comparison approaches one of a specific time range or less, a specific distance range or less, and a specific calorie range or less, the controller may perform control so that at least one of visual feedback, auditory feedback, and tactile feedback is output. If a master device and a slave device operate in conjunction with each other, the controller may output feedback to a device owned by a user.

If an exercise type selected by the specific person to compete with is different from an exercise type selected by the user, the controller (180 of FIG. 1a) may display the exercise type of the user and the exercise type of the specific person on the display unit (151 of FIG. 1a), may convert exercise information about each of the specific person and the user into consumed calories, and may compare the consumed calories of the user with the consumed calories of the specific person.

The controller of the slave device may store the results of the exercises of the user in the specific application, and may share the information stored in the specific application through synchronization with the master device.

The controller (180 of FIG. 1a) may set at least one of exercise equipment information, exercise record information, and topography information related to information about the current location of the mobile terminal and information about input of the user received through the input unit (120 of FIG. 1a) as parameters, and may recommend an appropriate exercise type and exercise method. In this case, the input information of the user may include information about at least one of an exercise limit time, target calories, and sporting equipment to be used. If at least one of the parameters is changed, the controller may recommend an appropriate exercise type and exercise method again based on the changed parameter.

FIGS. 42 to 60 are diagrams for illustrating a method for a real-time or periodical comparison with exercise information about another person and for the display of the results of the comparison in the mobile terminal according to another embodiment of the present invention.

FIGS. 42 to 50 are diagrams for illustrating a method for directly selecting the second down-one level menu included in the execution screen of the specific application and for displaying the results of an exercise competition with a specific person in the mobile terminal related to an embodiment of the present invention.

Referring to FIG. 42, the controller (180 of FIG. 1a) of the mobile terminal may display the second down-one level menu, included in the execution screen of the specific application, on the display unit 351 or 151 or both. Specifically, a user interface of the execution screen of the specific application if the mobile terminal is a watch phone or a smart phone is described below.

When the specific application providing exercise information is executed, the controller may display a menu (e.g., Daily Summary) providing daily exercise information about a user, setting menus (e.g., Exercise, Ranking, Compete in, and Groups) related to exercises, and a menu (e.g., Record track) related to an exercise record on the execution screen of the specific application.

If all of items to be displayed on the execution screen of the specific application are not displayed on the display unit 351 or 151 or both, the controller may display non-displayed items on the display unit through scroll input.

The controller may select the menu "Compete in" for an exercise competition with another person in the setting menus related to exercises.

Referring to FIG. 43, when the menu "Compete in" for an exercise competition with another person is selected, the controller (180 of FIG. 1a) of the mobile terminal may enter exercise competition mode and display a screen in which an exercise type and a specific person may be selected on the display unit 351 or 151 or both.

Referring to FIG. 44, the controller (180 of FIG. 1a) of the mobile terminal may display a user interface through which an exercise type may be selected on the display unit 351 or 151 or both.

Specifically, the controller may classify exercise types into pieces of major classification, such as RUNNING and CYCLING, and may display down-one level classification of each of the pieces of major classification in a list form. When input by the user for one of the list is received, the controller may select an item to which the input of the user has been received as an exercise type. For example, when the input of the user for 400 m race is received, the controller may determine an exercise type for a competition to be 400 m race.

Referring to FIG. 45, the controller (180 of FIG. 1a) of the mobile terminal may display a user interface through which a specific person to compete with may be selected on the display unit 351 or 151 or both.

Specifically, the controller may select a competitor or celebrity of a telephone directory stored in the memory as a specific person to compete with. For example, the controller may select EEE, that is, a competitor of a telephone directory stored in the memory, as a specific person in response to user selection.

Referring to FIG. 46, when a competition request of a specific exercise type is received from another person, the controller (180 of FIG. 1a) of the mobile terminal may display the received contents on the display unit 351 or 151 or both in a pop-up window form.

Specifically, when a request for 400 m race is received from the mobile terminal of AAA, the controller of the mobile terminal may display the received contents on the display unit. When an item "Start" is selected by the user, the controller may send a response message to the mobile terminal of AAA.

FIG. 47 shows a real-time exercise competition method between a first mobile terminal 300A and a second mobile terminal 300B.

The controller of the first mobile terminal 300A may display a user interface through which whether an exercise competition will be requested from the second mobile terminal 300B is selected on the display unit 351A of the first mobile terminal 300A. When input to request an exercise competition is received (or checked and selected), the controller of the first mobile terminal 300A may send notification to request the exercise competition to the second mobile terminal 300B. The controller of the second mobile terminal 300B displays the notification to request the exercise competition received from the first mobile terminal 300A. When the request for the exercise competition is accepted (or checked and selected), the controller of the second mobile terminal 300B may send a response message to the first mobile terminal 300A.

After the response message is transmitted, the controller of each of the first mobile terminal and the second mobile terminal may display a message, providing notification of the start of the exercise competition, to each of the display units 351A and 351B when a set time is reached. Specifically, the controller of each mobile terminal may display an indicator, indicating that the current time corresponds to what seconds, for example, prior to the start of the exercise competition, on the display unit so that each user may recognize the start of the exercise competition. Each of the first mobile terminal and the second mobile terminal may send exercise information in real time, may compare its own exercise information with a competitor's exercise information, and may display the results of the comparison.

Referring to FIG. 48, the controller (180 of FIG. 1a) of the mobile terminal may display both exercise information about the specific person and exercise information about the user on the display unit 351 or 151 or both.

The controller may display pieces of exercise information "a" to "d" about the specific person and the user on an appropriate graphic object (e.g., 400 m track) indicative of an exercise type so that the pieces of exercise information may be intuitively compared with each other.

Referring to FIG. 49, the controller (180 of FIG. 1a) of the mobile terminal may output feedback if each of the exercise information of the specific person and the exercise information of the user is included in a predetermined range.

Specifically, if a difference between exercise information about a specific person EEE and exercise information about a user ME approaches one of a specific time range or less, a specific distance range or less, and a specific calorie range or less, the controller may output at least one of visual feedback, auditory feedback, and tactile feedback.

For example, if a difference between the distance of the specific person EEE and the distance of the user ME is included in a specific distance range or less, the controller may change light and darkness of the display unit 351 or 151 or both and output vibration.

Referring to FIG. 50, when the exercise competition is completed, the controller (180 of FIG. 1a) of the mobile terminal may display a graphic interface through which the exercise information of the specific person is compared with that of the user on the display unit 351 or 151 or both. At this time, the controller may also display the exercise type and consumed calories in the graphic interface.

FIGS. 51 to 54 are diagrams for illustrating a method for displaying the results of an exercise competition with a specific person through specific input to the execution screen of the second down-one level menu of the specific application in the mobile terminal related to an embodiment of the present invention.

Referring to FIG. 51, when input to a specific region or specific menu button in the execution screen of the first down-one level menu that belongs to the execution screen of the specific application and on which exercise information about a user is displayed is received, the controller (180 of FIG. 1a) of the mobile terminal may treat the received input as input to request a comparison between pieces of exercise information.

Specifically, when touch input to the internal region of a circular time line displayed on the execution screen of the first down-one level menu is received, the controller may recognize the received input as input to request a comparison between pieces of exercise information, and may enter exercise competition mode.

When the controller enters the exercise competition mode, it may change the display of exercise information about a user, displayed in the circular time line T, into the display of a screen in which an exercise type or a specific person, that is, an exercise competitor, is selected.

Referring to FIG. 52, when a specific person is selected and an exercise competition is requested, the controller (180 of FIG. 1a) of the mobile terminal may send the contents of the exercise competition request to the mobile terminal of the specific person, and may display the state in which an exercise competition is a Ready "d" state in the circular time line T until an approval signal is received from the mobile terminal of the specific person. The controller may display indicators "b" and "c" indicative of the user and the competitor at the start point "a" of the circular time line T.

If an approval signal has not been received from the mobile terminal of the specific person within a set time, the controller may release the exercise competition mode and restore the display of the circular time line T to a previous display state.

When an approval signal is received from the mobile terminal of the specific person, the controller may display an indicator "d" to count an exercise competition start time within the circular time line T. Furthermore, when the exercise competition starts, the controller may sense first exercise information from the mobile terminal of the user, may receive second exercise information from the mobile terminal of the specific person in real time, may compare the first exercise information with the second exercise information, and may display the results of the comparison. For example, the controller may compare the quantity of motion of the user with the quantity of motion of the specific person, and may display the indicators "b" and "c" indicative of the user and the specific person, respectively, in relative locations of the circular time line T. In this case, the circular time line T may display reference motion quantity information, exercise distance information, and target motion quantity information.

Referring to FIG. 53, if the first exercise information is to be compared with the second exercise information and the results of the comparison are to be displayed, the controller (180 of FIG. 1a) of the mobile terminal may display the current exercise type of the user, and may recommend an exercise type which may surpass the quantity of motion of the specific person.

Specifically, if the location of the indicator "b" indicative of the quantity of motion of the user is relatively closer to the start point "a" than the location of the indicator "c" indicative of the quantity of motion of the specific person, the controller may determine that the specific person outdistances the user in the exercise competition. If the controller determines that the user loses the lead to the specific person in the exercise competition, it may recommend another exercise type "f" which may increase consumption calories depending on the current exercise type "e" of the user and a difference between the quantity of motion of the user and the quantity of motion of the specific person. The controller may recommend a different exercise type depending on a change of a difference between the quantity of motion of the user and the quantity of motion of the specific person.

Referring to FIG. 54, if the exercise competition mode is entered through the execution screen of the second down-one level menu and the results of the exercise competition are to be displayed, the controller (180 of FIG. 1*a*) of the mobile terminal may store the second exercise information of the specific person as a second circular time line T'.

The controller may store the first exercise information of the user in the first circular time line T, and may display information related to the exercises of the user, received from another wearable device worn by the user and linked to the mobile terminal, and the second exercise information of the specific person as second circular time lines B, A, C, and T'. In this case, the controller may display exercise types in the second circular time lines using the exercise information received from another wearable device or the mobile terminal of the specific person so that the exercise types are distinguished from each other (e.g., oblique lines of different forms).

FIGS. 55 to 60 are diagrams for illustrating a method for generating a group through specific input to the execution screen of the specific application and displaying the results of an exercise competition with members belonging to the group in the mobile terminal related to an embodiment of the present invention.

Referring to FIG. 55, when selection input to the third down-one level menu in the execution screen of the specific application is received, the controller (180 of FIG. 1*a*) of the mobile terminal may display a screen in which a group is created.

Referring to FIG. 56, the controller (180 of FIG. 1*a*) of the mobile terminal may select at least one of the mobile terminal of a competitor included in an SNS directory, the mobile terminal of a competitor included in the telephone directory, the mobile terminal of a competitor included in a chatting record, and a mobile terminal located within a set radius, and may create a group using the selected mobile terminal. At this time, the controller may also display a communication technology (e.g., Wi-Fi or a BT) that enables link to each member.

Referring to FIG. 57, when specific input to the execution screen of the second down-one level menu of the specific application is received, the controller (180 of FIG. 1*a*) of the mobile terminal may display a screen in which a group is created. That is, the controller may control a direct movement to another down-one level menu while a specific down-one level menu (e.g., the second down-one level menu) of a plurality of the down-one level menus displayed on the first execution screen of the specific application is executed.

Specifically, when touch input to a specific region within a circular time line displayed on the execution screen of the first down-one level menu is received, the controller may enter the group competition mode, and may display a screen in which a group is created within the circular time line. When the controller enters the group competition mode, it may change the display of exercise information about the user, displayed within the circular time line, into the display of information related to the group competition mode.

As in the case where the third down-one level menu that belongs to the first execution screen of the specific application and in which the group competition mode is entered is selected, the controller may display group creation information, group member selection information, and exercise information about group members within a circular time line.

In particular, the controller may change the display of exercise information about a user in the circular time line into the display of information about the quantity of motion of each of group members Me, AAA, and BBB, and may display the quantities of motion of all of the group members and the quantity of motion of the user Me within the circular time line in numbers.

Referring to FIGS. 58 to 60, when selection input to a specific group (e.g., Best friends) of created groups is received, the controller (180 of FIG. 1*a*) of the mobile terminal may display exercise information about the members of the specific group (Best friends). In this case, the controller may display the quantities of motion of the members using a graphic interface so that they may be intuitively compared with each other.

When input to an order comparison between groups is received, the controller may provide a graphic interface for comparing pieces of exercise information between the groups. In this case, the controller may display a group to which the user belongs and other groups so that the group to which the user belongs is distinguished from other groups.

In accordance with an embodiment of the present invention, users who have worn wearable devices can competitively exercise because they exchange exercise information in real time. Exercise information about a competitor or group members can be compared and managed, and the most appropriate exercise type and exercise method can be recommended using situation information.

FIG. 61 is a flowchart for illustrating another embodiment of a method for controlling the mobile terminal, which is related to the present invention. FIGS. 62 to 70 are diagrams for illustrating yet another embodiment of a method for controlling the mobile terminal, which is related to the present invention.

Referring to FIG. 61, the controller (180 of FIG. 1*a*) of the mobile terminal may execute a specific application (S310), and may limit at least one parameter through the execution screen of the specific application (S320).

The specific application is an application that provides information related to exercises, such as a sensed exercise type, moving distance, and consumed calories. The specific application may provide exercise information about a user using sensing information sensed by a sensor, including at least one of an acceleration sensor, a magnetic sensor, a gravity sensor, a gyroscope sensor, and a motion sensor embedded in the mobile terminal.

The controller may store the exercise information of the user, which has been sensed by the plurality of sensors embedded in the mobile terminal, regardless of whether the specific application is executed or not. When the specific application is executed, the controller may provide the stored exercise information of the user through the execution screen of the specific application.

The controller may limit at least one parameter of surrounding sports equipment, target calories, an exercise type, and an exercise time according to the current location information in response to user input, while displaying a tracking history according to a motion of the user in the execution screen of the specific application in a map.

When input to request an exercise recommendation based on a limited parameter is received, the controller (180 of FIG. 1*a*) of the mobile terminal may display recommended exercise information on the display unit (151 of FIG. 1*a*).

The controller may recommend an exercise method for achieving the quantity of motion desired by the user based on the limited parameter, and may display the recommended exercise method on the display unit. At this time, the controller may provide an image that executes a specific exercise type in addition to the exercise type.

For example, when input to limit the location to the current location of the mobile terminal, to limit time to 10 minutes, and to limit target calories to 100 kcal and an exercise recommendation request are received, the controller may recommend running of 20 km/h and may display an image of running for 10 minutes on the display unit.

FIGS. 62 to 70 are diagrams for illustrating a method for recommending appropriate exercises if a condition on a specific parameter is limited in the mobile terminal according to yet another embodiment of the present invention.

Referring to FIGS. 62 to 64, when only the location is limited and an exercise recommendation request is received, the controller (180 of FIG. 1*a*) of the mobile terminal may provide exercise record information related to information about the current location of the mobile terminal.

Specifically, the controller may display an exercise history related to the information about the current location of the mobile terminal on the display unit 351 or 151 or both. For example, if the information about the current location S of the mobile terminal and an exercise history stored within a set radius have been stored in a server, the controller may access the server, may receive a previous exercise history (i.e., an EEE exercise course), and may display the previous exercise history in a map.

The controller (180 of FIG. 1*a*) of the mobile terminal may provide exercise equipment information or topography information related to the information about the current location of the mobile terminal. Furthermore, the controller may display exercise equipment information related to the information about the current location of the mobile terminal on the display unit 351 or 151 or both. For example, the controller may display exercise equipment information (e.g., Gym) or topography information (e.g., a cycling road) within a set radius from the current location S of the mobile terminal in a map.

The controller may display a detailed exercise method using exercise equipment related to the information about the current location of the mobile terminal on the display unit 351 or 151 or both. For example, if a pull-up bar is available at the current location S of the mobile terminal information, the controller may display an exercise method using the pull-up bar on the display unit.

Referring to FIGS. 65 to 67, the controller (180 of FIG. 1*a*) of the mobile terminal may limit the location information of the mobile terminal, an exercise time, and target calories, and may request an exercise recommendation.

Specifically, when a time limit and target calories are received from the user, the controller may recommend an exercise type and exercise method available in the current location information within the limited time. If exercise information has been displayed in a map, the controller may treat a location limit as having been inputted by default.

For example, the controller may recommend running and hiking of 20 km/h using information about the current location of the mobile terminal, inputted target calories of 200 Kcal, and an exercise limit time of 30 minutes, and may display the recommended running and hiking on the display unit.

Referring to FIGS. 68 to 70, when specific input to the indicator "ia" on the circular time line T displayed on the execution screen of the first down-one level menu of the specific application is received, the controller (180 of FIG. 1*a*) of the mobile terminal may treat the received input as input to limit a specific parameter and recommend an exercise method. That is, when specific input is received in the execution screen of the first down-one level menu, the controller may display the execution screen of a fourth down-one level menu along with the execution screen of the first down-one level menu.

Referring to FIG. 68, when input to drag the indicator "ia" on the circular time line T displayed on the execution screen of the first down-one level menu to another point on the circular time line T is received, the controller (180 of FIG. 1*a*) of the mobile terminal may recommend an exercise method capable of achieving the remaining target calories during time corresponding to the end point of the drag input.

Specifically, when the indicator "ia" indicative of the present time in the circular time line T is dragged to a next time, the controller may display the indicator ia' indicative of the next time at a drag end point, and may display a difference (e.g., for 2:30) between the present time and time corresponding to the drag end point.

The controller may display an exercise method capable of achieving 520 kcal, that is, the remaining target calories, during the difference between the present time and the time corresponding to the drag end point within the circular time line T. For example, if a recommended exercise method is cycling, the controller may visually display an indicator (e.g., a figure of a person form who rides a bicycle) so that the user can intuitively recognize the recommended exercise method.

Referring to FIG. 69, when input to a specific region within the circular time line T is received in the state in which a recommended exercise method has been displayed, the controller (180 of FIG. 1*a*) of the mobile terminal may enter the exercise competition mode.

As described above, when the controller enters the exercise competition mode, it may select a specific person, and may display exercise information for a competition with the specific person in order to achieve target calories during a set time in the circular time line.

Referring to FIG. 70, when input to a specific region within the circular time line T is received in the state in which a recommended exercise method has been displayed, the controller (180 of FIG. 1*a*) of the mobile terminal may enter the group competition mode.

When the controller enters the group competition mode, it may change the display of exercise information about the user into the display of information related to a group competition. Specifically, the controller may display a screen in which a group is created within the circular time line T, and may display exercise information about each member of the created group within the circular time line T. When the group is created, the controller may display a limited time (i.e. for 2:30) and target calories (520 kcal) within the circular time line T, may display different oblique lines indicative of the exercise types of respective members (Me, AAA, and BBB) in the circular time line T, and may display the quantity of motion of each of the members in numbers.

In accordance with an embodiment of the present invention, a plurality of one-down level menus of a specific application that provides exercise information are enabled to operate in conjunction with each other, thereby being capable of displaying the results of the execution of different one-down level menus on the execution screen of a specific one-down level menu.

The present invention may be applied to a recording medium on which a method for managing exercise information has been recorded, a device for executing the recording medium, and mobile terminals including a smart phone, a watch phone, glasses, PDA, a notebook, and IPTV having sensors embedded therein.

Various embodiments may be implemented using a machine-readable medium having instructions stored therein for execution by a processor to perform various methods presented herein. Examples of possible machine-readable mediums include Hard Disk Drive (HDD), Solid State Disk (SSD), Silicon Disk Drive (SDD), ROM, RAM, CD-ROM, a magnetic tape, a floppy disk, an optical data storage device, the other types of storage mediums presented herein, and combinations thereof. If desired, the machine-readable medium may be realized in the form of a carrier wave (e.g., transmission over the Internet). The processor may include the controller 180 of the mobile terminal.

The foregoing embodiments are merely exemplary and are not to be considered as limiting the present disclosure. The present teachings can be readily applied to other types of methods and apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds, are therefore intended to be embraced by the appended claims.

The invention claimed is:

1. A mobile terminal, comprising:
a memory;
a sensing unit;
a display unit; and
a controller configured to display a first circular time line on the display unit when a specific application is executed and to display a motion of a user sensed by the sensing unit in the first circular time line in a tracking trajectory form in real time, wherein the tracking trajectory is displayed to have a different display characteristic based on a type of the sensed motion of the user,
wherein the controller is configured to:
reduce a size of the circular time line displayed on the display unit if a history of tracking trajectories have been stored in the memory, and
sequentially display a history of tracking trajectories of previous or next dates using indicators of a bead form.

2. The mobile terminal of claim 1, wherein the controller is configured to display the tracking trajectory only in a time interval in which the motion of the user has been sensed when the motion of the user is intermittently sensed.

3. The mobile terminal of claim 1, wherein the controller is configured to:
display information about a number of steps, moving distance, target calories, and consumed calories of the user within the first circular time line,
update the information based on the motion of the user sensed by the sensing unit in real time, and
display the updated information.

4. The mobile terminal of claim 1, wherein the controller is configured to:
display a specific indicator in the first circular time line corresponding to a present time, and
display the present time in numbers when input to the specific indicator is received.

5. The mobile terminal of claim 1, wherein the controller is configured to display a specific indicator at a specific time if it is determined that a motion of the user accumulated up to the specific time has achieved target calories.

6. The mobile terminal of claim 1, wherein the controller is configured to
display an indicator corresponding to a date which belongs to the history of the previous or next dates and on which target calories have been achieved in a different form.

7. The mobile terminal of claim 6, wherein the controller is configured to:
move a location of the indicators of the bead form in response to the flicking input to the indicators of the bead form,
enlarge a tracking trajectory of a date corresponding to a specific indicator which belongs to the moved indicators of the bead form and which has been disposed at a set location, and
display the enlarged tracking trajectory on the display unit.

8. The mobile terminal of claim 6, wherein the controller is configured to:
enlarge a display region of a specific indicator of the indicators of the bead form and display a tracking trajectory of a date corresponding to the specific indicator on the enlarged display region when a pinch-in input to the specific indicator is received, and reduce the enlarged display region to a previous size and display the specific indicator in the reduced display region when pinch-out input to the tracking trajectory of the date corresponding to the specific indicator is received.

9. The mobile terminal of claim 1, wherein the controller is configured to:
perform pairing with at least one accessory,
display at least some of a second circular time line indicative of the paired accessory on a left or right of the first circular time line, and
display an indicator indicative of a number of the paired accessories within the first circular time line.

10. The mobile terminal of claim 9, wherein the controller is configured to:
change the display of the first circular time line into the display of the second circular time line in response to left or light flicking input, and display the first circular time line or another second circular time line different from the second circular time line on a left or right of the second circular time line.

11. The mobile terminal of claim 10, wherein the controller is configured to display sensing information received from the paired accessory in the second circular time line, wherein time when the sensing information is received is differently displayed in the second circular time line.

12. The mobile terminal of claim 1, wherein the controller is configured to:
store location information according to the motion of the user along with the tracking trajectory when specific input is received through the display unit, and
display an additional trajectory inside or outside a tracking trajectory corresponding to a time interval in which the location information has been stored.

13. The mobile terminal of claim 12, wherein the controller is configured to further display a map in which the location information according to the motion of the user has been displayed and a user interface comprising a moving distance, moving speed, and consumed calories corresponding to the time interval in which the location information has been stored.

14. The mobile terminal of claim 1, wherein the controller is configured to:
receive tracking information about another user who shares the tracking trajectory,
align the received tracking information, and
display the aligned tracking information in a list form.

15. The mobile terminal of claim 1, further comprising a wireless communication unit, wherein the controller is configured to:
sense first exercise information indicative of the motion of the user through the sensing unit when specific input is received through an execution screen of the specific application,
receive second exercise information through the wireless communication unit,
compare the sensed first exercise information with the received second exercise information, and
display results of the comparison on the display unit.

16. The mobile terminal of claim 15, wherein the controller is configured to:
send notification to request the second exercise information to an external mobile terminal,
periodically receive the second exercise information sensed by the external mobile terminal,
periodically update the second exercise information and the first exercise information, and
display the updated second exercise information and the first exercise information.

17. The mobile terminal of claim 15, wherein the controller is configured to:
compare the first exercise information with the second exercise information, and
perform control so that at least one of visual feedback, auditory feedback, and tactile feedback is output if a difference between the first exercise information and the second exercise information approaches one of a specific time range or less, a specific distance range or less, and a specific calorie range or less.

18. The mobile terminal of claim 15, wherein the controller is configured to display each exercise type on the display unit if an exercise type of the first exercise information and an exercise type of the second exercise information are different.

19. The mobile terminal of claim 1, further comprising an input unit, wherein the controller is configured to:
set at least one of exercise facility information, exercise record information, and topography information related to information about a location of the mobile terminal and input information of the user received through the input unit as parameters, and
recommend an appropriate exercise type and exercise method.

20. The mobile terminal of claim 19, wherein:
the input information of the user comprises information about at least one of an exercise limit time, target calories, and sporting equipment to be used, and
the controller is configured to recommend the appropriate exercise type and exercise method again if at least one of the parameters is changed.

* * * * *